(12) United States Patent
Kawasuji et al.

(10) Patent No.: US 7,576,198 B1
(45) Date of Patent: Aug. 18, 2009

(54) INTEGRASE INHIBITORS CONTAINING AROMATIC HETEROCYCLE DERIVATIVES

(75) Inventors: Takashi Kawasuji, Osaka (JP); Tomokazu Yoshinaga, Settsu (JP)

(73) Assignee: Shionogi & Co., Ltd., Osaka (JP)

( * ) Notice: Subject to any disclaimer, the term of this patent is extended or adjusted under 35 U.S.C. 154(b) by 596 days.

(21) Appl. No.: 10/069,999

(22) PCT Filed: Aug. 25, 2000

(86) PCT No.: PCT/JP00/05754

§ 371 (c)(1), (2), (4) Date: Mar. 1, 2002

(87) PCT Pub. No.: WO01/17968

PCT Pub. Date: Mar. 15, 2001

(30) Foreign Application Priority Data

Sep. 2, 1999 (JP) .................. 11/248206

(51) Int. Cl.
C07D 201/16 (2006.01)
C07D 267/02 (2006.01)
C07D 281/08 (2006.01)
C07D 515/00 (2006.01)
A61K 38/00 (2006.01)

(52) U.S. Cl. .................... 540/54; 540/13; 540/51; 544/3; 546/4; 548/119; 548/174; 549/6; 549/13

(58) Field of Classification Search ............... 540/13, 540/51, 54; 544/3; 546/4; 548/119, 174; 549/6, 13

See application file for complete search history.

(56) References Cited

U.S. PATENT DOCUMENTS

| | | | | |
|---|---|---|---|---|
| 4,252,951 | A | * | 2/1981 | Jackson et al. ............... 540/220 |
| 5,480,887 | A | | 1/1996 | Hornback et al. |
| 5,591,773 | A | | 1/1997 | Grunberger et al. |
| 5,780,640 | A | | 7/1998 | Kretzschmar et al. |
| 6,864,244 | B2 | * | 3/2005 | Connolly et al. ............... 514/49 |

FOREIGN PATENT DOCUMENTS

| | | | |
|---|---|---|---|
| EP | 0220947 | | 5/1987 |
| EP | 0 696 586 A1 | * | 4/1994 |
| EP | 9 913 392 A1 | * | 5/1999 |
| GB | 2113687 | | 8/1983 |
| WO | WO 99/06410 | * | 2/1999 |
| WO | 99/26943 | | 6/1999 |

OTHER PUBLICATIONS

Yuan, H.; Parrill, A. L. "QSAR Studies of HIV-1 Integrase Inhibition" Bioorganic & Medicinal Chemistry 10 (2002) 4169-4183.*
Silverman, Richard B. The Organic Chemistry of Drug Design and Drug Action Second Edition. New York: Academic Press, Inc. 2004, pp. 498-500.*
Masquelin, et al. "Synthesis of enantiomerically pure D- and L-(heteroaryl)alanines by asymmetric hydrogenation of (Z)-α-amino-α,β-didehydroesters" Helvetica Chimica Acta 1994, 77(5), 1395-411.*
Patani, G. A.; LaVoie, E. J. "Bioisosterism: A Rational Approach in Drug Design" Chem. Rev. 1996, 96, 3147-3176.*
Brbot-Saranovic et al., "Brbot-Saranovic et al. Structure determination of some pyronylpyrazoles. Correction of the structures described as pyrano[4,3-c]pyrazoles" Heterocycles 1992, 34(8), 1547-54.*
acd/labs, IUPAC Nomenclature of Organic Chemistry. Retrieved at on Aug. 13, 2007 from http://www.acdlabs.icom/iupac/nomenclature/79/r79_53.htm, pp. 1-4.*
acd/labs, IUPAC Nomenclature of Organic Chemistry. Retrieved at on Aug. 13, 2007 from http://www.acdlabs.com/iupac/nomenclature/79/r79_78.htm, pp. 1-3.*
Stein et al., "Immune-based therapeutics: Scientific rationale and the promising approaches ot the treatment of the human immunodeficiency virus-infected individual" CID, 1993, 17, 749-771.*
Cherepanov et al., Solution structure of the HIV-1 integrase-binding domain in LEDGF/p75, pp. 526-532.*
Nair, "HIV integrase as a target for antiviral chemotherapy" Reviews in medical Virology 2002, 12, pp. 179-193.*

(Continued)

*Primary Examiner*—T. D. Wessendorf
(74) *Attorney, Agent, or Firm*—Wenderoth, Lind & Ponack, LLP.

(57) ABSTRACT

A compound of the formula (I):

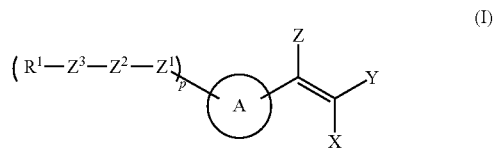

wherein X is hydroxy or the like;
Y is —C(=$R^2$)—$R^3$—$R^4$ wherein $R^2$ and $R^3$ is oxygen atom or the like, $R^4$ is hydrogen, optionally substituted alkyl, optionally substituted heteroaryl or the like;
Z is hydrogen or the like;
$Z^1$ and $Z^3$ each is independently a bond, alkylene or the like;
$Z^2$ is a bond, alkylene, —O— or the like;
$R^1$ is optionally substituted aryl, optionally substituted heteroaryl or the like;
p is 0 to 2 and
ring (A) is optionally substituted aromatic heterocycle, a tautomer of itself, a prodrug thereof, a pharmaceutically acceptable salt thereof or a solvate thereof has an integrase-inhibiting activity.

8 Claims, No Drawings

OTHER PUBLICATIONS

Tramontano et al., "The use of a new in vitro reaction substrate reproducing both U3 and U5 regions of the HIV-1 3' ends increases the correlation between the in vitro and in vivo effects of the HIV-1 integrase inhibitors" Biochemical Pharmacology 2004, 67, 1751-1761.*

Fahey et al., "Status of immune based therapies in HIV infection and AIDS", Clin. exp. Immunol. 1992, 88, 1-5.*

Flint, Enquist, Krug, Racaniello and Skalka, "Principles of Virology" ASM press, 2000, pp. 750-780.*

Braga et al., "Making crystals form crystals: a green route to crystal engineering and polymorphism" ChemComm 2005, 3635-3645.*

Maier et al. Phosphorus, Sulfur Silicon Relat. Elem. 1991, 62(1.4), 15-28.*

Database CHEMABS, Chemical Abstract Service, Brbot-Saranovic et al., "Reactions of ethyl 2-hydroxy-4-(4-hydroxy-6-methyl-2-pyron-3-yl)-4-oxo-2-butenoate with N-nucleophiles. Synthesis of isomeric pyronylpyrazoles and pyrano[4,3-c]pyrazoles" XP002285137 retrieved from STN Database Accession No. 1990:178768.

Database CHEMABS, Chemical Abstract Service, Anderson et al., "Dihydroimidazoles in synthesis: C-acylation of lithiodihydroimidazoles" XP002285138 retieved from STN Database Accession No. 1985:113372.

Database CHEMABS, Chemical Abstract Service, Peresleni et al., "Structure tautomerism, and reactions of β-(3-nitropyrid-2-yl) and β-(3-nitropyrid-4-yl)pyruvic acid esters" XP002285139 retrieved form STN Database Accession No. 1974:436930.

Database Beilstein, Beilstein Institute for Organic Chemistry, XP002285141 Database Accession No. BRN 4550604, 1991.

Database Beilstein, Beilstein Institute for Organic Chemistry, XP002285142 Database Accession No. BRN 6004225, 1993.

Database Beilstein Beilstein Institute for Organic Chemistry, XP002285143 Database Accession No. BRN 4820019, 1992.

X. Chen et al.,"A new procedure to enols of 2-acylmethyl-4,4-dimethyl-2-oxazolines under ultrasonically disperse potassium system", Chinese Journal of Chemistry, vol. 17, No. 1, pp. 80-83, Jan. 1999.

Database CAPLUS 'Online! Chemical Abstracts Service, Columbus, Ohio, US; Brbot-Saranovic, Ana et al: "Reactions of ethyl 2-hydroxy-4-(4-hydroxy-6-methyl-2-pyron-3-yl)-4-oxo-2-butenoate with N-nucleophiles. Synthesis of isomeric pyronylpyrazoles and pyrano [4,3-c] pyrazoles" XP002285137.

Database CAPLUS !Onlie! Chemical Abstracts Service, Columbus Ohio, US; Anderson, Michael W. et al: "Dihydroimidazoles in synthesis: C-acylation of lithiodihydroimidazoles" XP002285138.

Database CAPLUS 'Online! Chemical Abstracts Service, Columbus, Ohio, US; Peresleni, E. M. et al: "Structure. tautomerism, and reactions of .beta. -(3-nitropyrid-2-yl) and .beta. -(3-nitropyrid-4-yl) pyruvic acid esters" XP002285139.

Database Beilstein Beilstein Institute for Organic Chemistry, Frankfurt-Main, DE; XP002285141.

Database Beilstein Beilstein Institute for Organic Chemistry, Frankfurt-Main, DE; XP002285142.

Database Beilstein Beilstein Institute for Organic Chemistry, Frankfurt-Main, DE; XP002285143.

K Hirai et al. "Synthesis of 2-Distributed-amino-4-arylthiazol-5-ylalikanoic Acids", Chem. Pharm. Bull., vol. 25, No. 9, pp. 2292-2299, 1977.

F. R. Heirtzler, "Preparation of non-symmetrical 2,3-bis (2,2'-oligopyridyl)pyrazines via 1,2-disubstituted ethanones" Synlett, No. 8, pp. 1203-1206, Aug. 1999.

X. Chen et al., "A new procedure to enols of 2-acylmethyl-4,4-dimethyl-2-oxazolines under ultrasonically dispersed potassium system", Chin. J. Chem., vol. 17, No. 1, pp. 80-83, Jan. 1999.

S. K. Bertilsson et al., "Chiral N,N'—and N,O-Bidentate Anionic Ligands. Preparation, Metal Complexation, and Evaluation in the Asymmetric Aziridination of Olefins Organometallics", vol. 18, No. 7, pp. 1281-1286, Mar. 1999.

Chemical Abstracts, vol. 117, 1992, Abstract No. 171384, Registry No. 143814-20-4.

Chemical Abstracts, vol. 114, 1991, Abstract No. 122162, Registry No. 129884-23-7 129884-21-5.

Chemical Abstracts, vol. 108, 1988, Abstract No. 150852, Registry No. 111559-36-5 111559-35-4.

Chemical Abstracts, vol. 105, 1986, Abstract No. 6436, Registry No. 102720-85-4.

Gordon N. Walker et al., "Synthesisof Benzol[f]quinolines and Ergolines form 5-Phenyl-6-methyl-2-pyridones", J. Org. Chem., vol. 26, pp. 4441-4456, Nov. 1961.

Rodolfo Nesi et al., "Thermal Rearrangement of Ethyl 5-Nitro-4-phenyl-2-oxa-3-azabicyclo[3.1.0]hex-3-ene-1-carboxylate into a Quinoxaline System", J. Chem. Soc. Chem. Commun., vol. 23, pp. 1675-1676, Jul. 1990.

Ana Brbot-Saranovic et al., "Reactions of Ethyl 2-Hydroxy-4(4-Hydroxy-6-Methyl-2-Pyron-3-YL)-4-Oxo-2-Butenoate With N-Nucleophiles. Synthesis of Isomeric Pyronylpyrazoles and Pyrano[4,3-c]Pyrazoles", Heterocycles, vol. 29, No. 8, pp. 1559-1571, Apr. 1989.

Rok Zupet et al., "A Convenient Synthesis of Alkyl Heteroarylpyruvates" Synthetic Communications, 22(15), pp. 2245-2251, Apr. 1992.

Johannes Meiwes et al., "Asymmetric synthesis of $_L$-thienylalanines", Tetrahedron Assemetry, vol. 8, No. 4, pp. 527-536, Jan. 1997.

V. Boekelheide et al., "Synthesis of Pyrrocolines Unsubstituted in th Five-membered Ring", J. Am. Chem. Soc., vol. 81, pp. 1456-1459, Mar. 1959.

Roger Adams et al., "Condensation Reactions of Picoline 1-Oxies", J. Am. Chem. Soc., vol. 76, pp. 3168-3171, Jun. 1954.

Helvetica Chimica Acta, vol. 38, No. 176, pp. 1452-1472, 1955.

Chemical Abstracts, vol. 103, 1985, Abstract No. 21944, Registry No. 95589-69-8.

Chemical Abstracts, vol. 101, 1984, Abstract No. 211021, Registry No. 93074-95-4.

Chemical Abstracts, vol. 100, 1984, Abstract No. 85565, Registry No. 88474-13-9.

Chemical Abstracts, vol. 90, 1979, Abstract No. 72026, Registry No. 69097-74-1 69097-73- 0 69097-72-9.

* cited by examiner

INTEGRASE INHIBITORS CONTAINING AROMATIC HETEROCYCLE DERIVATIVES

This application is a 371 of PCT/JP00/05754 filed Aug. 25, 2000.

TECHNICAL FIELD

The present invention relates to integrase inhibitors comprising aromatic heterocycle derivatives, in detail HIV integrase inhibitors comprising aromatic heterocycle derivatives.

BACKGROUND ART

Among viruses, human immunodeficiency virus (HIV), a kind of retrovirus, is known to cause acquired immunodeficiency syndrome (AIDS). The therapeutic agent for AIDS is mainly selected from the group of reverse transcriptase inhibitors (e.g., AZT, 3TC, and the like) and protease inhibitors (e.g., Indinavir and the like), but they are proved to be accompanied by side effects such as nephropathy and the emergence of resistant viruses. Thus, the development of anti-HIV agents having the other mechanism of action has been desired.

Under the above circumstance, the research has been focused on integrase, which is an enzyme relating to the site-specific recombination or insertion of viral DNA into chromosomes in animal cells, and the research for anti-HIV agents based on the enzyme inhibitory activity has been performed; (1) KOURILSKY P et al., Proc. Natl. Acad. Sci. USA 61 (3), 1013-1020 (1968); (2) F Barin et al., J. VIROL. METHODS (NETHERLANDS), 17/1-2(55-61) (1987); (3) Fesen. MR, Proc. Natl. Acad. Sci. USA 90: 2399, (1993); (4) DeNoon, DJ, CDC AIDS Weekly Pagination:P2 (1990). Some integrase inhibitors have recently been reported, for example, peptide derivatives described in U.S. Pat. No. 5,578, 573, tetrahydronaphthyl derivatives described in GB 2306476A, and acrydone derivatives described in WO 97/38999.

Pyridine derivatives substituted with oxo propanoic acid are disclosed in J. Org. Chem. 1961 (26), p 4441. Quinoxaline derivatives substituted with oxo propanoic acid are disclosed in J. Chem. Soc. Chem. Commun. 1990, 23, p 1675-1676. Pyrazole derivatives substituted with oxo propanate ester are disclosed in Heterocycles, 1989, 29, p 1559. Pyridine, benzothiazole and pyrazine derivatives substituted with oxo propane acid ester are disclosed in Synth. Commun. 1992, 22(15), p 2245-2251. It is not disclosed in all the above documents that these compounds have an anti-HIV activity and anti-integrase inhibitory activity.

A combination therapy is reported to be efficient in treatment for acquired immunodeficiency syndrome against the frequent emergence of the resistant mutant in Balzarini, J. et al, Proc. Natl. Acad. Sci. USA 1996, 93, p 13152-13157. Reverse transcriptase inhibitors and protease inhibitors are clinically used as an anti-HIV agent but agents having the same mechanism of action often exhibit cross resistance or only an additional activity. Therefore, anti-HIV agents having the other mechanism of action are desired.

DISCLOSURE OF INVENTION

Under the above circumstance, the development of a novel integrase inhibitor has been desired. The present inventors have intensively studied to find that a novel aromatic heterocycle derivative, namely, a compound of the general formula (I), a tautomer of itself, a prodrug thereof, a pharmaceutically acceptable salt thereof or a solvate thereof has an integrase-inhibiting activity and is useful as an antiviral agent, especially an anti-HIV agent, to accomplish the present invention.

The present invention relates to 1) a pharmaceutical composition having an integrase-inhibiting activity which comprises as an active ingredient a compound of the formula (I):

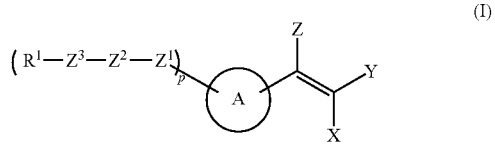

(I)

wherein X is hydroxy or optionally substituted amino;

Y is —C(=$R^2$)—$R^3$—$R^4$ wherein $R^2$ is oxygen atom or sulfur atom, $R^3$ is oxygen atom, sulfur atom or N—$R^5$, $R^4$ is hydrogen, optionally substituted alkyl, optionally substituted alkenyl, optionally substituted alkynyl or optionally substituted aralkyl and $R^5$ is hydrogen, optionally substituted alkyl, optionally substituted alkenyl, optionally substituted alkynyl, optionally substituted alkoxy, optionally substituted cycloalkyl or optionally substituted aralkyl, or $R^4$ and $R^5$ may be taken together with the adjacent nitrogen atom to form optionally substituted non-aromatic heterocyclic group, —S(=O)$_q$—$R^6$—$R^7$ wherein $R^6$ is oxygen atom or N—$R^7$, $R^7$ each is independently hydrogen, optionally substituted alkyl, optionally substituted alkenyl, optionally substituted alkynyl or optionally substituted aralkyl and q is 1 or 2, —S(=O)$_q$—$R^8$ wherein $R^8$ is optionally substituted alkyl, optionally substituted alkenyl, optionally substituted alkynyl or optionally substituted aralkyl and q is as defined above, —P(=O)(O$R^9$)$_2$ wherein $R^9$ each is independently hydrogen or optionally substituted alkyl, halogenated alkyl or optionally substituted heteroaryl;

Z is hydrogen, optionally substituted alkyl or optionally substituted aralkyl;

$Z^1$ and $Z^3$ each is independently a bond, alkylene or alkenylene;

$Z^2$ is a bond, alkylene, alkenylene, —CH(OH)—, —S—, —SO—, —SO$_2$—, —SO$_2$N$R^{10}$—, —N$R^{10}$SO$_2$—, —O—, —N$R^{10}$—, —N$R^{10}$CO—, —CON$R^{10}$—, —C(=O)—O—, —O—C(=O)— or —CO—;

$R^{10}$ is hydrogen, optionally substituted alkyl, optionally substituted alkenyl, optionally substituted alkynyl or optionally substituted aralkyl;

$R^1$ is optionally substituted alkyl, optionally substituted alkenyl, optionally substituted alkynyl, optionally substituted cycloalkyl, optionally substituted cycloalkenyl, optionally substituted non-aromatic heterocyclic group, optionally substituted aryl or optionally substituted heteroaryl;

p is 0 to 2, provided that when p is 2, the groups of the formula: —$Z^1$—$Z^2$—$Z^3$—$R^1$ may be different from each other; and ring (A) is optionally substituted aromatic heterocycle, a tautomer of itself, a prodrug thereof, a pharmaceutically acceptable salt thereof or a solvate thereof, 2) the pharmaceutical composition having an integrase-inhibiting activity according to the above 1) wherein the group of the formula: —C(Z)=C(X)Y in the formula (I) substitutes at an atom adjacent to a hetero atom in ring (A), 3) the pharmaceutical composition having an integrase-inhibiting activity according to the above 1) or 2) wherein Y is optionally substituted heteroaryl; and the heteroaryl has a bond at an atom adjacent to a hetero atom in Y, 4) the pharmaceutical composition having an integrase-inhibiting activity according to the above 1) or 2) wherein X is hydroxy and Y is —C(=R$^2$)—R$^3$—R$^4$ wherein R$^2$ is oxygen atom, R$^3$ is oxygen atom or N—R$^5$, R$^4$ is hydrogen, optionally substituted alkyl, optionally substituted alkenyl, optionally substituted alkynyl or optionally substituted aralkyl and R$^5$ is hydrogen, optionally substituted alkyl, optionally substituted alkenyl, optionally substituted alkynyl, optionally substituted alkoxy, optionally substituted cycloalkyl or optionally substituted aralkyl, or R$^4$ and R$^5$ may be taken together with the adjacent nitrogen atom to form optionally substituted non-aromatic heterocyclic group;

optionally substituted tetrazolyl; optionally substituted triazolyl; optionally substituted thiazolyl; optionally substituted isoxazolyl; optionally substituted pyrazinyl; optionally substituted imidazolyl; optionally substituted pyrimidinyl or optionally substituted pyridyl, 5) the pharmaceutical composition having an integrase-inhibiting activity according to any one of the above 1) to 4) wherein ring (A) is optionally substituted pyridine, optionally substituted pyrazine, optionally substituted pyrimidine, optionally substituted oxazole, optionally substituted thiadiazole, optionally substituted quinoline, optionally substituted isoquinoline, optionally substituted purine, optionally substituted benzoxazole or optionally substituted benzimidazole, 6) the pharmaceutical composition having an integrase-inhibiting activity according to any one of the above 1) to 5) wherein p is 1; Z$^1$ and Z$^3$ each is independently a bond or alkylene; Z$^2$ is a bond, alkylene or —O— and R$^1$ is optionally substituted alkyl, optionally substituted cycloalkyl, optionally substituted aryl or optionally substituted heteroaryl, 7) a compound of the formula (I):

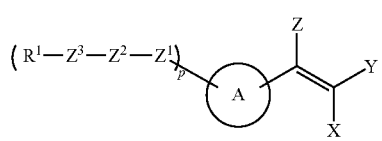

wherein X is hydroxy or optionally substituted amino;

Y is —C(=R$^2$)—R$^3$—R$^4$ wherein R$^2$ is oxygen atom or sulfur atom, R$^3$ is oxygen atom, sulfur atom or N—R$^5$, R$^4$ is hydrogen, optionally substituted alkyl, optionally substituted alkenyl, optionally substituted alkynyl or optionally substituted aralkyl and R$^5$ is hydrogen, optionally substituted alkyl, optionally substituted alkenyl, optionally substituted alkynyl, optionally substituted alkoxy, optionally substituted cycloalkyl or optionally substituted aralkyl, or R$^4$ and R$^5$ may be taken together with the adjacent nitrogen atom to form optionally substituted non-aromatic heterocyclic group;

—S(=O)$_q$—R$^6$—R$^7$ wherein R$^6$ is oxygen atom or N—R$^7$, R$^7$ each is independently hydrogen, optionally substituted alkyl, optionally substituted alkenyl, optionally substituted alkynyl or optionally substituted aralkyl and q is 1 or 2;

—S(=O)$_q$—R$^8$ wherein R$^8$ is optionally substituted alkyl, optionally substituted alkenyl, optionally substituted alkynyl or optionally substituted aralkyl and q is as defined above;

—P(=O)(OR$^9$)$_2$ wherein R$^9$ each is independently hydrogen or optionally substituted alkyl;

halogenated alkyl or optionally substituted heteroaryl;

Z is hydrogen, optionally substituted alkyl or optionally substituted aralkyl;

Z$^1$ and Z$^3$ each is independently a bond, alkylene or alkenylene;

Z$^2$ is a bond, alkylene, alkenylene, —CH(OH)—, —S—, —SO—, —SO$_2$—, —SO$_2$NR$^{10}$—, —NR$^{10}$SO$_2$—, —O—, —NR$^{10}$—, —NR$^{10}$CO—, —CONR$^{10}$—, —C(=O)—O—, —O—C(=O)— or —CO—;

R$^{10}$ is hydrogen, optionally substituted alkyl, optionally substituted alkenyl, optionally substituted alkynyl or optionally substituted aralkyl;

R$^1$ is optionally substituted branched alkyl, optionally substituted alkenyl, optionally substituted alkynyl, optionally substituted cycloalkyl, optionally substituted cycloalkenyl, optionally substituted non-aromatic heterocyclic group, optionally substituted aryl or optionally substituted heteroaryl;

p is 1 to 2, provided that when p is 2, the groups of the formula: —Z$^1$—Z$^2$—Z$^3$—R$^1$ are different from each other;

ring (A) is optionally substituted aromatic heterocycle; and the group of the formula: —C(Z)=C(X)Y in the formula (I) substitutes at an atom adjacent to a hetero atom in ring (A);

provided compounds wherein X is hydroxy; Y is —C(=R$^2$)—R$^3$—R$^4$ wherein R$^2$ is oxygen atom; R$^3$ is oxygen atom; R$^4$ is hydrogen, methyl or ethyl; Z is hydrogen; Z$^1$, Z$^2$ and Z$^3$ is a bond; R$^1$ is unsubstituted phenyl, p is 1; and ring (A) is optionally substituted pyridine or optionally substituted pyrazole are excluded, a tautomer of itself, a prodrug thereof, a pharmaceutically acceptable salt thereof or a solvate thereof, 8) the compound according to the above 7) wherein Y is optionally substituted heteroaryl; and the heteroaryl has a bond at an atom adjacent to a hetero atom in Y, a tautomer of itself, a prodrug thereof, a pharmaceutically acceptable salt thereof or a solvate thereof, 9) the compound according to the above 7) or 8) wherein X is hydroxy;

Y is —C(=R$^2$)—R$^3$—R$^4$ wherein R$^2$ is oxygen atom, R$^3$ is oxygen atom or N—R$^5$, R$^4$ is hydrogen, optionally substituted alkyl, optionally substituted alkenyl, optionally substituted alkynyl or optionally substituted aralkyl and R$^5$ is hydrogen, optionally substituted alkyl, optionally substituted alkenyl, optionally substituted alkynyl, optionally substituted alkoxy, optionally substituted cycloalkyl or optionally substituted aralkyl, or R$^4$ and R$^5$ may be taken together with the adjacent nitrogen atom to form optionally substituted non-aromatic heterocyclic group;

optionally substituted tetrazolyl; optionally substituted triazolyl; optionally substituted thiazolyl; optionally substituted isoxazolyl; optionally substituted pyrazinyl; optionally substituted imidazolyl; optionally substituted pyrimidinyl or optionally substituted pyridyl, a tautomer of itself, a prodrug thereof, a pharmaceutically acceptable salt thereof or a solvate thereof, 10) the compound according to any one of the above 7) to 9) wherein ring (A) is optionally substituted aromatic heterocycle containing nitrogen atom, a tautomer of itself, a prodrug thereof, a pharmaceutically acceptable salt thereof or a solvate thereof, 11) the compound according to any one of the above 7) to 10) wherein ring (A) is optionally substituted pyridine, optionally substituted pyrazine, optionally substituted pyrimidine, optionally substituted oxazole, optionally substituted thiadiazole, optionally substituted quinoline, optionally substituted isoquinoline, optionally substituted purine, optionally substituted benzoxazole or optionally substituted benzimidazole, a tautomer of itself, a prodrug thereof, a pharmaceutically acceptable salt thereof or a solvate thereof, 12) the compound according to any one of the above 7) to 11) wherein $Z^2$ is a bond, alkylene or —O—, a tautomer of itself, a prodrug thereof, a pharmaceutically acceptable salt thereof or a solvate thereof, 13) the compound according to any one of the above 7) to 12) wherein $Z^1$ and $Z^3$ each is independently a bond or alkylene; $R^1$ is optionally substituted branched alkyl, optionally substituted cycloalkyl, optionally substituted non-aromatic heterocyclic group, optionally substituted aryl or optionally substituted heteroaryl, a tautomer of itself, a prodrug thereof, a pharmaceutically acceptable salt thereof or a solvate thereof, 14) the compound according to any one of the above 7) to 13) wherein $Z^1$ is a bond; $Z^2$ is alkylene or —O—; $Z^3$ is a bond or alkylene; and ring (A) is optionally substituted pyridine, a tautomer of itself, a prodrug thereof, a pharmaceutically acceptable salt thereof or a solvate thereof, 15) a compound of the formula (XIIc):

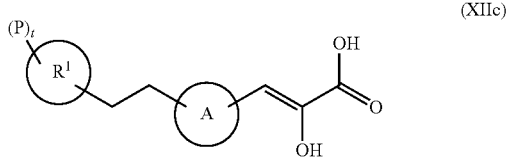

wherein ring (A) is optionally substituted aromatic heterocycle; $R^1$ is heteroaryl or aryl; P is hydroxy, carboxy, halogen, halogenated alkyl, alkyl, alkenyl, alkynyl, cycloalkyl, cycloalkenyl, alkoxy, alkoxycarbonyl, nitro, nitroso, optionally substituted amino, azido, aryl, aralkyl, cyano, isocyano, isocyanato, thiocyanato, isothiocyanato, mercapto, alkylthio, alkylsulfonyl, optionally substituted carbamoyl, sulfamoyl, acyl, formyloxy, haloformyl, oxalo, mercapto, thioformyl, thiocarboxy, dithiocarboxy, thiocarbamoyl, sulfino, sulfo, sulfoamino, hydrazino, azido, ureido, amidino or guanidino; and t is 0 to 5, 16) a library of the compound according to the above 15).

17) a pharmaceutical composition which comprises as an active ingredient the compound according to any one of the above 7) to 15), a tautomer of itself, a prodrug thereof, a pharmaceutically acceptable salt thereof or a solvate thereof, 18) a pharmaceutical composition useful for an anti-viral agent which comprises as an active ingredient the compound according to any one of the above 7) to 15), a tautomer of itself, a prodrug thereof, a pharmaceutically acceptable salt thereof or a solvate thereof, 19) a pharmaceutical composition useful for an anti-HIV agent which comprises as an active ingredient the compound according to any one of the above 7) to 15), a tautomer of itself, a prodrug thereof, a pharmaceutically acceptable salt thereof or a solvate thereof, 20) a pharmaceutical composition having an integrase-inhibiting activity comprises as an active ingredient the compound according to any one of the above 7) to 15), a tautomer of itself, a prodrug thereof, a pharmaceutically acceptable salt thereof or a solvate thereof, 21) an anti-HIV medical mixture which comprises a reverse transcriptase inhibitor and/or a protease inhibitor in addition to the integrase inhibitor according to any one of the above 1) to 6) and 20), 22) the pharmaceutical composition according to any one of the above 1) to 6) and 20) which enhances an anti-HIV activity of a reverse transcriptase inhibitor and/or a protease inhibitor, 23) a method for treating AIDS or AIDS-related complication which comprises administering the integrase inhibitor according to any one of the above 1) to 6) and 20), and 24) use of the compound according to any one of the above 1) to 6) and 20) for the manufacture of a pharmaceutical composition having an integrase-inhibiting activity.

BEST MODE FOR CARRYING OUT THE INVENTION

One of the structural characters of the compound of the formula (I) is that ring (A) is optionally substituted aromatic heterocycle and the aromatic heterocycle is substituted with a group of the formula: —C(Z)═C(X)Y wherein X is hydroxy or optionally substituted amino;

Y is —C(═$R^2$)—$R^3$—$R^4$ wherein $R^2$ is oxygen atom or sulfur atom, $R^3$ is oxygen atom, sulfur atom or N—$R^5$, $R^4$ is hydrogen, optionally substituted alkyl, optionally substituted alkenyl, optionally substituted alkynyl or optionally substituted aralkyl and $R^5$ is hydrogen, optionally substituted alkyl, optionally substituted alkenyl, optionally substituted alkynyl, optionally substituted alkoxy, optionally substituted cycloalkyl or optionally substituted aralkyl, or $R^4$ and $R^5$ may be taken together with the adjacent nitrogen atom to form optionally substituted non-aromatic heterocyclic group;

—S(═O)$_q$—$R^6$—$R^7$ wherein $R^6$ is oxygen atom or N—$R^7$, $R^7$ each is independently hydrogen, optionally substituted alkyl, optionally substituted alkenyl, optionally substituted alkynyl or optionally substituted aralkyl and q is 1 or 2;

—S(═O)$_q$—$R^8$ wherein $R^8$ is optionally substituted alkyl, optionally substituted alkenyl, optionally substituted alkynyl or optionally substituted aralkyl and q is as defined above;

—P(═O)(O$R^9$)$_2$ wherein $R^9$ each is independently hydrogen or optionally substituted alkyl;

halogenated alkyl or optionally substituted heteroaryl and

Z is hydrogen, optionally substituted alkyl or optionally substituted aralkyl.

Preferred is a compound wherein the group of the formula: —C(Z)=C(X)Y wherein X, Y and Z are as defined above substitutes at an atom adjacent to a hetero atom in ring (A). An example is the following compound of the formula:

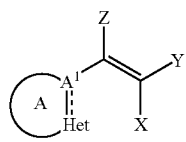

wherein Het is a hetero atom in ring (A); $A^1$ is an atom adjacent to the above hetero atom in ring (A); a dotted line is the presence or absence of a bond; the other terms are as defined above; and ring (A) may have hetero atoms other than Het.

When Y is optionally substituted heteroaryl, preferred is a compound wherein the heteroaryl has a bond at an atom adjacent to a hetero atom in Y. An example is the following compound of the formula:

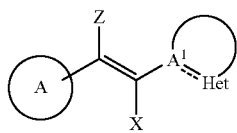

wherein Het is a hetero atom in heteroaryl; $Y^1$ is an atom adjacent to the hetero atom.

The group of the formula:

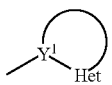

corresponds to Y. A dotted line is the presence or absence of a bond, the other terms are as defined above, and Y may have hetero atoms other than Het.

Preferred is a compound wherein Y is —C(=$R^2$)—$R^3$—$R^4$, —S(=O)$_q$—$R^6$—$R^7$, —S(=O)$_q$—$R^8$ or —P(=O)(O$R^9$)$_2$ wherein each term is as defined above, because an oxygen atom or a nitrogen atom of the above substituents can be located at the same position of the hetero atom (Het) in heteroaryl and such compound, as a result, exhibits a high integrase-inhibiting activity.

One of the structural characters of the compound of the formula (I) is that the aromatic heterocycle (ring (A)) may be substituted with a group of the formula: —$Z^1$—$Z^2$—$Z^3$—$R^1$ wherein $Z^1$ and $Z^3$ each is independently a bond, alkylene or alkenylene; $Z^2$ is a bond, alkylene, alkenylene, —CH(OH)—, —S—, —SO—, —SO$_2$—, —SO$_2$N$R^{10}$—, —N$R^{10}$SO$_2$—, —O—, —N$R^{10}$—, —N$R^{10}$CO—, —CON$R^{10}$—, —C(=O)—O—, —O—C(=O)— or CO—; $R^{10}$ is hydrogen, optionally substituted alkyl, optionally substituted alkenyl, optionally substituted alkynyl or optionally substituted aralkyl; $R^1$ is optionally substituted alkyl, optionally substituted alkenyl, optionally substituted alkynyl, optionally substituted cycloalkyl, optionally substituted cycloalkenyl, optionally substituted non-aromatic heterocyclic group, optionally substituted aryl or optionally substituted heteroaryl besides the above group of the formula: —C(Z)=C(X)Y wherein X, Y and Z are as defined above.

Preferable examples of the compound (1) are shown below.
(A-1) 3-(5-Benzyloxypyridin-2-yl)-2-hydroxy acrylic acid.
(A-2) 3-(5-Benzyloxypyridin-2-yl)-2-hydroxy acrylic acid ethyl ester.
(A-3) 3-(3-Isopropoxypyrazin-2-yl)-2-hydroxy acrylic acid.
(A-4) 3-[6-(2-Phenylethyl)pyrimidin-4-yl)-2-hydroxy acrylic acid.
(A-5) 3-[6-(2-Phenylethyl)pyrimidin-4-yl)-2-hydroxy acrylic acid ethyl ester.
(A-6) 3-[5-(2-Phenylethyl)[1,3,4]thiadiazol-2-yl)-2-hydroxy acrylic acid.
(A-7) 3-[5-(2-Phenylethyl)[1,3,4]thiadiazol-2-yl)-2-hydroxy acrylic acid ethyl ester.
(A-8) 3-(4-Benzyloxypyridin-2-yl)-2-hydroxy acrylic acid.
(A-9) 3-(4-Benzyloxypyridin-2-yl)-2-hydroxy acrylic acid ethyl ester.
(A-10) 3-(5-Isopentoxypyridin-2-yl)-2-hydroxy acrylic acid.
(A-11) 3-[5-(Cyclohexylmethoxy)pyridin-2-yl]-2-hydroxy acrylic acid.
(A-12) 3-[5-(2-Phenylethoxy)pyridin-2-yl]-2-hydroxy acrylic acid ethyl ester.
(A-13) 3-[5-(2-Phenylethyl)pyradin-2-yl]-2-hydroxy acrylic acid ethyl ester.
(A-14) 3-[5-(2-Phenylethyl)pyradin-2-yl]-2-hydroxy acrylic acid.
(A-15) 3-(Isoquinolin-3-yl)-2-hydroxy acrylic acid.
(A-16) 3-(5-hydroxypyridin-2-yl)-2-hydroxy acrylic acid ethyl ester.
(A-17) 3-[5-(4-Trifluoromethylbenzyloxy)pyridin-2-yl]-2-hydroxy acrylic acid ethyl ester.
(A-18) 3-[5-(4-Trifluoromethylbenzyloxy)pyridin-2-yl]-2-hydroxy acrylic acid.
(A-19) 3-[5-(2,4-Difluorobenzyloxy)pyridin-2-yl]-2-hydroxy acrylic acid ethyl ester.
(A-20) 3-[5-(2,4-Difluorobenzyloxy)pyridin-2-yl]-2-hydroxy acrylic acid.
(A-21) 3-[5-(2-Naphthylmethoxy)pyridin-2-yl]-2-hydroxy acrylic acid ethyl ester.
(A-22) 3-[5-(3-Carboxyoxalyl-2,4-difluorobenzyloxy)-pyridin-2-yl]-2-hydroxy acrylic acid.
(A-23) 2-(5-Benzyloxypyridin-2-yl)-1-(1H-[1,2,4]triazol-3-yl) ethenol.
(A-24) 2-(5-Benzyloxypyridin-2-yl)-1-thiazol-2-yl ethenol.
(A-25) 3-(Benzoxazol-2-yl)-2-hydroxy-2-propanoic acid.

The present invention provides the compound of the formula (I), the tautomer of itself, the prodrug thereof, the pharmaceutically acceptable salt, the solvate thereof, the pharmaceutical composition comprising them, the anti-viral agent, the anti-HIV agent, the integrase inhibitor or the HIV-medical mixture. They are useful as not only an anti-HIV agent, but also an AIDS-treating agent for AIDS and AIDS-related clinical conditions such as AIDS-related complication (ARC), progressive generalized lymphadenia (PGL), Kaposi sarcoma, pneumocystis carini pneumonia and sudden thrombocytopenic purpura, as well as AIDS-related neurological conditions such as AIDS dementia complication, AIDS brain fever, multiple sclerosis and tropical paraparesis, and positive conditions of anti-HIV antibody and HIV, which includes those of asymptomatic patients.

The terms used in the present specification are explained below. Each term by itself or as part of (an) other substituent(s) has the following meaning.

The term "aromatic heterocycle" of ring (A) includes a 5- to 8-membered aromatic group containing 1 to 4 oxygen atom, sulfur atom and/or nitrogen atom in the ring, or the said aromatic ring fused with one to four 5- to 8-membered aromatic carbon ring or other 5- to 8-membered heteroaromatic ring, which has a radical group at any substitutable position. The term "aromatic heterocycle" includes monocyclic aromatic heterocycle or polycyclic aromatic heterocycle.

The term "monocyclic aromatic heterocycle" includes a 5- to 8-membered aromatic group containing 1 to 4 oxygen atom, sulfur atom and/or nitrogen atom in the ring, which has a radical group at any substitutable position.

The term "polycyclic aromatic heterocycle" includes a 5- to 8-membered aromatic group containing 1 to 4 oxygen atom, sulfur atom and/or nitrogen atom in the ring, fused with one to four 5- to 8-membered aromatic carbon ring or other 5- to 8-membered heteroaromatic ring, which has a radical group at any substitutable position.

Examples of "aromatic heterocycle" includes monocyclic aromatic heterocycle such as furan, thiophen, pyrrole, imidazole, pyrazole, triazole, tetrazole, oxazole, isoxazole, thiazole, thiadiazole, isothiazole, pyridine, pyridazine, pyrimidine, furazan, pyradine or the like, and polycyclic aromatic heterocycle such as benzofuran, benzothiophen, benzimidazole, dibenzofuran, benzoxazole, quinoxaline, cinnoline, quinazoline, quinoline, phthalazine, isoquinoline, purine, pteridine, carbazole, phenanthridine, acridine, indole, isoindole, phenazine or the like.

One of preferred embodiments of "aromatic heterocycle" is aromatic heterocycle containing nitrogen atom. "Aromatic heterocycle containing nitrogen atom" includes an aromatic heterocycle containing one or more nitrogen atom in the ring, for example, pyrrole, imidazole, pyrazole, triazole, tetrazole, oxazole, isoxazole, thiazole, thiadiazole, isothiazole, pyridine, pyridazine, pyrimidine, furazan, benzimidazole, benzoxazole, quinoxaline, cinnoline, quinazoline, quinoline, phthalazine, isoquinoline, purine, pteridine, carbazole, phenanthridine, acridine, indole, isoindole, phenazine or the like.

Preferred is an aromatic heterocycle wherein the group of the formula: —C(Z)=C(X)Y in the formula (I) substitutes at an atom adjacent to a hetero atom in "aromatic heterocycle" of ring (A). In this case, more preferred is an aromatic heterocycle wherein the hetero atom has a lone pair not relating to the conjugation of aromatic ring. Examples of such aromatic heterocycle include furan, thiophen, imidazole, pyrazole, triazole, tetrazole, oxazole, isoxazole, thiazole, thiadiazole, isothiazole, pyridine, pyridazine, pyrimidine, furazan, pyrazine, benzofuran, benzothiophen, benzimidazole, benzoxazole, quinoxaline, cinnoline, quinazoline, quinoline, phthalazine, isoquinoline, purine, pteridine, phenanthridine or the like.

Preferred examples of "aromatic heterocycle" include pyridine, pyrazine, pyrimidine, oxazole, thiadiazole, quinoline, isoquinoline, purine, benzoxazole or benzimidazole.

The term "heteroaryl" includes a group derived from the above "aromatic heterocycle" by removing one hydrogen atom on carbon atom or nitrogen atom in the ring, for example, furyl (e.g., furan-2-yl, furan-3-yl), thienyl (e.g., thiophen-2-yl, thiophen-3-yl), pyrrolyl (e.g., pyrrol-1-yl, pyrrol-2-yl, pyrrol-3-yl), imidazolyl (e.g., imidazol-1-yl, imidazol-2-yl, imidazol-4-yl), pyrazolyl (e.g., pyrazol-1-yl, pyrazol-3-yl, pyrazol-4-yl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., oxazol-2-yl, oxazol-4-yl, oxazol-5-yl), isoxazolyl (e.g., isoxazol-3-yl, isoxazol-4-yl, isoxazol-5-yl), thiazolyl (e.g., thiazol-2-yl, thiazol-4-yl, thiazol-5-yl), thiadaizolyl, isothiazolyl (e.g., isothiazol-3-yl, isothiazol-4-yl, isothiazol-5-yl), pyridyl (e.g., pyridin-2-yl, pyridin-3-yl, pyridin-4-yl), pyridazinyl (e.g., pyridazin-3-yl, pyridazin-4-yl), pyrimidinyl (e.g., pyrimidin-2-yl, pyrimidin-4-yl, pyrimidin-5-yl), furazanyl (e.g., furazan-3-yl), pyrazinyl (e.g., pyrazin-2-yl), oxadiazolyl (e.g., 1,3,4-oxadiazol-2-yl), benzofuryl (e.g., benzo[b]furan-2-yl, benzo[b]furan-3-yl, benzo[b]furan-4-yl, benzo[b]furan-5-yl, benzo[b]furan-6-yl, benzo[b]furan-7-yl), benzothienyl (e.g., benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), benzimidazolyl (e.g., benzimidazol-1-yl, benzimidazol-2-yl, benzimidazol-4-yl, benzimidazol-5-yl), dibenzofuryl, benzoxazolyl, quinoxalinyl (e.g., quinoxalin-2-yl, quinoxalin-5-yl, quinoxalin-6-yl), cinnolinyl (e.g., cinnolin-3-yl, cinnolin-4-yl, cinnolin-5-yl, cinnolin-6-yl, cinnolin-7-yl, cinnolin-8-yl), quinazolinyl (e.g., quinazolin-2-yl, quinazolin-4-yl, quinazolin-5-yl, quinazolin-6-yl, quinazolin-7-yl, quinazolin-8-yl), quinolinyl (e.g., quinolin-2-yl, quinolin-3-yl, quinolin-4-yl, quinolin-5-yl, quinolin-6-yl, quinolin-7-yl, quinolin-8-yl), phthalazinyl (e.g., 1-phthalazinyl, 5-phthalazinyl, 6-phthalazinyl), isoquinolinyl (e.g., isoquinolin-1-yl, isoquinolin-3-yl, isoquinolin-4-yl, isoquinolin-5-yl, isoquinolin-6-yl, isoquinolin-7-yl, isoquinolin-8-yl), purinyl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., indol-1-yl, indol-2-yl, indol-4-yl, indol-5-yl, indol-6-yl, indol-7-yl), isoindolyl, phenazinyl (e.g., 1-phenazinyl, 2-phenazinyl), phenothiazinyl (e.g., 1-phenothiazinyl, 2-phenothiazinyl, 3-phenothiazinyl, 4-phenothiazinyl) or the like.

Preferred embodiments of heteroaryl of Y includes 5- or 6-membered ring containing at least one nitrogen atom in the ring. More preferred examples include tetrazolyl, triazolyl, thiazolyl, isoxazolyl, pyrazinyl, imidazolyl, pyrimidinyl, pyridyl, oxazolyl or isothiazolyl. Most preferred embodiment includes a heteroaryl having a bond at an atom adjacent to a hetero atom in the ring. Examples of such heteroaryl are 2H-tetrazol-5-yl, 1H-[1,2,4]triazol-3-yl, thiazol-2-yl, thiazol-4-yl, isoxazol-3-yl, isoxazol-5-yl, pyrazin-2-yl, imidazol-2-yl, pyrimidin-2-yl, pyridin-2-yl or the like.

Preferred embodiment of "heteroaryl" of $R^1$ includes a 5- or 6-membered heteroaryl, for example, furyl, thienyl, pyrrolyl, imidazolyl, pyrazolyl, triazolyl, tetrazolyl, oxazolyl, isoxazolyl, thiazolyl, thiadiazolyl, isothiazolyl, pyridyl, pyridazinyl, pyrimidinyl, furazanyl, pyrazinyl or the like. Most preferred is pyridyl (pyridin-2-yl, pyridin-3-yl, pyridin-4-yl).

The term "aryl" includes monocyclic aromatic hydrocarbon group (e.g., phenyl) or polycyclic aromatic hydrocarbon group (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl). Preferred is phenyl or naphthyl (1-naphthyl, 2-naphthyl).

The term "alkylene" includes C1 to C6 straight or branched alkylene group, for example, methylene, ethylene, trimethylene, propylene, tetramethylene, ethylethylene, pentamethylene, hexamethylene or the like. Preferred is C1 to C6 straight alkylene group such as methylene, ethylene, trimethylene or tetramethylene.

The term "alkenylene" includes the above C2-C6 straight or branched alkenylene group having one or more double bonds, for example, vinylene, propenylene or butenylene. Preferred is a C2-C3 straight alkenylene group, for example, vinylene or propenylene.

The term "alkyl" includes a C1-C8 straight or branched alkyl group, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl or the like.

A preferred embodiment of alkyl of $R^1$ includes branched alkyl, especially, C3-C8 branched alkyl (e.g., isopropyl, isobutyl, sec-butyl, tert-butyl, isopentyl, neopentyl, tert-pentyl, isohexyl).

A preferred embodiment of alkyl of $R^4$, $R^5$, $R^7$, $R^8$, $R^9$ and $R^{10}$ includes C1-C8 straight alkyl (methyl, ethyl, n-propyl, n-butyl, n-pentyl, n-hexyl).

The term "alkenyl" includes the above C2-C8 straight or branched alkenyl having one or more double bond, for example, vinyl, 1-propenyl, 2-propenyl, 1-butenyl, 2-butenyl, 3-butenyl, 1,3-butadienyl, 3-methyl-2-butenyl or the like.

The term "alkynyl" includes the above C2-C8 alkynyl having one or more triple bond, for example, ethynyl, 1-propynyl, 2-propynyl, 1-butynyl, 2-butynyl, 3-butynyl or the like.

The term "cycloalkyl" includes a C3-C10 saturated cyclic hydrocarbon group, for example, cyclopropyl, cyclobutyl, cyclopentyl, cyclohexyl, cycloheptyl, cyclooctyl or the like. Preferred is cyclopentyl or cyclohexyl.

The term "cycloalkenyl" includes a C3-C10 cyclic non-aromatic hydrocarbon group, for example, cyclopropenyl (e.g., 1-cyclopropenyl), cyclobutenyl (e.g., 1-cyclobutenyl), cyclopentenyl (e.g., 1-cyclopenten-1-yl, 2-cyclopenten-1-yl, 3-cyclopenten-1-yl), cyclohexenyl (e.g., 1-cyclohexen-1-yl, 2-cyclohexen-1-yl, 3-cyclohexen-1-yl), cycloheptenyl (e.g., 1-cycloheptenyl), cyclooctenyl (e.g., 1-cyclooctenyl) or the like. Preferred is 1-cyclohexen-1-yl, 2-cyclohexen-1-yl, 3-cyclohexen-1-yl.

The term "aralkyl" includes the above alkyl substituted with one to three the above "aryl", for example, benzyl, diphenylmethyl, triphenylmethyl, phenethyl, 1-naphthylmethyl, 2-naphthylmethyl or the like.

An alkyl part of "alkoxy" includes the above "alkyl", for example, methoxy, ethoxy, n-propoxy, isopropoxy, n-butoxy, isobutoxy, tert-butoxy or the like. Preferred is methoxy or ethoxy.

The term "halogenated alkyl" includes the above alkyl substituted with one or more halogen, especially, a C1-C3 halogenated alkyl, for example, trifluoromethyl, chloromethyl, dichloromethyl, 1,1-dichloroethyl. 2,2,2-trichloroethyl or the like.

The term "non-aromatic heterocyclic group" includes a non-aromatic heterocyclic group containing at least one or more nitrogen atom, oxygen atom or sulfur atom in the ring, which has a radical group at any substitutable position. Examples of "non-aromatic heterocyclic group" include 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperazinyl, 2-piperazinyl, 2-morpholinyl, 3-morpholinyl, morpholino, tetrahydropyranyl or the like. A non-aromatic heterocyclic group includes saturated or unsaturated heterocyclic group.

An alkyl part of "aralkyl", as well as "alkyl", "alkenyl", "alkynyl", "cycloalkyl", "cycloalkenyl" or "non-aromatic heterocyclic group" may be substituted at any position with 1 to 4 of the same or different substituents.

An aryl part of "aralkyl", as well as "aryl", "heteroaryl" or "aromatic heterocycle" may be substituted at any position (e.g., ortho, meta and/or para) with 1 to 4 of the same or different substituents.

Examples of substituents on aryl and alkyl parts of "aralkyl", and substituents of "optionally substituted alkyl", "optionally substituted alkenyl", "optionally substituted alkynyl", "optionally substituted cycloalkyl", "optionally substituted cycloalkenyl", "optionally substituted non-aromatic heterocyclic group", "optionally substituted aryl", "optionally substituted heteroaryl" or "optionally substituted aromatic heterocycle" include hydroxy, carboxy, halogen (F, Cl, Br, I), halogenated alkyl (e.g., $CF_3$, $CH_2CF_3$, $CH_2CCl_3$ or the like), alkyl (e.g., methyl, ethyl, isopropyl, tert-butyl or the like), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy, butoxy or the like), alkoxycarbonyl (e.g., methoxycarbonyl, ethoxycarbonyl, tert-butoxycarbonyl or the like), nitro, nitroso, optionally substituted amino (e.g., alkylamino (e.g., methylamino, ethylamino, dimethylamino or the like), acylamino (e.g., acetylamino, benzoylamino or the like), aralkylamino (e.g., benzylamino, tritylamino), hydroxyamino or the like), azido, aryl (e.g., phenyl or the like), aralkyl (e.g., benzyl or the like), cyano, isocyano, isocyanato, thiocyanato, isothiocyanato, mercapto, alkylthio (e.g., methylthio or the like), alkylsulfonyl (e.g., methanesulfonyl, ethanesulfonyl), optionally substituted carbamoyl, sulfamoyl, acyl (e.g., formyl, acetyl or the like), formyloxy, haloformyl, oxalo, mercapto, thioformyl, thiocarboxy, dithiocarboxy, thiocarbamoyl, sulfino, sulfo, sulfoamino, hydrazino, azido, ureido, amidino, guanidino or the like.

The substituents of "optionally substituted aromatic heterocycle" of the ring (A) of the compound of the formula (I) include the above shown substituents besides the group of the formula: $-Z^1-Z^2-Z^3-R^1$ wherein $Z^1$, $Z^2$, $Z^3$ and $R^1$ are as defined above.

The substituents of "optionally substituted amino" and "optionally substituted carbamoyl" include alkyl (e.g., methyl, ethyl, dimethyl or the like), alkoxyalkyl (e.g., ethoxymethyl, ethoxyethyl or the like), acyl (e.g., formyl, acetyl, benzoyl, toluoyl or the like), aralkyl (e.g., benzyl, trityl or the like), hydroxy or the like.

X is hydroxy or optionally substituted amino. Preferred is hydroxy.

p is 0 to 2. Preferred is 1.

Examples of the group of the formula: $-Z^1-Z^2-Z^3-R^1$ include $-R^1$, $-CH_2-R^1$, $-CH=CH-R^1$, $-CH(OH)-R^1$, $-S-R^1$, $-SO-R^1$, $-SO_2-R^1$, $-SO_2NH-R^1$, $-NHSO_2-R^1$, $-O-R^1$, $-NH-R^1$, $-NHCO-R^1$, $-CONH-R^1$, $-C(=O)-O-R^1$, $-O-C(=O)-R^1$, $-CO-R^1$, $-C_2H_4-R^1$, $-CH=CH-CH_2-R^1$, $-CH(OH)-CH_2-R^1$, $-S-CH_2-R^1$, $-SO-CH_2-R^1$, $-SO_2-CH_2-R^1$, $-SO_2NH-CH_2-R^1$, $-NHSO_2-CH_2-R^1$, $-O-CH_2-R^1$, $-NH-CH_2-R^1$, $-NHCO-CH_2-R^1$, $-CONH-CH_2-R^1$, $-C(=O)-O-CH_2-R^1$, $-O-C(=O)-CH_2-R^1$, $-CO-CH_2-R^1$, $-CH=CH-CH=CH-R^1$, $-CH=CH-CH(OH)-R^1$, $-CH=CH-S-R^1$, $-CH=CH-SO-R^1$, $-CH=CH-SO_2-R^1$, $-CH=CH-SO_2NH-R^1$, $-CH=CH-NHSO_2-R^1$, $-CH=CH-O-R^1$, $-CH=CH-NH-R^1$, $-CH=CH-NHCO-R^1$, $-CH=CH-CONH-R^1$, $-CH=CH-C(=O)-O-R^1$, $-CH=CH-O-C(=O)-R^1$, $-CH=CH-CO-R^1$, $-CH_2-CH=CH-R^1$, $-CH_2-CH(OH)-R^1$, $-CH_2-S-R^1$, $-CH_2-SO-R^1$, $-CH_2-SO_2-R^1$, $-CH_2-SO_2NH-R^1$, $-CH_2-NHSO_2-R^1$, $-CH_2-O-R^1$, $-CH_2-NH-R^1$, $-CH_2-NHCO-R^1$, $-CH_2-CONH-R^1$, $-CH_2-C(=O)-O-R^1$, $-CH_2-O-C(=O)-R^1$, $-CH_2-CO-R^1$, $-CH(OH)-CH=CH-R^1$, $-S-CH=CH-R^1$, $-SO-CH=CH-R^1$, $-SO_2-$ CH=CH—$R^1$, —$SO_2$NH—CH=CH—$R^1$, —NHSO$_2$—CH=CH—$R^1$, —O—CH=CH—$R^1$, —NH—CH=CH—$R^1$, —NHCO—CH=CH—$R^1$, —CONH—CH=CH—$R^1$, —C(=O)—O—CH=CH—$R^1$, —O—C(=O)—CH=CH—$R^1$, —CO—CH=CH—$R^1$, —$C_3H_6$—$R^1$, —$CH_2$—CH=CH—$CH_2$—$R^1$, —$CH_2$—CH(OH)—$CH_2$—$R^1$, —$CH_2$—S—$CH_2$—$R^1$, —$CH_2$—SO—$CH_2$—$R^1$, —$CH_2$—$SO_2$—$CH_2$—$R^1$, —$CH_2$—$SO_2$NH—$CH_2$—$R^1$, —$CH_2$—NHSO$_2$—$CH_2$—$R^1$, —$CH_2$—O—$CH_2$—$R^1$, —$CH_2$—NH—$CH_2$—$R^1$, —$CH_2$—NHCO—$CH_2$—$R^1$, —$CH_2$—CONH—$CH_2$—$R^1$, —$CH_2$—C(=O)—O—$CH_2$—$R^1$, —$CH_2$—O—C(=O)—$CH_2$—$R^1$, —$CH_2$—CO—$CH_2$—$R^1$, —$C_2H_4$—CH=CH—$R^1$, —$CH_2$—CH=CH—CH=CH—$R^1$, —$CH_2$—CH(OH)—CH=CH—$R^1$, —$CH_2$—S—CH=CH—$R^1$, —$CH_2$—SO—CH=CH—$R^1$, —$CH_2$—$SO_2$—CH=CH—$R^1$, —$CH_2$—$SO_2$NH—CH=CH—$R^1$, —$CH_2$—NHSO$_2$—CH=CH—$R^1$, —$CH_2$—O—CH=CH—$R^1$, —$CH_2$—NH—CH=CH—$R^1$, —$CH_2$—NHCO—CH=CH—$R^1$, —$CH_2$—CONH—CH=CH—$R^1$, —$CH_2$—C(=O)—O—CH=CH—$R^1$, —$CH_2$—O—C(=O)—CH=CH—$R^1$, —$CH_2$—CO—CH=CH—$R^1$, —CH=CH—$C_2H_4$—$R^1$, —CH=CH—CH=CH—$CH_2$—$R^1$, —CH=CH—CH(OH)—$CH_2$—$R^1$, —CH=CH—S—$CH_2$—$R^1$, —CH=CH—SO—$CH_2$—$R^1$, —CH=CH—$SO_2$—$CH_2$—$R^1$, —CH=CH—$SO_2$NH—$CH_2$—$R^1$, —CH=CH—NHSO$_2$—$CH_2$—$R^1$, —CH=CH—O—$CH_2$—$R^1$, —CH=CH—NH—$CH_2$—$R^1$, —CH=CH—NHCO—$CH_2$—$R^1$, —CH=CH—CONH—$CH_2$—$R^1$, —CH=CH—C(=O)—O—$CH_2$—$R^1$, —CH=CH—O—C(=O)—$CH_2$—$R^1$ or —CH=CH—CO—$CH_2$—$R^1$ wherein each $R^1$ is optionally substituted alkyl, optionally substituted alkenyl, optionally substituted alkynyl, optionally substituted cycloalkyl, optionally substituted cycloalkenyl, optionally substituted non-aromatic heterocyclic group, optionally substituted aryl or optionally substituted heteroaryl, or the like.

Preferred examples of the group of the formula: —$Z^1$—$Z^2$—$Z^3$—$R^1$ wherein $Z^1$, $Z^2$, $Z^3$ and $R^1$ are as defined above include 1) the group wherein $Z^1$ is a bond or alkylene, 2) the group wherein $Z^1$ is a bond, 3) the group wherein $Z^2$ is a bond, alkylene, —$SO_2$— or —O—, 4) the group wherein $Z^2$ is a bond, alkylene or —O—, 5) the group wherein $Z^2$ is alkylene or —O—, 6) the group wherein $Z^3$ is a bond or alkylene, 7) the group wherein $R^1$ is optionally substituted alkyl, optionally substituted cycloalkyl, optionally substituted aryl or optionally substituted heteroaryl, 8) the group wherein $R^1$ is optionally substituted branched alkyl, optionally substituted alkenyl, optionally substituted alkynyl, optionally substituted cycloalkyl, optionally substituted cycloalkenyl, optionally substituted non-aromatic heterocyclic group, optionally substituted aryl or optionally substituted heteroaryl, 9) the group wherein $R^1$ is optionally substituted branched alkyl, optionally substituted cycloalkyl, optionally substituted non-aromatic heterocyclic group, optionally substituted aryl or optionally substituted heteroaryl, 10) the group wherein $R^1$ is optionally substituted aryl, or the group formed by their combination.

Preferred examples of the group of the formula: —$Z^1$—$Z^2$—$Z^3$—$R^1$ wherein $Z^1$, $Z^2$, $Z^3$ and $R^1$ are as defined above include phenyl, 2-fluorophenyl, 3-fluorophenyl, 4-fluorophenyl, 2-chlorophenyl, 3-chlorophenyl, 4-chlorophenyl, 2,4-difluorophenyl, 2,6-difluorophenyl, 2,5-difluorophenyl, 3,4-difluorophenyl, 4-methylphenyl, 3-trifluoromethylphenyl, 4-trifluoromethylphenyl, 4-hydroxyphenyl, 4-methoxyphenyl, 4-bromophenyl, 4-biphenyl, benzyl, 2-fluorobenzyl, 3-fluorobenzyl, 4-fluorobenzyl, 2-chlorobenzyl, 3-chlorobenzyl, 4-chlorobenzyl, 2,4-difluorobenzyl, 2,6-difluorobenzyl, 2,5-difluorobenzyl, 3,4-difluorobenzyl, 3,6-difluorobenzyl, 4-methylbenzyl, 3-trifluoromethylbenzyl, 4-trifluoromethylbenzyl, 4-hydroxybenzyl, 4-methoxybenzyl, 4-bromobenzyl, 4-phenylbenzyl, 2-phenylethyl, 2-(2-fluorophenyl)ethyl, 2-(3-fluorophenyl)ethyl, 2-(4-fluorophenyl)ethyl, 2-(2-chlorophenyl)ethyl, 2-(3-chlorophenyl)ethyl, 2-(4-chlorophenyl)ethyl, 2-(2,4-difluorophenyl)ethyl, 2-(2,6-difluorophenyl)ethyl, 2-(2,5-difluorophenyl)ethyl, 2-(3,4-difluorophenyl)ethyl, 2-(4-methylphenyl)ethyl, 2-(3-trifluoromethylphenyl)ethyl, 2-(4-trifluoromethylphenyl)ethyl, 2-(4-hydroxyphenyl)ethyl, 2-(4-methoxyphenyl)ethyl, 2-(4-bromophenyl)ethyl, 2-(4-biphenyl)ethyl, benzenesulfonyl, 2-fluorobenzenesulfonyl, 3-fluorobenzenesulfonyl, 4-fluorobenzenesulfonyl, 2-chlorobenzenesulfonyl, 3-chlorobenzenesulfonyl, 4-chlorobenzenesulfonyl, 2,4-difluorobenzenesulfonyl, 2,6-difluorobenzenesulfonyl, 2,5-difluorobenzenesulfonyl, 3,4-difluorobenzenesulfonyl, 4-methylbenzenesulfonyl, 3-trifluoromethylbenzenesulfonyl, 4-trifluoromethylbenzenesulfonyl, 4-hydroxybenzenesulfonyl, 4-methoxybenzenesulfonyl, 4-bromobenzenesulfonyl, 4-phenylbenzenesulfonyl, benzenesulfenyl, 4-fluorobenzenesulfenyl, phenylthio, 2-fluorophenylthio, 3-fluorophenylthio, 4-fluorophenylthio, 2-chlorophenylthio, 3-chlorophenylthio, 4-chlorophenylthio, 2,4-difluorophenylthio, 2,6-difluorophenylthio, 2,5-difluorophenylthio, 3,4-difluorophenylthio, 4-methylphenylthio, 3-trifluoromethylphenylthio, 4-trifluoromethylphenylthio, 4-hydroxyphenylthio, 4-methoxyphenylthio, 4-bromophenylthio, 4-biphenylthio, phenoxy, 2-fluorophenoxy, 3-fluorophenoxy, 4-fluorophenoxy, 2-chlorophenoxy, 3-chlorophenoxy, 4-chlorophenoxy, 2,4-difluorophenoxy, 2,6-difluorophenoxy, 2,5-difluorophenoxy, 3,4-difluorophenoxy, 4-methylphenoxy, 3-trifluoromethylphenoxy, 4-trifluoromethylphenoxy, 4-hydroxyphenoxy, 4-methoxyphenoxy, 4-bromophenoxy, 4-phenylphenoxy, benzoyl, 2-fluorobenzoyl, 3-fluorobenzoyl, 4-fluorobenzoyl, 2-chlorobenzoyl, 3-chlorobenzoyl, 4-chlorobenzoyl, 2,4-difluorobenzoyl, 2,6-difluorobenzoyl, 2,5-difluorobenzoyl, 3,4-difluorobenzoyl, 4-methylbenzoyl, 3-trifluoromethylbenzoyl, 4-trifluoromethylbenzoyl, 4-hydroxybenzoyl, 4-methoxybenzoyl, 4-bromobenzoyl, 4-phenylbenzoyl, 2-thienyl, 3-thienyl, furfuryl, 3-furylmethyl, (2-chlorothiophen-3-yl)methyl, 2-picolyl, 3-picolyl, 4-picolyl, (2-fluoropyridine-3-yl)methyl, (2-fluoropyridine-5-yl)methyl, (5-fluoropyridine-2-yl)methyl, benzyloxy, 2-phenylethoxy, methyl, ethyl, isopropyl, isopentyl, methoxy, ethoxy, isopropoxy, isopentoxy, cyclohexyl, cyclohexylmethyl, cyclohexylmethoxy, 2-(1-naphthyl)ethyl, 2-(2-naphthyl)ethyl, 4-trifluorobenzyloxy, 2,4-difluorobenzyloxy, 2-naphthylmethoxy or the like.

A more preferred example is phenyl, benzyl, 2-fluorobenzyl, 3-fluorobenzyl, 4-fluorobenzyl, 2-chlorobenzyl, 3-chlorobenzyl, 4-chlorobenzyl, 2,4-difluorobenzyl, 2,6-difluorobenzyl, 2,5-difluorobenzyl, 3,4-difluorobenzyl, 4-methylbenzyl, 3-trifluoromethylbenzyl, 4-trifluoromethylbenzyl, 4-hydroxybenzyl, 4-methoxybenzyl, 4-bromobenzyl, 4-phenylbenzyl, 2-phenylethyl, 2-(2-fluorophenyl)ethyl, 2-(3-fluorophenyl)ethyl, 2-(4-fluorophenyl)ethyl, 2-(2-chlorophenyl)ethyl, 2-(3-chlorophenyl)ethyl, 2-(4-chlorophenyl)ethyl, 2-(2,4-difluorophenyl)ethyl, 2-(2,6-difluorophenyl)ethyl, 2-(2,5-difluorophenyl)ethyl, 2-(3,4-difluorophenyl)ethyl, 2-(4-methylphenyl)ethyl, 2-(3-trifluoromethylphenyl)ethyl, 2-(4-trifluoromethylphenyl)ethyl, 2-(4-hydroxyphenyl)ethyl, 2-(4-methoxyphenyl)ethyl, 2-(4-bromophenyl)ethyl, 2-(4-bephenyl)ethyl, benzenesulfonyl, 2-fluorobenzenesulfonyl, 3-fluorobenzenesulfonyl, 4-fluorobenzenesulfonyl, 2-chlorobenzenesulfonyl, 3-chlorobenzenesulfonyl, 4-chlorobenzenesulfonyl, 2,4-difluorobenzenesulfonyl, 2,6-difluorobenzenesulfonyl, 2,5-difluorobenzenesulfonyl, 3,4-difluorobenzenesulfonyl, 4-methylbenzenesulfonyl, 3-trifluoromethylbenzenesulfonyl, 4-trifluoromethylbenzenesulfonyl, 4-hydroxybenzenesulfonyl, 4-methoxybenzenesulfonyl, 4-bromobenzenesulfonyl, 4-phenylbenzenesulfonyl, benzenesulfenyl, 4-fluorobenzenesulfenyl, phenoxy, benzyloxy, 2-phenylethoxy, methyl, ethyl, isopropyl, isopentyl, methoxy, ethoxy, isopropoxy, isopentoxy, cyclohexyl, cyclohexylmethyl, cyclohexylmethoxy, 2-(1-naphthyl)ethyl, 2-(2-naphthyl)ethyl, 4-trifluorobenzyloxy, 2,4-difluorobenzyloxy, 2-naphthylmethoxy, or the like.

A most preferred example is phenyl, benzyl, 2-phenylethyl, 2-fluorobenzyl, 3-fluorobenzyl, 4-fluorobenzyl, 2-chlorobenzyl, 3-chlorobenzyl, 4-chlorobenzyl, 2-(2-fluorophenyl)ethyl, 2-(3-fluorophenyl)ethyl, 2-(4-fluorophenyl)ethyl, benzenesulfonyl, 2-fluorobenzenesulfonyl, 3-fluorobenzenesulfonyl, 4-fluorobenzenesulfonyl, 2-chlorobenzenesulfonyl, 3-chlorobenzenesulfonyl, 4-chlorobenzenesulfonyl, benzenesulfenyl, 4-fluorobenzenesulfenyl, phenoxy, benzyloxy, 2-phenylethoxy, methyl, ethyl, isopropyl, isopentyl, methoxy, ethoxy, isopropoxy, isopentoxy, cyclohexyl, cyclohexylmethyl, cyclohexylmethoxy, 2-(1-naphthyl)ethyl, 2-(2-naphthyl)ethyl, 4-trifluorobenzyloxy, 2,4-difluorobenzyloxy, 2-naphthylmethoxy, 2-(2,4-difluorophenyl)ethyl, 2-(4-trifluoromethylphenyl)ethyl, or the like.

The compound of the formula (I) wherein Z is hydrogen may usually be at the following chemical equilibrium in a solution or the like.

cycloalkyl or optionally substituted aralkyl, or $R^4$ and $R^5$ may be taken together with the adjacent nitrogen atom to form optionally substituted non-aromatic heterocyclic group, $-S(=O)_q-R^6-R^7$ wherein $R^6$ is oxygen atom or $N-R^7$; $R^7$ each is independently hydrogen, optionally substituted alkyl, optionally substituted alkenyl, optionally substituted alkynyl or optionally substituted aralkyl; q is 1 or 2, $-S(=O)_q-R^8$ wherein $R^8$ is optionally substituted alkyl, optionally substituted alkenyl, optionally substituted alkynyl or optionally substituted aralkyl; q is as defined above, $-P(=O)(OR^9)_2$ wherein $R^9$ each is independently hydrogen or optionally substituted alkyl, halogenated alkyl or optionally substituted heteroaryl, $Z^1$ and $Z^3$ each is independently a bond, alkylene or alkenylene; $Z^2$ is a bond, alkylene, alkenylene, $-CH(OH)-$, $-S-$, $-SO-$, $-SO_2-$, $-SO_2NR^{10}-$, $-NR^{11}SO_2-$, $-O-$, $-NR^{10}-$, $-NR^{10}CO-$, $-CONR^{10}-$, $-C(=O)-O-$, $-O-C(=O)-$ or $-CO-$; $R^{10}$ is hydrogen, optionally substituted alkyl, optionally substituted alkenyl, optionally substituted alkynyl or optionally substituted aralkyl; $R^1$ is optionally substituted alkyl, optionally substituted alkenyl, optionally substituted alkynyl, optionally substituted cycloalkyl, optionally substituted cycloalkenyl, optionally substituted non-aromatic heterocyclic group, optionally substituted aryl or optionally substituted heteroaryl; p is 0 to 2, provided that when p is 2, the groups of the formula: $-Z^1-Z^2-Z^3-R^1$ may be different from each other; $R^{11}$ is hydrogen or the substituents on imino group (alkyl, alkoxyalkyl, acyl or aralkyl).

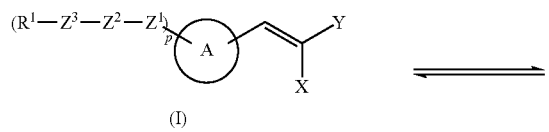

(I)

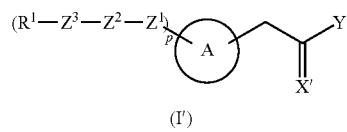

(I')

(X' = O, NR$^{11}$)

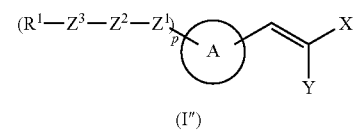

(I")

wherein A is optionally substituted aromatic heterocycle; X is hydroxy or optionally substituted amino; Y is $-C(=O-R^2)-R^3-R^4$ wherein $R^2$ is oxygen atom or sulfur atom; $R^3$ is oxygen atom, sulfur atom or $N-R^5$; $R^4$ is hydrogen, optionally substituted alkyl, optionally substituted alkenyl, optionally substituted alkynyl or optionally substituted aralkyl; $R^5$ is hydrogen, optionally substituted alkyl, optionally substituted alkenyl, optionally substituted alkynyl, optionally substituted alkoxy, optionally substituted In the chemical equilibrium shown above, the compound (I', wherein Z=O) is the ketone derivative of the compound (I, wherein X=OH), and the compound (I") and the compound (I) are cis-trans isomers with respect to the olefin part of the group of the formula: $-C(Z)=C(X)Y$. All theoretically possible tautomers and isomers of the compound (I) including these compounds are in the scope of the present invention. In the specification, the compound (I), its all tautomers and isomers may be referred to as "the compound (I)".

Though the compounds of the present invention may exist as the above tautomers upon the NMR (CDCl$_3$, d-DMSO) determination, most of them are of (I) form. Thus, most of N.M.R. data in the following examples correspond to the above-described form (I).

Furthermore, "aromatic heterocycle" or "heteroaryl" includes various tautomers. Example of triazolyl, tetrazolyl or the like are illustrated below. Therefore, triazolyl, tetrazolyl or the like is not limited to the specific structure. All tautomers are in the scope of the present invention.

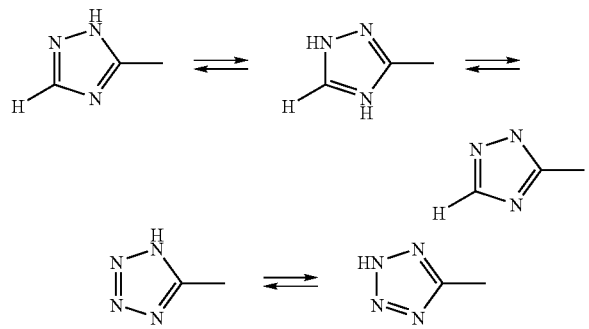

A prodrug is a derivative of the compound of the present invention (the compound of the formula (I)) having a group which can be decomposed chemically or metabolically, and such prodrug is converted to a pharmaceutically active compound of the present invention by means of solvolysis or by placing the compound in vivo under a physiological condition. Method for the selection and process of an appropriate prodrug derivative are described in the literature such as Design of Prodrugs, Elsevier, Amsterdam 1985.

HIV is known to increase in lymph node even at asymptomatic stage. Therefore, as a prodrug of the compound of the present invention, preferred is a lymph-targeted prodrug. On the other hand, AIDS brain fever is known as one of the diseases caused by HIV. Therefore, as a prodrug of the compound of the present invention, preferred is a brain-targeted prodrug.

As a lymph-targeted prodrug and a brain-targeted prodrug, preferred is a prodrug having a high lipophilicity as shown below.

When the compound of the formula (I) has a carboxyl group, an ester derivative prepared by reacting a basal acid compound with a suitable alcohol or an amide derivative prepared by reacting a basal acid compound with a suitable amine is exemplified as a prodrug. A particularly preferred ester derivative as an prodrug is methyl ester, ethyl ester, n-propyl ester, isopropyl ester, n-butyl ester, isobutyl ester, tert-butyl ester, morpholinoethyl ester, N,N-diethylglycolamido ester or the like.

When the compound of the formula (I) has a hydroxy group, an acyloxy derivative prepared by reacting with a suitable acyl halide or a suitable acid anhydride is exemplified as a prodrug. A particularly preferred acyloxy derivative as a prodrug is —O(=O)—CH$_3$, —OC(=O)—C$_2$H$_5$, —OC(=O)-(tert-Bu), —OC(=O)—C$_{15}$H$_{31}$, —OC(=O)-(m-COONa—h), —OC(=O)—CH$_2$CH$_2$COONa, —O(C=O)—CH(NH$_2$)CH$_3$, —OC(=O)—CH$_2$—N(CH$_3$)$_2$ or the like.

When the compound of the formula (I) has an amino group, an amide derivative prepared by reacting with a suitable acid halide or a suitable acid anhydride is exemplified as a prodrug. A particularly preferred amide derivative as a prodrug is —NHCO(CH$_2$)$_{20}$CH$_3$, —NHCOCH(NH$_2$)CH$_3$ or the like.

As a salt of the compound of the formula (I), any of pharmaceutically acceptable salts can be used, including base addition salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts; aryl lower alkyl amine salts such as N,N-dibenzylethylenediamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Acid addition salts include, for example, mineral acid salts such as hydrochlorides salts, sulfates salts, nitrate salts, phosphates salts, carbonates salts, hydrogen carbonates salts or perchlorates salts; organic acid salts such as acetates, propionates, lactates, maleates, fumarates, tartrates, malates, succinates, or ascorbates; sulfonates such as methanesulfonates, isethionates, benzenesulfonates, or p-toluenesulfonates; and acidic amino acid salts such as aspartates or glutamates.

Furthermore, various solvates of the compound of the formula (I), for example, monosolvate, disolvate, monohydrate, dihydrate and the like, are in the scope of the present invention.

The term "inhibit" means that the compound of the formula (I) suppresses the action of integrase.

The term "pharmaceutically acceptable" means harmless with respect to the prevention and the treatment.

The general methods for the preparation of the compound of the formula (I) (route [A] to [I]) are explained below.

A compound of the formula (I) is a novel aromatic heterocycle derivative. Examples of said aromatic heterocycle (ring (A)) include monocyclic aromatic heterocycle such as furan, thiophen, pyrrole, imidazole, pyrazole, triazole, tetrazole, oxazole, isoxazole, thiazole, thiadiazole, isothiazole, pyridine, pyridazine, pyrimidine, furazan, pyradine or the like, and polycyclic aromatic heterocycle such as benzofuran, benzothiophen, benzimidazole, dibenzofuran, benzoxazole, quinoxaline, cinnoline, quinazoline, quinoline, phthalazine, isoquinoline, purine, pteridine, carbazole, phenanthridine, acridine, indole, isoindole, phenazine or the like. Various functional groups can be introduced to these aromatic heterocycle compounds through the reaction known in the field of the aromatic compound or the specific reaction depending on each heteroaromatic ring. Heteroaromatic compounds having a desired substituent(s) can be prepared. For example, the following documents can be referred to as the general organic synthesis of various kinds of heteroaromatic compounds: (1) Alan R. Katriszly et al., Comprehensive Heterocyclic Chemistry (2) Alan R. Katriszly et al., Comprehensive Heterocyclic Chemistry II (3) RODD'S CHEMISTRY OF CARBON COMPOUNDS VOLUME IV HETEROCYCLIC COMPOUNDS and the like. The compounds of the formula (I) can be easily prepared from the commercially available heteroaromatic compounds or derivatives thereof through well-known reactions as shown below.

Introduction of the group of the formula: —C(H)=C(X)Y wherein X and Y are as defined above to the aromatic heterocycle compound can be performed in accordance with the following synthetic route [A].

Synthetic route [A]

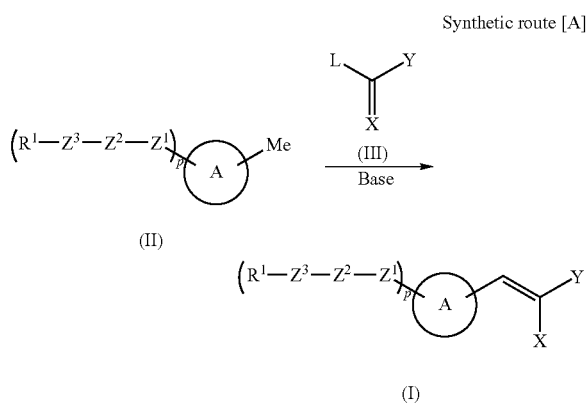

wherein ring (A) is optionally substituted aromatic heterocycle; $Z^1$ and $Z^3$ each is independently a bond, alkylene or alkenylene; $Z^2$ is a bond, alkylene, alkenylene, —CH(OH)—, —S—, —SO—, —SO$_2$—, —SO$_2$NR$^{10}$—, —NR$^{10}$SO$_2$—, —O—, —NR$^{10}$—, —NR$^{10}$CO—, —CONR$^{10}$—, —C(=O)—O—, —O—C(=O)— or —CO—; $R^1$ is optionally substituted alkyl, optionally substituted alkenyl, optionally substituted alkynyl, optionally substituted cycloalkyl, optionally substituted cycloalkenyl, optionally substituted non-aromatic heterocyclic group, optionally substituted aryl or optionally substituted heteroaryl; p is 0 to 2, provided that when p is 2, the group of the formula: —Z$^1$—Z$^2$—Z$^3$—R$^1$ may be different from each other; X is hydroxy or optionally substituted amino; Y is —C(=R$^2$)—R$^3$—R$^4$ wherein R$^2$ is oxygen atom or sulfur atom; R$^3$ is oxygen atom, sulfur atom or N—R$^5$; R$^4$ is hydrogen, optionally substituted alkyl, optionally substituted alkenyl, optionally substituted alkynyl or optionally substituted aralkyl; R$^5$ is hydrogen, optionally substituted alkyl, optionally substituted alkenyl, optionally substituted alkynyl, optionally substituted alkoxy, optionally substituted cycloalkyl or optionally substituted aralkyl, or R$^4$ and R$^5$ may be taken together with the adjacent nitrogen atom to form optionally substituted non-aromatic heterocyclic group, —S(=O)$_q$—R$^6$—R$^7$ wherein R$^6$ is oxygen atom or N—R$^7$; R$^7$ each is independently hydrogen, optionally substituted alkyl, optionally substituted alkenyl, optionally substituted alkynyl or optionally substituted aralkyl; q is 1 or 2, —S(=O)$_q$—R$^8$ wherein R$^8$ is optionally substituted alkyl, optionally substituted alkenyl, optionally substituted alkynyl or optionally substituted aralkyl; q is as defined above, —P(=O)(OR$^9$)$_2$ wherein R$^9$ each is independently hydrogen or optionally substituted alkyl, halogenated alkyl or optionally substituted heteroaryl; L is a leaving group (e.g., halogen or OR$^{12}$ wherein R$^{12}$ is alkyl or the like) or the like.

(1) Preparation of the Compound of the Formula (I) Wherein X is OH

Aromatic heterocycle derivatives having a methyl group, the compound of the formula (II), can be obtained as follows; 1) use of a commercially available compound, 2) introduction of a methyl group to aromatic heterocycle compound through Friedel-Crafts reaction.

For example, the compound of the formula (I) can be prepared by reacting the compound of the formula (II) with the compound of the formula (III), preferably in the presence of a base.

A solvent to be used is tetrahydrofuran (THF), dioxane, diethylether or the like. A base to be used is sodium ethoxide, potasium tert-butoxide, lithiumbistrimethylsilylamide (LH-MDS), butyllithium or the like. A reaction temperature is approximately −100° C. to 100° C., preferably −70° C. to 60° C.

The compound of the formula (IIIb) includes, for example, oxalic acid dimethyl ester (oxalic acid diethyl ester), methyl oxalylchloride, ethyl oxalylchloride, 2-trityl-2H-tetrazole-5-carboxylic acid ethyl ester, 1-trityl-1H-1,2,4-triazole-3-carboxylic acid ethyl ester, 1-tritylimidazole-2-carboxylic acid ethyl ester, 2-trityl-2H-tetrazole-5-carboxylic acid methyl ester, 1-trityl-1H-1,2,4-triazole-3-carboxylic acid methyl ester, 1-tritylimidazole-2-carboxylic acid methyl ester, 2-tetrahydropyranyl-2H-tetrazole-5-carboxylic acid ethyl ester, 1-tetrahydropyranyl-1H-1,2,4-triazole-3-carboxylic acid ethyl ester, 1-tetrahydropyranylimidazole-2-carboxylic acid ethyl ester, 2-tetrahydropyranyl-2H-tetrazole-5-carboxylic acid methyl ester, 1-tetrahydropyranyl-1H-1,2,4-triazole-3-carboxylic acid methyl ester, 1-tetrahydropyranylimidazole-2-carboxylic acid methyl ester, phthalic anhydride, orthomethoxybenzoylchloride, thiazole-2-carboxylic acid ethyl ester, thiazole-2-carboxylic acid methyl ester, or the like.

Example of a compound of the formula (II) includes 2-methylpyridine, 6-benzyloxy-2-methylpyridine, 5-benzyloxy-2-methylpyridine, 4-benzyloxy-2-methylpyridine, 3-benzyloxy-2-methylpyridine, 6-benzyl-2-methylpyridine, 5-benzyl-2-methylpyridine, 4-benzyl-2-methylpyridine, 3-benzyl-2-methylpyridine, 6-(2-phenyl)ethyl-2-methylpyridine, 5-(2-phenyl)ethyl-2-methylpyridine, 4-(2-phenyl)ethyl-2-methylpyridine, 3-(2-phenyl)ethyl-2-methylpyridine, 6-cyclohexylmethoxy-2-methylpyridine, 5-cyclohexylmethoxy-2-methylpyridine, 4-cyclohexylmethoxy-2-methylpyridine, 3-cyclohexylmethoxy-2-methylpyridine, 6-isopentoxy-2-methylpyridine, 5-isopentoxy-2-methylpyridine, 4-isopentoxy-2-methylpyridine, 3-isopentoxy-2-methylpyridine, 6-(2-phenyl)ethyloxy-2-methylpyridine, 5-(2-phenyl)ethyloxy-2-methylpyridine, 4-(2-phenyl)ethyloxy-2-methylpyridine, 4-benzyloxy-2-methylquinoline, 3-(2-phenyl)ethyloxy-2-methylpyridine, 5-benzyl-2-methylfuran, 2-methyl-5-(4-methylbenzyl)furan, 2-methyl-5-(4-methoxybenzyl)furan, 2-methyl-5-(4-fluorobenzyl)furan, 2-methyl-5-(4-chlorobenzyl)furan, 2-methyl-5-(3-methylbenzyl)furan, 2-methyl-5-(3-methoxybenzyl)furan, 2-methyl-5-(3-fluorobenzyl)furan, 2-methyl-5-(3-chlorobenzyl)furan, 3-methyl-1-benzyl-5-ethoxycarbonylpyrrole, 2-methyl-1-(4-fluorobenzyl)pyrrole, 3-methyl-1-(4-fluorobenzyl)pyrrole, 3-methyl-1-benzyl-5-(2-methoxycarbonylvinyl)pyrrole, 2-methyl-1-benzyl-(2-carboxyethyl)pyrrole, 3-methyl-1-benzenesulfonyl-4-(4-fluorobenzyl)pyrrole, 3-methyl-1-benzylpyrrole, 2-methyl-5-(4-fluorobenzyl)pyrrole, or the like.

A compound of the formula (I) wherein Y is —C(=R$^2$)—R$^3$—R$^4$ wherein R$^2$ is oxygen atom or sulfur atom; R$^3$ is N—R$^5$; R$^4$ is hydrogen, optionally substituted alkyl, optionally substituted alkenyl, optionally substituted alkynyl or optionally substituted aralkyl; R$^5$ is hydrogen, optionally substituted alkyl, optionally substituted alkenyl, optionally substituted alkynyl, optionally substituted alkoxy, optionally substituted cycloalkyl or optionally substituted aralkyl, or R$^4$ and R$^5$ may be taken together with the adjacent nitrogen atom to form optionally substituted non-aromatic heterocyclic group, can be prepared by reacting a compound of the formula (I) wherein Y is —C(=R$^2$)—R$^3$—R$^4$ wherein R$^2$ is oxygen atom or sulfur atom; R$^3$ is oxygen atom; R$^4$ is hydrogen with R$^4$R$^5$NH in accordance with a known peptide synthesis. For example, this reaction can be carried out in the presence of HOBt and WSCD (1-ethyl-3-(3-dimethylaminopropyl)carbodiimide hydrochloride.

A compound of the formula (I) wherein Y is —P(=O)(OR⁹)₂ wherein R⁹ each is independently hydrogen or optionally substituted alkyl can be prepared by reacting a compound of the formula (II) with phenoxycarbonylphosphonic acid diethyl ester (PhOOC—PO(OEt)₂) as a compound of the formula (III) in accordance with synthetic route [A] to prepare a compound of the formula (I) wherein Y is —P(=O)(OR⁹)₂ wherein R⁹ is ethyl, and hydrolyzing the obtained compound in the presence of trimethylsilylbromide (TMSBr) or the like.

(2) Preparation of the Compound of the Formula (I) Wherein X is Optionally Substituted Amino (NHR¹¹)

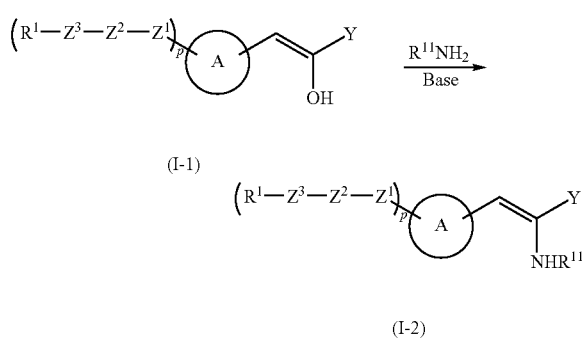

wherein A, $R^1$, $Z^1$, $Z^2$, $Z^3$, Y and p are as defined above; $R^{11}$ is alkyl, alkoxyalkyl, acyl or aralkyl.

The compound of the formula (I-2) can be prepared by reacting the compound of the formula (I-1) with a compound of the formula: $R^{11}NH_2$ wherein $R^{11}$ is alkyl (e.g., methyl, ethyl or the like), alkoxyalkyl (e.g., ethoxymethyl, ethoxyethyl or the like), acyl (e.g., formyl, acetyl or the like) or aralkyl (e.g., benzyl or the like), or its acid addition salt.

A solvent to be used is, for example, methanol, ethanol or the like. A reaction temperature is approximately −10 to 100° C., preferably room temperature to 100° C.

Introduction of a group of the formula: $-Z^1-Z^2-Z^3-R^1$ wherein $Z^1$, $Z^2$, $Z^3$ and $R^1$ each is as defined above into the aromatic heterocycle compound can be carried out in accordance with the following synthetic routes [B] to [I] or the like.

C, N and H of the ring of the formula:

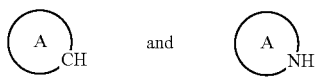

is a carbon atom of the aromatic heterocycle, a nitrogen atom of the ring and a hydrogen atom connected to these atoms, respectively.

Synthetic route [B]

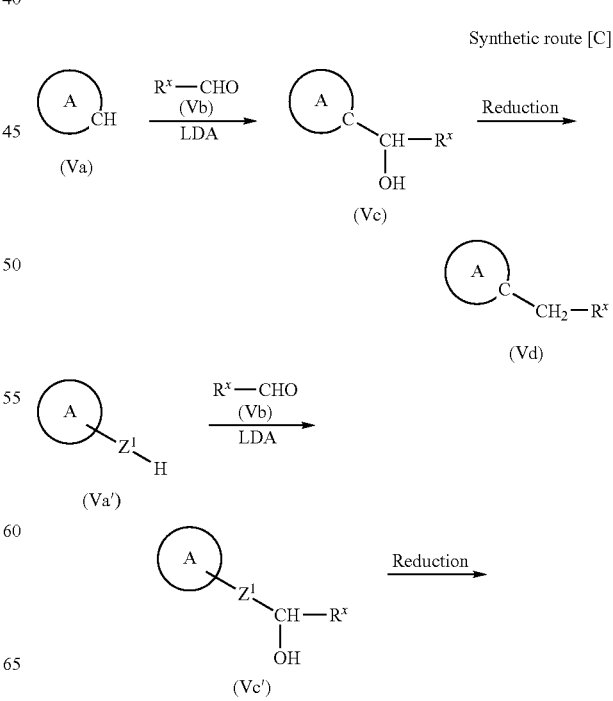

wherein A is optionally substituted aromatic heterocycle; a group of the formula: —Rx is a group of the formula: $-Z^1-Z^2-Z^3-R^1$ wherein $Z^1$ and $Z^3$ each is independently a bond, alkylene or alkenylene; $Z^2$ is a bond, alkylene, alkenylene, —CH(OH)—, —S—, —SO—, —SO₂—, —SO₂NR¹⁰—, —NR¹⁰SO₂—, —O—, —NR¹⁰—, —NR¹⁰CO—, —CONR¹⁰—, —C(=O—O)—O—, —C(=O)— or —CO—; $R^{10}$ is hydrogen, optionally substituted alkyl, optionally substituted alkenyl, optionally substituted aralkyl; $R^1$ is optionally substituted alkyl, optionally substituted alkenyl, optionally substituted alkynyl, optionally substituted cycloalkyl, optionally substituted cycloalkenyl, optionally substituted non-aromatic heterocyclic group, optionally substituted aryl or optionally substituted heteroaryl; L is a leaving group (e.g., halogen or the like).

A compound of the formula (IVc) can be prepared by reacting a compound of the formula (IVa) with a compound of the formula (IVb), or isocyanate derivative or the like which can be used for introducing a group of the formula: —Rˣ.

A base to be used is, for example, NaH, K₂CO₃ or the like. A solvent to be used is, for example, tetrahydrofuran (THF), dioxane or the like.

A compound of the formula (IVb) is, for example, various sulfonylhalides (e.g., (substituted) benzenesulfonylchloride, 2-thiophensulfonylchloride, (substituted) amino sulfonylchloride, alkylsulfonylchloride or the like), alkylhalide (e.g., methyl iodide, butyl bromide, cyclopropyl bromide or the like), aryl(lower)alkylhalide (e.g., (substituted) benzylchloride, picolylchloride, naphthylmethylchloride, biphenylmethylchloride or the like), carbamoyl chloride (e.g., dimethylcarbamoyl chloride or the like), halogenated acyl (e.g., 4-fluorobenzoylchloride or the like) or the like.

Isocyanate derivative is, for example, (substituted) arylisocyanate (e.g, phenylisocyanate or the like) or the like.

A reaction temperature is approximately −100 to 100° C., preferably −20 to 60° C.

Synthetic route [C]

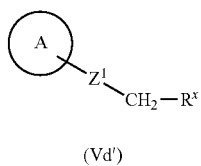

(Vd′)

wherein A is as defined above; a group of the formula: —CH(OH)—$R^X$, a group of the formula: —$CH_2$—$R^X$, a group of the formula: —$Z^1$—CH(OH)—$R^X$ and a group of the formula: —$Z^1$—$CH_2$—$R^X$ each is a group of the formula: —$Z^1$—$Z^2$—$Z^3$—$R^1$ wherein $Z^1, Z^2, Z^3$ and $R^1$ are as defined above.

A compound of the formula (Vc) or (Vc′) can be prepared by lithiation of a compound of the formula (Va) or (Va′) with a base (e.g., n-BuLi, LDA or the like), followed by reacting the above obtained compound with an aldehyde of the formula (Vb), as shown in Tetrahedron Letters, 1979, 5, p 469. LDA may be commercially available or prepared from n-BuLi and (i-Pr)$_2$NH upon the reaction.

A solvent to be used is, for example, tetrahydrofuran (THF), dioxane, diethylether or the like. A compound of the formula (Vb) is, for example, (substituted) benzaldehyde (e.g., benzaldehyde, 4-fluorobenzaldehyde, 4-chlorobenzaldehyde, 2,4-difluorobenzaldehyde, 4-trifluoromethylbenzaldehyde or the like), alkanal (e.g., formaldehyde, acetaldehyde, isovaleraldehyde or the like), furfural, 3-furaldehyde, 2-thiophenecarbaldehyde, 3-thiophenecarbaldehyde or the like. A reaction temperature is approximately –100 to 100° C., preferably –70 to 50° C.

A compound of the formula (Vd) or (Vd′) can be prepared from a compound of the formula (Vc) or (Vc′) by reduction reaction. Such reduction reaction is, for example, 1) reacting the above compound with trimethylchlorosilane and sodium iodide at –20 to 50° C. as shown in Tetrahedron, 1995, 51, p 11043, 2) reacting the above compound with phenylchlorothionoformate to produce thio ester derivative, and radically reducing the above obtained compound by tributyltin hydride and AIBN (azodiisobutyronitrile) in a solution such as toluene or the like under heating as shown in J. Org. Chem., 1993, 58, p 2552, or the like.

A ketone (e.g., a compound of the formula: $R_X$—(C═O)—Me or the like) can be used in place of an aldehyde of the formula (Vb). In such a case, a group of the formula: —C(OH)Me—$R^X$ or —CHMe—$R^X$ can be introduced into the above shown compound of the formula (Vc), (Vc′), (Vd) or (Vd′) in place of a group of the formula: —C(OH)H—$R^X$ or —$CH_2$—$R^X$.

Synthetic route [D]

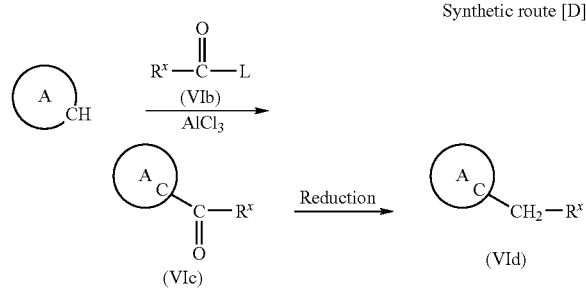

wherein A is as defined above; a group of the formula: —CO—$R^X$ and a group of the formula: —$CH_2$—$R^X$ each is a group of the formula: —$Z^1$—$Z^2$—$Z^3$—$R^1$ wherein $Z^1, Z^2, Z^3$ and $R^1$ are as defined above; L is a leaving group (e.g., halogen or —O(C═O)$R^{13}$ wherein $R^{13}$ is alkyl or the like, or the like.

A compound of the formula (VIc) can be prepared by Friedel-Crafts reaction of a compound of the formula (VIa) with a compound of the formula (VIb). In general, Friedel-Crafts reaction can be carried out in the presence of Lewis acid. A group of the formula: —(C═O)—$R^X$ can be introduced at a desired position depending on the kind of Lewis acid. For example, when $A^1$ is pyrrole, an acyl group can be introduced at the 3-position of pyrrole by using aluminum chloride and at the 2-position by using $BF_3$/ether as Lewis Acid. A compound of the formula (VIb) is, for example, acetylchloride, acetic anhydride, cyclohexylcarbonylchloride, (substituted) benzoylchloride (e.g., 4-fluorobenzoylchloride, 4-fluorobenzoylbromide, 4-chlorobenzoylchloride, 2,4-difluorobenzoylchloride, 4-trifluoromethylbenzoylchloride or the like) or the like. A solvent to be used is, for example, carbon disulfide, methylene chloride, dichloroethane or the like. A reaction temperature is approximately –100 to 100° C., preferably –50 to 50° C., more preferably –20 to 30° C.

A compound of the formula (VId) can be prepared from a compound of the formula (VIc) by reduction reaction. Such reduction reaction is, for example, 1) reacting the above compound with triethylsilane (Et$_3$SiH) as shown in J. Org. Chem., 1978, 43, p 374, 2) reducing a compound of the formula (VIc) with borane/tert-butylamine complex in the presence of aluminum chloride, or the like.

A solvent to be used is, for example, methylene chloride, ethers or the like. A reaction temperature is approximately –100 to 100° C., preferably –30 to 30° C.

Synthetic route [E]

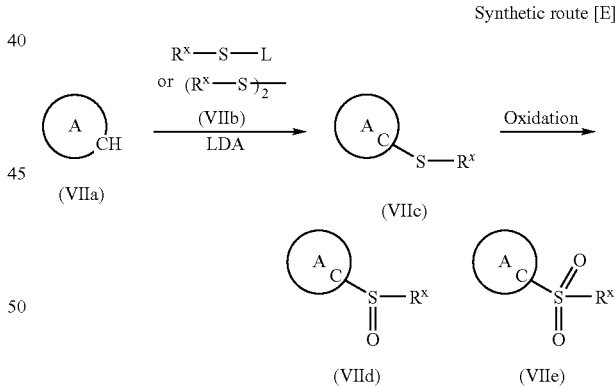

wherein A is as defined above; a group of the formula: —S—$R^X$, a group of the formula: —SO—$R^x$ and a group of the formula: —$SO_2$—$R^x$ are a group of the formula: —$Z^1$—$Z^2$—$Z^3$—$R^1$ wherein $Z^1, Z^2, Z^3$ and $R^1$ are as defined above; L is halogen or the like.

As well as synthetic route [C], a aromatic heterocycle compound is lithiated and reacted with a compound of the formula (VIIb) to give a sulfenyl derivative of the formula (VIIc). A solvent to be used is, for example, tetrahydrofuran (THF), dioxane or the like. A reaction temperature is approximately –100 to 100° C., preferably –70 to 50° C. A compound of the formula (VIIb) is disulfide (e.g., (substituted) diphenyldisulfide, dimethyldisulfide or the like), (substituted) phenylsulfenylchloride (e.g., 4-fluorophenylsulfenylchloride or the like) or the like.

Oxidation of the obtained sulfenyl derivative of the formula (VIIc) produces two types of oxide: a sulfinyl derivative of the formula (VIId) and sulfonyl derivative of the formula (VIIe). An oxidizing agent to be used is oxone, m-chloroperbenzoic acid or the like. A solvent to be used is methylene chloride, chloroform or the like. A reaction temperature is approximately −100 to 100° C., preferably −50 to 50° C., and more preferably −20 to 30° C.

Synthetic route [F]

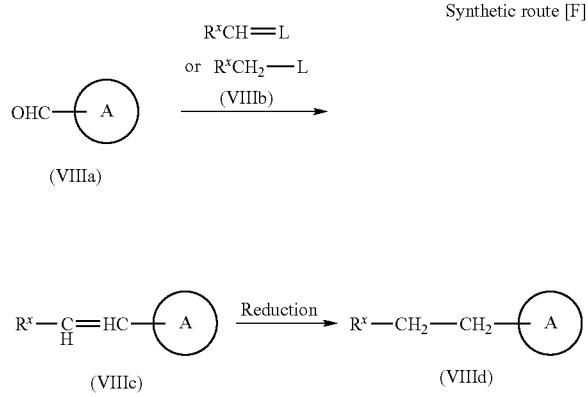

wherein A is as defined above; a group of the formula: —CH=CH—$R^X$ and a group of the formula: —$C_2H_4$—$R^X$ each is a group of the formula: —$Z^1$—$Z^2$—$Z^3$—$R^1$ wherein $Z^1$, $Z^2$, $Z^3$ and $R^1$ are as defined above; L is —P(=O—O)(OEt)$_2$, =PPh$_3$ or the like.

A aromatic heterocycle derivative having a formyl group, shown of the formula (VIIIa), can be obtained as follows: 1) use of a commercially available compound or 2) introduction of a formyl group to aromatic heterocycle compound through Vilsmeier reaction, Reimer-Tiemann reaction or the like.

An olefin derivative of the formula (VIIIc) can be prepared by Wittig reaction or Horner-Emmons reaction of a compound of the formula (VIIIa) with a compound of the formula (VIIIb), if desired, in the presence of a base.

A compound of the formula (VIIIb) is, for example, an ylide derivative (e.g., (carbethoxy)triphenylphospholan or the like), phosphoryl derivative (e.g., methyl diethylphosphono acetate, diethylbenzyl phosphonate or the like) or the like. A solvent to be used is, for example, dimethylformamide (DMF), tetrahydrofuran (THF), dioxane or the like. A reaction temperature is approximately −100 to 150° C., preferably −20 to 100° C.

A compound of the formula (VIIId) can be prepared by reducing an olefin derivative of the formula (VIIIc). Hydrogenation or the like can be used as reduction reaction. A catalyst to be used is, for example, palladium-carbon or the like. A solvent to be used is, for example, tetrahydrofuran (THF), ethanol or the like, preferably mixed solvent with ethanol and tetrahydrofuran. A reaction temperature is approximately −100 to 100° C., preferably −20 to 30° C.

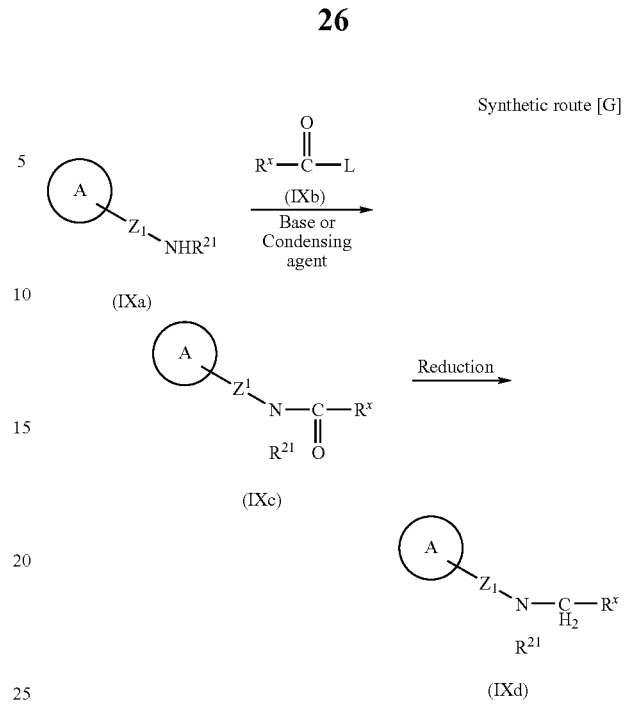

Synthetic route [G]

wherein A and $Z^1$ are as defined above; a group of the formula: —$R^X$ and a group of the formula: —$CH_2$—$R^X$ each is a group of the formula: —$Z^3$—$R^1$ wherein $Z^3$ and $R^1$ are as defined above; L is a leaving group (e.g., halogen, hydroxy, —O(C=O)$R^{14}$ wherein $R^{14}$ is alkyl or the like) or the like.

A compound of the formula (I) wherein $Z^2$ is —$NR^{10}$CO— or —$NR^{10}$— wherein $R^{10}$ is as defined above can be prepared as illustrated above.

A aromatic heterocycle derivative having an amino group of the formula (IXa), is easily prepared by 1) obtaining a commercially available compound, 2) reacting the corresponding halogen derivative with $R^{10}NH_2$, or 3) reducing a nitro derivative prepared by nitration.

For example, a compound of the formula (IXc) can be prepared by reacting a compound of the formula (IXa) with a compound of the formula (IXb), preferably in the presence of a base, as shown in shin-jikkenn kagakukouza, Vol. 14, 1978, page 1787; Synthesis, 1986, p 852-854; shin-jikkenn kagakukouza, Vol. 22, 1992, page 155. When a compound of the formula (IXb) is a carboxylic acid, a compound of the formula (IXc) can be prepared by condensation reaction using a condensing agent.

A solvent to be used is, for example, tetrahydrofuran (THF), dioxane or the like. A base to be used is, for example, pyridine, dimethylamino pyridine or the like. A condensing agent to be used is, for example, DCC (dicyclohexylcarbodiimide), EDC or the like. A reaction temperature is approximately −100 to 100° C., preferably −70 to 60° C.

A compound of the formula (IXd) can be prepared by reducing a compound of the formula (XIIc). Reduction reaction is carried out by using lithium aluminum hydride, borane methylsulfide complex or the like.

In the above shown synthetic route [G], a sulfonamide derivative of the formula (I) wherein $Z^2$ is —$NR^{10}SO_2$—, can be prepared by using a compound of the formula: $R^X(SO_2)L$ wherein Rx is as defined above and L is halogen or the like in place of a compound of the formula: $R^X(C=O)L$. When an aromatic heterocycle compound having a carboxy group or the like, shown as a compound of the formula (IXa) wherein a group of the formula: —$NHR^{10}$ is a group of the formula:

—COL wherein L is a leaving group (e.g., halogen, hydroxy, —O(C=O)R$^{14}$ wherein R$^{14}$ is lower alkyl or the like, or the like, can be obtained or prepared as a starting material, an amide derivative of the formula (I) wherein Z$^2$ is —CONR$^{10}$—, can be prepared by condensation reaction using a compound of the formula: R$^X$NH$_2$ in place of a compound of the (IXb) as well as the above shown synthetic route [G]. On the other hand, when an aromatic heterocycle compound having a group of the formula: —(SO$_2$)L wherein L is halogen or the like can be obtained or prepared as a starting material, an sulfonamide derivative of the formula (I) wherein Z$^2$ is —SO$_2$NR$^{10}$—, can be prepared by using a compound of the formula: R$^X$NH$_2$.

Synthetic route [H]

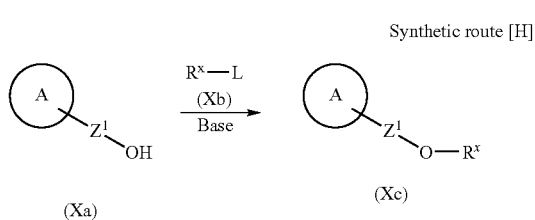

(Xa)  (Xc)

wherein A and Z$^1$ are as defined above; L is halogen; a group of the formula: —R$^X$ is a group of the formula: —Z$^3$—R$^1$ wherein Z$^3$ and R$^1$ are as defined above.

A compound of the formula (I) wherein Z$^2$ is —O— can be prepared as illustrated above.

Examples of a compound of the formula (Xa) include 6-hydroxy-2-methylpyridine, 5-hydroxy-2-methylpyridine, 4-hydroxy-2-methylpyridine, 3-hydroxy-2-methylpyridine, 8-hydroxy-2-methylquinoline, 7-hydroxy-2-methylquinoline, 6-hydroxy-2-methylquinoline, 5-hydroxy-2-methylquinoline, 4-hydroxy-2-methylquinoline, 3-hydroxy-2-methylquinoline, 8-hydroxy-1-methylisoquinoline, 7-hydroxy-1-methylisoquinoline, 6-hydroxy-1-methylisoquinoline, 5-hydroxy-1-methylisoquinoline, 4-hydroxy-1-methylisoquinoline, 3-hydroxy-1-methylisoquinoline, 8-hydroxy-3-methylisoquinoline, 7-hydroxy-3-methylisoquinoline, 6-hydroxy-3-methylisoquinoline, 5-hydroxy-3-methylisoquinoline, 4-hydroxy-3-methylisoquinoline, 1-hydroxy-3-methylisoquinoline, 3-hydroxy-2-methylpyrazine, 5-hydroxy-2-methylpyrazine, 6-hydroxy-2-methyl or the like.

A base to be used is, for example, NaH, NaOH, LiH, CaCO$_3$, K$_2$CO$_3$ or the like.

A reaction temperature is room temperature to 100° C. A solvent to be used is, for example, DMF or the like.

Examples of a compound of the formula (Xb) include, for example, benzylbromide, benzylchloride, cyclohexylmethylbromide, cyclohexylmethylchloride, isopentylchloride, isopentylbromide, 2-phenylethylchloride, 4-fluorobenzylchloride, 4-fluorobenzylbromide, 2-(4-fluorophenyl)ethylchloride, 2,4-difluorobenzylchloride, 2,4-difluorobenzylbromide, isopropylchloride, isopropylbromide, methyl iodide, 4-trifluoromethylbenzylchloride, 4-trifluoromethylbenzylbromide, 2-naphthylmethylchloride, 2-naphthylmethylbromide, 3,5-difluorobenzylchloride, 3,5-difluorobenzylbromide or the like.

When an aromatic heterocycle ring (A$^1$) has a group of the formula: —Z$^1$—SH wherein R$^X$ is as defined above, a compound of the formula (I) wherein Z$^2$ is —S— can be prepared by using a compound of the formula (Xb).

When an aromatic heterocycle ring (A$^1$) has a group of the formula: —Z$^1$—L wherein Z$^1$ is as defined above and L is halogen or the like, a compound of the formula (Xc) can be prepared by using a compound of the formula: R$^X$—OH wherein R$^X$ is as defined above in place of a compound of the formula (Xb).

Synthetic Route [I]

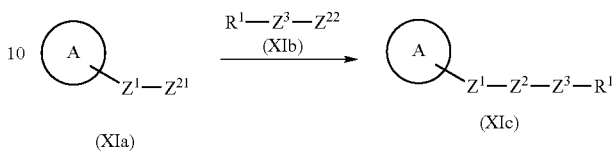

wherein A, Z$^1$, Z$^2$, Z$^3$ and R$^1$ are as defined above; Z$^{21}$, Z$^{22}$, Z$^{41}$ and Z$^{42}$ each is independently —CHO, —CH$_2$Li, —SH, —SO$_2$L, —MgL, —Li, —NHR$^{10}$, —OH, —L, —COOH, —COL, —B(OH)$_2$, —Otf or the like; L is halogen or the like.

Whereas the above shown synthetic routes [B] to [H] mainly relate to direct insertion of a substituent(s) into the aromatic heterocycle, this synthetic route [I] can provide a compound of the formula (XIc) by further reacting a functional group attached to the aromatic heterocycle (e.g, a group of the formula: —Z$^1$—Z$^{21}$).

For example, a combination of Z$^{21}$ and Z$^{22}$ forms Z$^2$ as shown below (—Z$^{21}$+—Z$^{22}$→Z$^2$—).

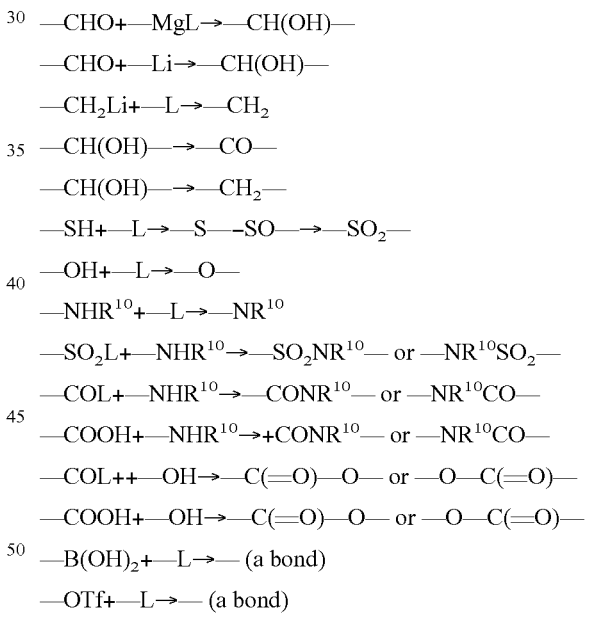

These reactions are well known in organic chemistry and can be performed in accordance with an usual public method and condition such as reaction temperature, solvent or the like.

The procedure of the above-shown reactions [A] to [I] can be modified according to the character of aromatic heterocycle derivative, the introduction position of the substituent or the like. Protection of functional groups and the deprotection, if desired, may be performed in accordance with a well known method. The example includes protection of carbonyl group with acetal, protection of carboxylic acid with ester residue or the like.

In preparation of the compound of the present invention, the following solid phase synthesis can be carried out.

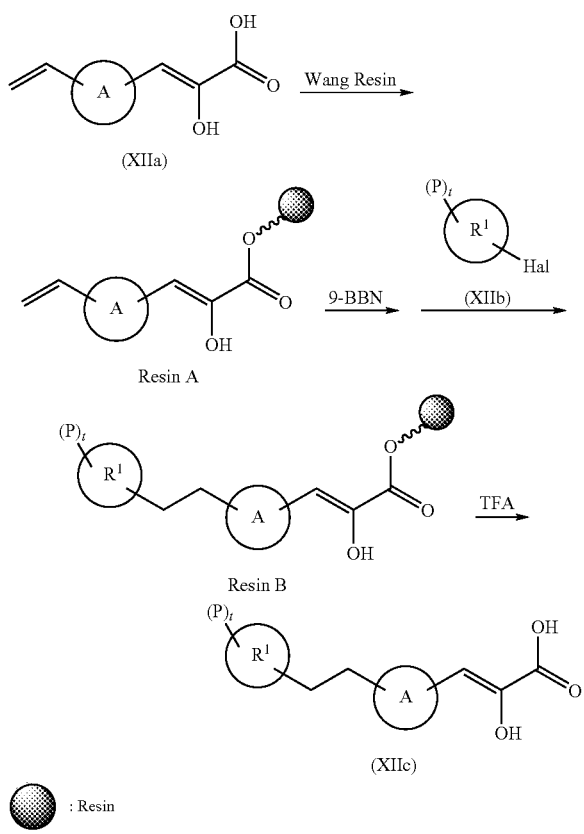

wherein Hal is halogen; ring (A) is optionally substituted aromatic heterocycle; $R^1$ is heteroaryl or aryl; P is hydroxy, carboxy, halogen, halogenated alkyl, alkyl, alkenyl, alkynyl, cycloalkyl, cycloalkenyl, alkoxy, alkoxycarbonyl, nitro, nitroso, optionally substituted amino, azido, aryl, aralkyl, cyano, isocyano, isocyanato, thiocyanato, isothiocyanato, mercapto, alkylthio, alkylsulfonyl, optionally substituted carbamoyl, sulfamoyl, acyl, formyloxy, haloformyl, oxalo, mercapto, thioformyl, thiocarboxy, dithiocarboxy, thiocarbamoyl, sulfino, sulfo, sulfoamino, hydrazino, azido, ureido, amidino or guanidino; t is 0 to 5.

First of all, a compound of the formula (XIIa) is attached to a resin (e.g., Wang Resin), which can be carried out in DMF in the presence of HOBt, N-methylmorpholine and PyBop. The obtained resin is washed with DMF, water, methanol and/or methylene chloride and dried under reduced pressure, to give Resin A.

Next, a mixture of Resin A and THF is stirred at room temperature in the presence of 9-BBN. To the mixture is added an aqueous solution of potassium carbonate. To the mixture are added a compound of the formula (XIIb) and $PdCl_2$ (dppf). The mixture is stirred at approximately 50° C. for several hours to several ten hours. The obtained resin is washed with DMF, water, methanol and/or methylene chloride to give Resin B.

The compounds of the formula (XIIb) are prepared from commercially available compounds or prepared by synthesis. This process is useful because this process is one of solid phase syntheses, in which purification procedure is a washing resins, most procedures can be carried out as a routine step, and many compounds can be prepared for short term. Therefore, compounds of the formula (XIIb) having many kinds of substituents can be used for this process.

Finally, the obtained Resin B is treated with an acidic solution (e.g., TFA-methylene chloride) to give a compound of the formula (XIIc). The compounds obtained by this process can be used as well as that prepared by usual liquid phase synthesis, because the number of steps in this process is small and the purity of them is high.

This solid phase synthesis can be carried out, not depending on any kind of ring (A), $R^1$, the substituent P, the number (t) of the substituents. A preferred ring (A) is pyridine or pyrimidine. A preferred $R^1$ is aryl (especially phenyl).

This solid phase synthesis gives, for example, compounds of the formula (XIIc) having various substituents on $R^1$ by using pyridine or pyrimidine as ring (A) and reacting various kinds of a compound of the formula (XIIb).

A library of the compound of the formula (XIIc) can be prepared by this process. Split synthesis or parallel synthesis may be used. The term "a library of compounds" means a group of compounds, having the common partial structure, prepared from a solid phase synthesis. With respect to compounds of the formula (XIIc), the common partial structure is that a group of the formula: —C(H)=C(OH)COOH substitutes on ring (A) and that ring (A) bonds to $R^1$ via a group of the formula: —$C_2H_4$—. Compounds having such common partial structures have an anti-integrase inhibitory activity. A pharmaceutical composition thereof can be used as an antiviral agent, an anti-HIV agent, an integrase inhibitor or a HIV medical mixture.

The library of compounds of the present invention can be used not only for screening integrase inhibitors having a high integrase inhibitory activity, but also for screening compounds having the other medical use.

Method for use of the compound of the present invention is explained below.

The compound of the formula (I) is useful as a pharmaceutical composition such as an antiviral agent or the like. The compound of the present invention has an outstanding inhibitory activity against integrase of viruses. Therefore, the compound of the formula (I) is expected to prevent or treat various diseases caused by viruses producing integrase to grow in animal cells upon infection, and is useful as, for example, an integrase inhibitor against retroviruses (e.g., HIV-1, HIV-2, HTLV-1, SIV, FIV or the like), especially, an anti-HIV agent or the like.

The compound of the formula (I) can be used in combination therapy, by the combination with an anti-HIV agent possessing other inhibitory mechanism such as a reverse transcriptase inhibitor and/or a protease inhibitor. Since any integrase inhibitor has not been on sale yet, it is useful to use the compound of the formula (I) in combination therapy, associated with a reverse transcriptase inhibitor and/or a protease inhibitor.

Besides use for an anti-HIV medical mixture, the compound of the present invention can be used in cocktail therapy or the like as a concomitant agent showing synergy effect, such as enhancing the activity of the other anti-HIV agent.

The compound of the formula (I) can be used to suppress the spread of the retrovirus infection over non-target tissues in the gene therapy using a retrovirus vector derived from HIV or MLV. Specially, in the case that cells and the like are infected by such a vector in vitro and then are put back in a body, a previous administration of the compound of the formula (I) prevents an unnecessary infection.

The compounds of the formula (I) can be administered orally or parenterally. For oral administration, the compounds of the present invention can be used in any form of usual formulations, for example, solid formulations such as tablets, powders, granules, capsules; aqueous formulations; oleaginous suspensions; solutions such as syrup or elixir. For parenteral administration, the compounds of the formula (I) can be used as an aqueous or oleaginous suspension injection, or nose drops. In the preparation of such formulations, conventional excipients, binding agents, lubricants, aqueous solvents, oleaginous solvents, emulsifying agents, suspending agents, preservatives, stabilizers, and the like can be optionally used. Preferred as an anti-HIV agent is oral administration.

A formulation according to the present invention may be manufactured by combining (for example, admixing) a curatively effective amount of a compound of the formula (I) with a pharmaceutically acceptable carrier or diluent. The formulation comprising a compound of the formula (I) may be manufactured with the use of well-known and easily available ingredients in accordance with a known method.

In the case of manufacturing a pharmaceutical composition comprising a compound of the formula (I), an active ingredient is admixed or diluted with a carrier, or they are contained in a carrier in the form of capsule, sacheier, paper, or another container. In the case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to formulate a compound of the present invention prior to administration.

Any suitable carrier which has been well known by those skilled in the art may be used for the formulation. In such formulation, a carrier is in the form of solid, liquid, or a mixture of solid and liquid. For instance, a compound of the present invention is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. Example of suitable solid carriers include magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

Although an appropriate dosage of the compound of the formula (I) varies depending on the administration route, age, body weight, conditions of the patient, and kind of disease, in the case of oral administration, the daily dosage can be between approximately 0.05-3000 mg, preferably approximately 0.1-1000 mg, for an adult. The daily dosage can be administered in divisions. In the case of parenteral administration, the daily dosage for an adult can be between approximately 0.01-1000 mg, preferably approximately 0.05-500 mg.

Furthermore, all kinds of heteroaromatic derivatives having the group of the formula: —C(Z)=C(X)Y wherein X, Y and Z are as defined above can be used as pharmaceutical compositions such as antiviral agents, as well as the compound of the formula (I). In said heteroaromatic derivatives, a wide variety of substituents can be introduced as partial structures other than —C(Z)=C(X)Y, as far as they do not have a negative effect on the pharmacological activity. These compounds can be prepared in accordance with the above preparations of the compound of the present invention.

The compound of the formula (I) is useful as an intermediate or a starting material for preparing medicines or the like. For example, the compound of the present invention wherein R defined in Y is an ester residue can be easily derived to the compound wherein R is hydrogen by deprotection.

EXAMPLE

Examples of the present invention are shown below. Reactions are usually carried out under nitrogen atmosphere, and reaction solvents are used as dried over molecular sieve and the like. Extracts are dried over sodium sulfate or magnesium sulfate and the like.

(Agent)

n-butyllithium=1.5 mol/l hexane solution sodium hydride 60% oil suspension (Abbreviation)

Et=ethyl; MeOH=methanol; EtOH=ethanol; DMF=N,N-dimethylformamide; THF=tetrahydrofuran; DMSO=dimethylsulfoxide; HOBt=1-hydroxybenzotriazole; WSCD=1-ethyl-3-(3-dimethylaminopropyl) carbodiimide hydrochloride

Reference Example

2-Trityl-2H-tetrazol-5-carboxylic acid ethyl ester, 1-trityl-1H-1,2,4-triazol-3-carboxylic acid ethyl ester and 2-trityl-2H-1,2,4-triazol-3-carboxylic acid ethyl ester to be used in the present invention were prepared in accordance with methods (A) to (C) described below. Additionally, 1-trityl-1H-1,2,4-triazol-3-carboxylic acid ethyl ester and 2-trityl-2H-1,2,4-triazol-3-carboxylic acid ethyl ester have a protective group (trityl) at different position, but both of them can be used in the preparation of the compound of the formula (I) and (II).

(A) 2-Trityl-2H-tetrazol-5-carboxylic Acid Ethyl Ester (1) To a solution of trimethyltinazide (6.17 g, 30 mmol) in pyridine (20 ml) was added dropwise ethyl cyanoformate (3.30 g, 33 mmol) for 15 minutes at room temperature. The temperature of the reaction solution became approximately 45° C. The reaction mixture was gradually cooled down to room temperature and stirred for 1 hour, heated at 60° C. and then stirred for 18 hours. After cooling, the reaction mixture was concentrated under reduced pressure. To the residue was added concentrated hydrochloric acid (5 ml). After stirring for 15 minutes at room temperature, saturated brine (20 ml) was added thereto. The mixture was twice extracted with ethyl acetate, washed with saturated brine and dried. The solvent was evaporated. The obtained crystal was washed with hexane to give 1H-tetrazol-5-carboxylic acid ethyl ester (3.47 g). Yield: 81%.

(2) To a solution of 1H-tetrazol-5-carboxylic acid ethyl ester (3.47 g, 24.4 mmol) in THF (20 ml) were added triethylamine (3.70 g, 36.6 mmol) and tritylchloride (7.14 g, 25.6 mmol) successively. The reaction mixture was stirred for 1 hour at room temperature and concentrated under reduced pressure. The residue was partitioned between ethyl acetate and water. The ethyl acetate layer was washed with an aqueous saturated sodium bicarbonate, washed with water and dried. The solvent was evaporated. The obtained crystal was washed with hexane to give the titled compound (8.15 g). Yield: 87%.

M.p.: 162° C. (decomposition)
NMR (CDCl$_3$) δ: 1.43 (3H, t, J=7.2 Hz), 4.50 (2H, q, J=7.2 Hz), 7.08-7.12 (6H, m), 7.29-7.41 (9H, m).

(B) 1-Trityl-1H-1,2,4-triazol-3-carboxylic Acid Ethyl Ester (1) A mixture of ethyl thioxamate (10.55 g, 79.2 mmol) and formylhydrazine (5.00 g, 83.2 mmol) was heated at 65° C. for 30 minutes and stirred in accordance with a method described in Collect. Czech Chem. Commun., 1984, 49, p 2492. After cooling, the precipitated crystal was collected by filteration and washed with ethanol to give (N-formylhydrazino)-imino acetic acid ethyl ester (9.62 g). Yield: 76%.

(2) A suspension of (N-Formylhydrazino)-imino acetic acid ethyl ester (9.62 g, 60.4 mmol) in diglyme (40 ml) was refluxed for 30 minutes. After cooling, the precipitated crystal was collected by filteration and washed with hexane to give 1H-1,2,4-triazol-3-carboxylic acid ethyl ester (7.28 g). Yield: 85%.

(3) To a solution of 1H-1,2,4-triazol-3-carboxylic acid ethyl ester (7.62 g, 54 mmol) in DMF (60 ml) was added at room temperature N,N-diisopropylethylamine (14 g, 108 mmol) and tritylchloride (15.8 g, 56.7 mmol), successively. The mixture was stirred for 2 hours. The reaction mixture was mixed with water (300 ml) and ethyl acetate (300 ml). The crystal was collected by filteration, dissolved in CHCl$_3$ (150 ml), washed with water and dried. The solvent was evaporated. The residue was crystallized from ether to give the titled compound (8.91 g). Additionally, ethyl acetate layer was washed with water and dried. The solvent was evaporated. The residue was crystallized from ether to give the titled compound (4.73 g). Total amount of the titled compound: 13.64 g. Yield: 66%.

NMR (CDCl$_3$) δ: 1.41 (3H, t, J=7.2 Hz), 4.45 (2H, q, J=7.2 Hz), 7.11-7.13 (6H, m), 7.32-7.36 (9H, m), 8.01 (1H, s).

(C) 2-Trityl-2H-1,2,4-triazol-3-carboxylic Acid Ethyl Ester (1) Sodium hydride (60% dispersion in mineral oil, 13.8 g, 345 mmol) was washed with hexane and suspended in DMF (150 ml). At an ice bath temperature, 1,2,4-triazole (total; 20.7 g, 300 mmol) was added thereto in four divisions. After stirring for 30 minutes, to the mixture was added tritylchloride (total; 83.7 g, 300 mmol) in seven divisions and additionally added DMF (50 ml). After stirring for 1.5 hours at room temperature, to the reaction mixture was added water (600 ml). The precipitated crystal was collected by filteration, washed with water, dissolved in CHCl$_3$ (800 ml) and dried. The solvent was evaporated. The obtained residue was chromatographed on silica gel (ethyl acetate:CHCl$_3$=1:2, v/v). The fraction of the objective was concentrated to give 1-trityl-1H-1,2,4-triazole (43.9 g). Yield: 47%.

(2) A solution of 1-Trityl-1H-1,2,4-triazole (10.5 g, 33.6 mmol) in THF (300 ml) was cooled under −70° C. To the solution was added at −72 to −68° C. a solution of n-butyllithium in hexane (1.54 M solution, 24 ml, 36.9 mmol). The reaction solution was gradually warmed up to −25° C. and cooled down to −60° C. again. To the mixture was added dropwise a solution of chloroethylformate (7.29 g, 67.2 mmol) in THF (15 ml). The reaction mixture was warmed up to room temperature, stirred for 1.5 hours, concentrated under reduced pressure and mixed with ethyl acetate (700 ml). The precipitated crystal was collected by filteration, washed with water, dissolved in THF (200 ml) and dried. The solvent was evaporated. The obtained crystal was washed with ethyl acetate to give the titled compound (2.90 g). The ethyl acetate layer was washed with 2% aqueous ammonia, washed with water and dried. The solvent was evaporated. The obtained residue was chromatographed on silica gel (hexane:ethyl acetate: CHCl$_3$=2:1:2, v/v/v) to give the titled compound (3.65 g). Total of the titled compound: 6.55 g. Yield: 51%.

NMR (CDCl$_3$) δ: 1.02 (3H, t, J=7.2 Hz), 3.76 (2H, q, J=7.2 Hz), 7.12-7.14 (6H, m), 7.28-7.33 (9H, m), 7.99 (1H, s).

Example 1

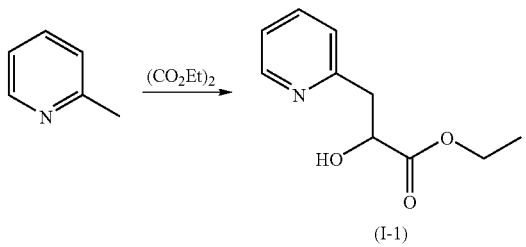

(I-1)

To a solution of 2-methylpyridine (466 mg, 5 mmol) in THF (10 ml) was added dropwise at −78° C. n-butyllithium (5 mmol). To the solution was added oxalic acid diethyl ester (7.3 g, 50 mmol). The mixture was stirred for 30 minutes. To the mixture was added an aqueous solution of ammonium chloride. The mixture was extracted with ethyl acetate, washed with water, dried and concentrated. The obtained residue was chromatographed on silica gel (n-hexane-ethyl acetate) to give compound (1-1) (504 mg).

¹H-NMR (CDCl₃) δ: 1.40 (3H, t, J=7.1 Hz), 4.38 (2H, q, J=7.1), 6.55 (1H, s), 7.14-7.24 (2H, m).

Example 2 and 3

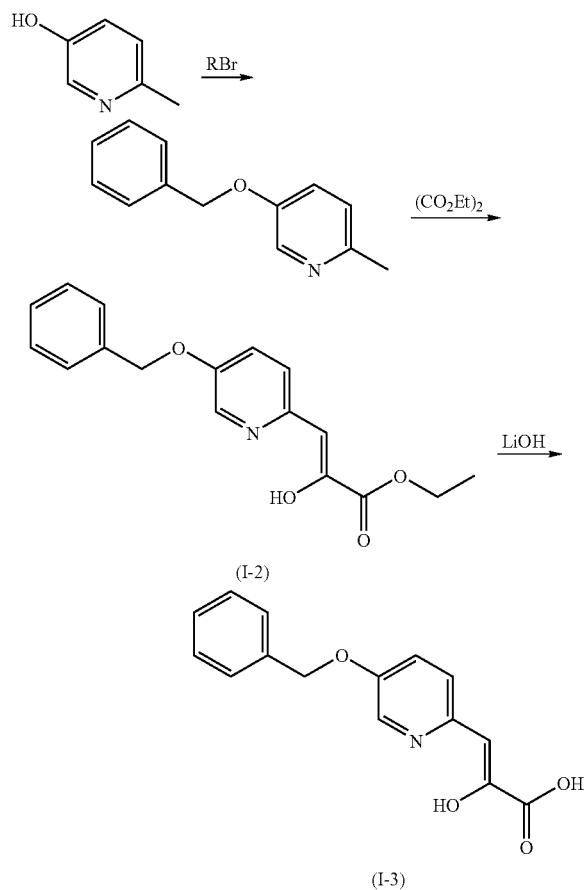

To a solution of 5-hydroxy-2-methylpyridine (2.18 g, 20 mmol) in DMF (15 ml) were added under ice-cooling benzylbromide (4.00 g, 24 mmol) and calcium carbonate (3.30 g, 24 mmol). The reaction mixture was stirred at room temperature for 2 hours. To the reaction mixture was added an aqueous solution of ammonium chloride. The mixture was extracted with diethyl ether, washed with water, dried and concentrated. The obtained residue was chromatographed on silica gel (n-hexane-ethyl acetate) to give 5-benzyloxy-2-methylpyridine (2.04 g).

To a solution of 5-benzyloxy-2-methylpyridine (598 mg, 3 mmol) in THF (20 ml) was added dropwise at −78° C. n-butyllithium (3 mmol). To the solution was added oxalic acid diethyl ester (4.5 g, 30 mmol). The solution was stirred for 30 minutes. To the reaction mixture was added an aqueous solution of ammonium chloride. The solution was extracted with ethyl acetate, washed with water, dried and concentrated. The obtained residue was chromatographed on silica gel (n-hexane-ethyl acetate). The fraction was concentrated. The obtained crystal was washed with diethyl ether, dried under reduced pressure to give compound (I-2) (101 mg).

¹H-NMR (CDCl₃) δ: 1.39 (3H, t, J=7.0 Hz), 4.35 (2H, q, J=7.0 Hz), 5.14 (2H, s), 6.58 (1H, s), 7.18-7.43 (7H, m), 8.24 (1H, d, J=2.4 Hz).

To a solution of compound (I-2) (71 mg, 0.24 mmol) in methanol was added an aqueous solution of lithium hydroxide (1N, 0.29 ml). The mixture was stirred at room temperature for 6 hours. Methanol was removed under reduced pressure and mixed with water. A solution was acidified with citric acid. The mixture was extracted with ethyl acetate, washed with water, dried and concentrated under reduced pressure. The obtained crystal was washed with diethyl ether and dried under reduced pressure to give compound (I-3) (30 mg).

¹H-NMR (d₆-DMSO) δ: 5.23 (2H, s), 6.66 (1H, s), 7.30-7.65 (7H, m), 8.38 (1H, d, J=3.3 Hz).

Example 4-12

Example 4-12 each is carried out in accordance with Example 1-3. Each structure and physical date of the compound is shown below.

TABLE 1

| Comp. No. | Structure | ¹H-NMR |
|---|---|---|
| I-4 | (structure shown) | (CDCl₃) δ: 1.39(3H,t,J=7.2 Hz), 4.36(2H,q,J=7.2 Hz), 5.16(2H,s), 7.03(1H,s), 7.08(1H,dd,J=8.2,5.0 Hz), 7.21(1H,dd,J=8.2,1.2 Hz), 7.31-7.46(5H,m), 8.01(1H,dd,J=5.0,1.2 Hz). |

TABLE 1-continued

| Comp. No. | Structure | ¹H-NMR |
|---|---|---|
| I-5 | 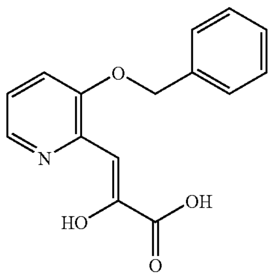 | (d$_6$-DMSO) δ: 5.25(2H,s), 6.74(1H,s), 7.28-7.52(6H,m), 7.64(1H,dd,J=8.5, 1.1 Hz), 8.12(1H,dd,J=5.1,1.1 Hz). |
| I-6 | 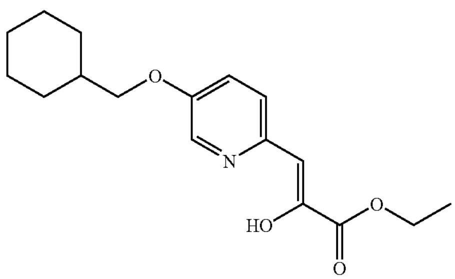 | (CDCl$_3$) δ: 1.00-1.92(11H,m), 1.40(3H, t,J=7.0 Hz), 3.82(2H,d,J=6.5 Hz), 4.35(2H,q,J=7.0 Hz), 6.55(1H,s), 7.16(1H,d,J=7.8 Hz), 7.24(1H,dd, J=7.8,3.3 Hz), 8.16(1H,d,J=3.3 Hz). |
| I-7 | 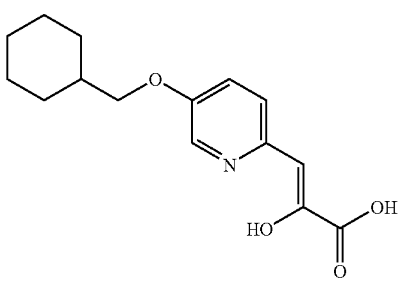 | (d$_6$-DMSO) δ: 0.95-1.85(11H,m), 3.91(2H,d,J=6.2 Hz), 6.56(1H,s), 7.49(1H,d,J=9.1 Hz), 7.54(1H,dd, J=9.1,2.5 Hz), 8.30(1H,d,J=2.5 Hz). |
| I-8 | 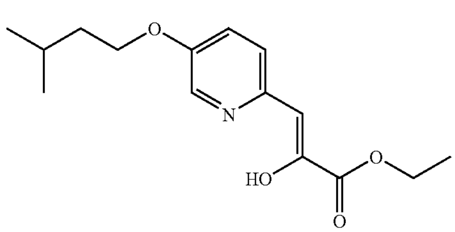 | (CDCl$_3$) δ: 0.98(6H,d,J=6.4 Hz), 1.39(3H,t,J=7.0 Hz), 1.71(2H,q, J=6.6 Hz), 1.76-1.92(1H,m), 4.06(2H, t,J=6.5 Hz), 4.36(2H,q,J=7.0 Hz), 6.58(1H,s), 7.20(1H,d,J=8.5 Hz), 7.28(1H,dd,J=8.5,3.4 Hz), 8.16(1H,d, J=3.4 Hz). |

TABLE 1-continued
| Comp. No. | Structure | ¹H-NMR |
|---|---|---|
| I-9 | 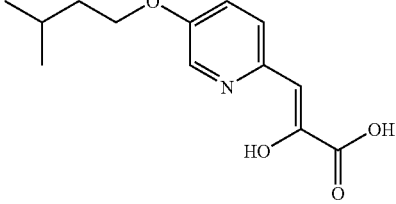 | (d₆-DMSO) δ: 0.94(6H,d,J=6.4 Hz), 1.67(2H,q,J=6.6 Hz), 1.70-1.85(1H,m), 4.11(2H,t,J=6.6 Hz), 6.56(1H,s), 7.50(1H,d,J=9.3 Hz), 7.55(1H,dd,J=9.3,3.3 Hz), 8.31(1H,d,J=3.3 Hz). |
| I-10 | 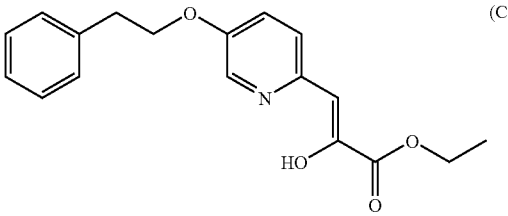 | (CDCl₃) δ: 1.38(3H,t,J7.1 Hz), 3.12(2H,t,J=6.9 Hz), 4.25(2H,t,J=6.9 Hz), 4.35(2H,q,J=7.1 Hz), 6.55(1H,s), 7.17(1H,d,J=9.0 Hz), 7.20-7.40(6H,m), 8.16(1H,d,J=2.7 Hz). |
| I-11 | 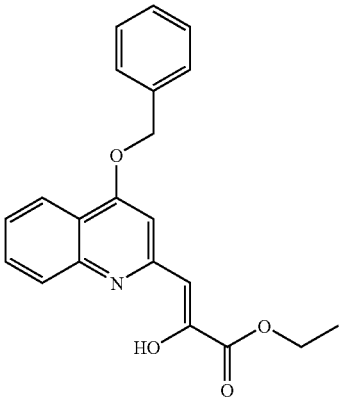 | (CDCl₃) δ: 1.20(3H,t,J=7.6Hz), 4.35(2H,q,J=7.6 Hz), 5.30(2H,s), 6.36(1H,s), 6.46(1H,s), 7.35-7.70(8H,m), 8.10(1H,d,J=7.3 Hz). |
| I-12 | 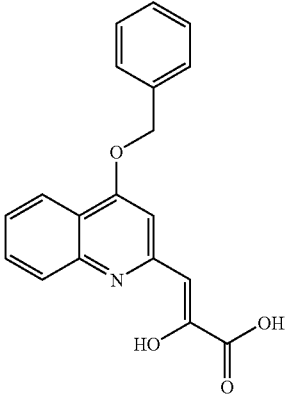 | (d₆-DMSO) δ: 5.40(2H,s), 6.26(1H,s), 7.10-6.95(1H, brom), 7.35-8.05(9H,m). |

Example 13, 14

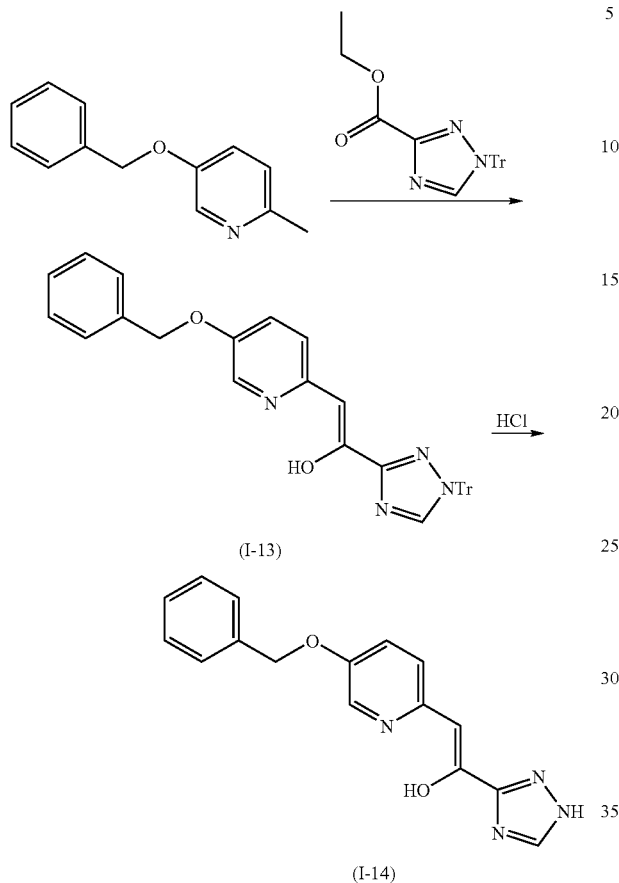

To a solution of 5-benzyloxy-2-methylpyridine (399 mg, 2 mmol) in THF (10 ml) was added dropwise at −78° C. n-butyllithium (2 mmol). To the solution was added 1-trityl-1H-[1,2,4]triazole-3-carboxylic acid ethyl ester (767 mg, 2 mmol). The mixture was stirred for 30 minutes. To the reaction mixture was added an aqueous solution of ammonium chloride. The mixture was extracted with ethyl acetate, washed with water, dried and concentrated. The obtained residue was chromatographed on silica gel (n-hexane-ethyl acetate). The obtained fraction was concentrated under reduced pressure. The obtained crystal was washed with diethyl ether, dried under reduced pressure to give Compound (I-13) (42 mg).

$^1$H-NMR (CDCl$_3$) δ: 4.50 (2/3H, s), 5.07 (2/3H, s), 5.12 (4/3H, s), 6.50 (2/3H, s), 7.05-7.46 (22H, m), 8.96 (2/3H, s), 8.04 (1/3H, s), 8.17 (2/3H, d, J=3.2 Hz), 8.29 (1/3H, bs).

To a solution of Compound (I-13) (28 mg, 0.05 mmol) in dioxane (5 ml) was added at 50° C. an aqueous solution of 1N—HCl (1.5 ml). The mixture was stirred for 30 minutes. After that, to the mixture was added at room temperature an aqueous solution of 1N-NaOH (1.5 ml). The mixture was extracted with ethyl acetate, washed with water, dried and concentrated under reduced pressure. The obtained crystal was washed with diethyl ether and dried under reduced pressure to give Compound (I-14) (11 mg).

$^1$H-NMR (CDCl$_3$) δ: 5.18 (2H, s), 6.62 (1H, s), 7.20-7.50 (6H, m), 8.10-8.50 (2H, m).

Exampe 15

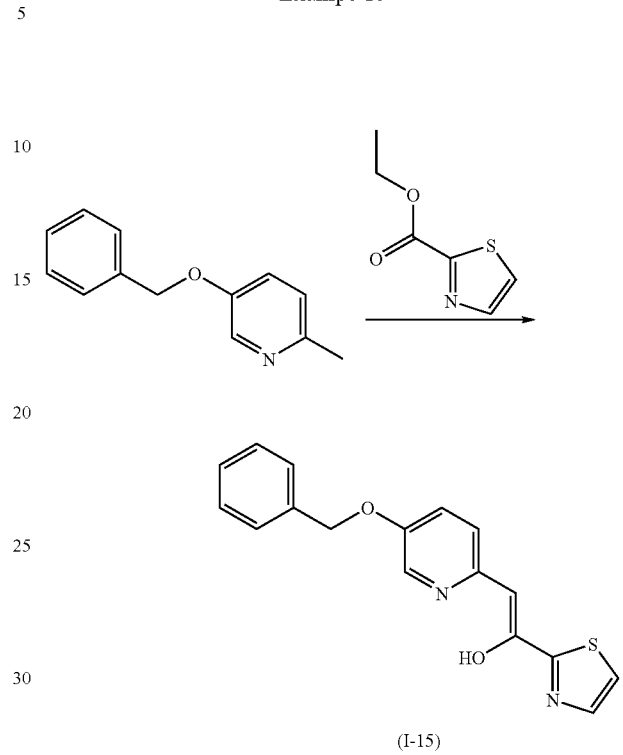

To a solution of 5-benzyloxy-2-methylpyridine (299 mg, 2 mmol) in THF (10 ml) was added dropwise at −78° C. n-butyllithium (2 mmol). To the solution was added thiazole-2-carboxylic acid ethyl ester (314 mg, 2 mmol). The mixture was stirred for 30 minutes. To the reaction mixture was added an aqueous solution of ammonium chloride. The mixture was extracted with ethyl acetate, washed with water, dried and concentrated. The obtained residue was chromatographed on silica gel (n-hexane-ethyl acetate). The obtained fraction was concentrated under reduced pressure. The obtained crystal was washed with diethyl ether, dried under reduced pressure to give Compound (I-15) (51 mg).

$^1$H-NMR (CDCl$_3$) δ: 4.62 (2/3H, s), 5.09 (2/3H, s), 5.14 (4/3H, s), 6.60 (2/3H, s), 7.16 (2/3H, d, J=8.7 Hz), 7.33-7.48 (7H, m), 7.69 (1/3H, d, J=3.5 Hz), 7.87 (2/3H, d, J=3.5 Hz), 8.04 (1/3H, d, J=3.5 Hz), 8.16 (2/3H, d, J=3.5 Hz), 8.34 (1/3H, d, J=3.5 Hz).

Example 16, 17

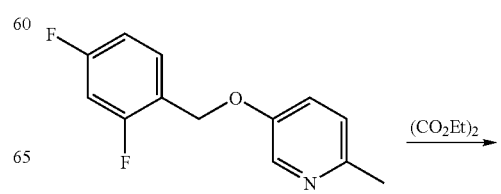

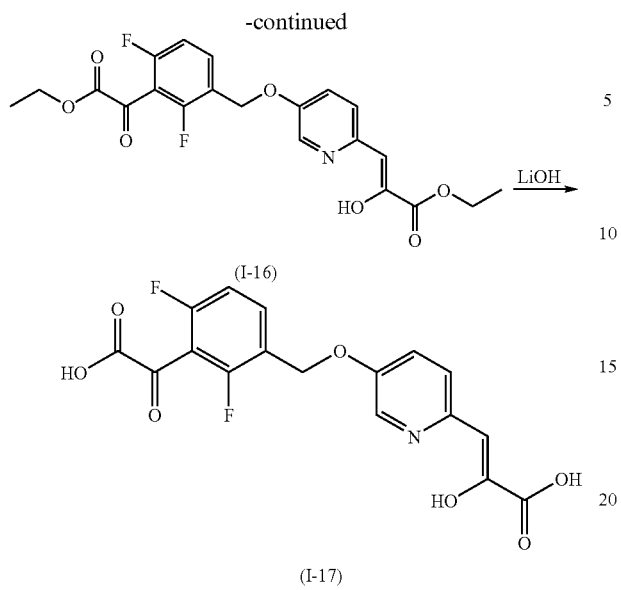

To a solution of 5-(2,4-difluorobenzyloxy)-2-methylpyridine (706 mg, 3 mmol) in THF (10 ml) was added dropwise at −78° C. n-butyllithium (3 mmol). To the solution was added oxalic acid diethyl ester (2.2 g, 15 mmol). The mixture was stirred for 30 minutes. To the reaction mixture was added an aqueous solution of ammonium chloride. The mixture was extracted with ethyl acetate, washed with water, dried and concentrated. The obtained residue was chromatographed on silica gel (n-hexane-ethyl acetate). The obtained fraction was concentrated under reduced pressure. The obtained crystal was washed with diethyl ether, dried under reduced pressure to give Compound (I-16) (42 mg).

$^1$H-NMR (CDCl$_3$) δ: 1.35-1.45 (6H, m), 4.36 (2H, q, J=7.2 Hz), 4.43 (2H, q, J=7.2 Hz), 5.17 (2H, s), 6.57 (1H, s), 7.07 (1H, dt, J=1.4, 9.7 Hz), 7.21 (1H, d, J=9.1 Hz), 7.35 (1H, dd, J=9.1, 2.9 Hz), 7.72 (1H, dq, J=1.4, 9.7 Hz), 8.26 (1H, d, J=2.9 Hz).

To a solution of Compound (I-16) (50 mg, 0.11 mmol) in methanol (3 ml) was added at 70° C. an aqueous solution of lithium hydroxide (1N, 0.33 ml). The mixture was stirred for 1 hour. Methanol was removed under reduced pressure. To the residue was added water. The solution was acidified with citric acid. The mixture was extracted with ethyl acetate, washed with water, dried and concentrated under reduced pressure. The obtained crystal was washed with diethyl ether and dried under reduced pressure to give Compound (I-17) (22 mg).

Example 18, 19

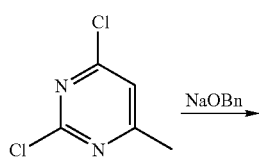

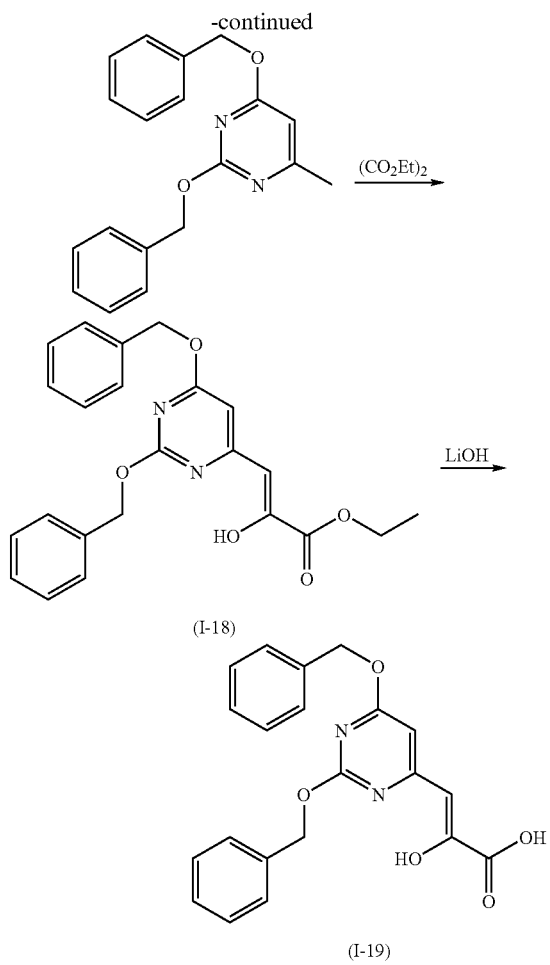

To a solution of sodium hydride (3.2 g, 80 mmol) in DMF (20 ml) was added under ice-cooling benzylalcohol (8.6 g, 80 mmol). To the solution was added 2,4-dichloro-6-methylpyrimidine (3.2 g, 20 mmol). The mixture was stirred at room temperature for 1 hour. To the reaction mixture was added an aqueous solution of ammonium chloride. The mixture was extracted with diethyl ether, washed with water, dried and concentrated. The obtained residue was chromatographed on silica gel (n-hexane-ethyl acetate). The obtained fraction was concentrated under reduced pressure to give 2,4-bisbenzyloxy-6-methylpyrimidine (3.5 g).

Compound (I-18) and (1-19) were prepared from the above-obtained 2,4-bisbenzyloxy-6-methylpyrimidine in accordance with Example 2 and 3.

Compound (I-18)
$^1$H-NMR (CDCl$_3$) δ: 1.39 (3H, t, J=7.1 Hz), 4.35 (2H, q, J=7.11 Hz), 5.39 (2H, s), 5.41 (2H, s), 6.24 (1H, s), 6.38 (1H, s), 7.30 -7.50 (10H, m).

Compound (I-19)
$^1$H-NMR (d$_6$-DMSO) δ: 5.41 (2H, s), 5.42 (2H, s), 6.42 (1H, s), 6.77 (1H, s), 7.30-7.55 (10H, m).

Example 20-23

The reaction was carried out in accordance with the above-shown method. Each structure and physical date of the compound is shown below.

TABLE 3

| Comp. No. | Structure | ¹H-NMR |
|---|---|---|
| I-20 | | (CDCl$_3$) δ: 1.40(3H,t,J=7.1 Hz), 4.36(2H,q,J=7.1 Hz), 5.33(2H,s), 6.57(1H,s), 6.75(1H,d,J=8.0 Hz), 6.84(1H,d,J=7.8Hz), 7.30-7.50(5H,m), 7.65(1H,dd,J=8.0,7.8 Hz). |
| I-21 | 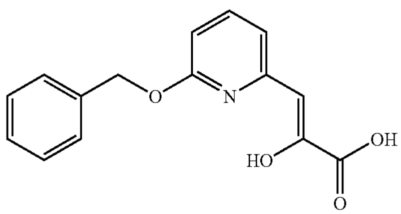 | (d$_6$-DMSO) δ: 5.35(2H,s), 6.53(1H,s), 6.87(1H,d,J8.1 Hz), 7.18(1H,d,J=7.9 Hz), 7.30-7.50(5H,m), 7.82(1H,dd,J=8.1,7.9 Hz). |
| I-22 | 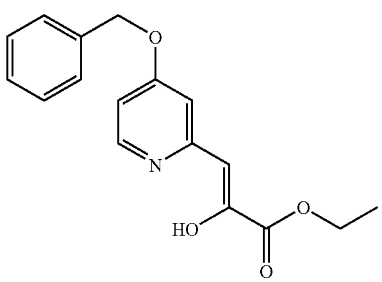 | (CDCl$_3$) δ: 1.40(3H,t,J=7.3 Hz), 4.35(2H,q,J=7.3 Hz), 5.14(2H,s), 6.47(1H,s), 6.70-6.80(2H,m), 7.30-7.50(5H,m), 8.16(1H,d,J=6.0 Hz). |
| I-23 | 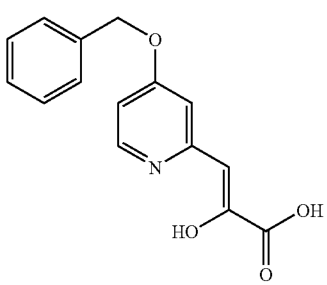 | (d$_6$-DMSO) δ: 5.22(2H,s), 6.35(1H,s), 6.91(1H,dd,J=6.0,2.4 Hz), 7.11(1H,d,J=2.4 Hz), 7.32-7.53(5H,m), 8.29(1H,d,J=6.0 Hz). |

Example 24, 25

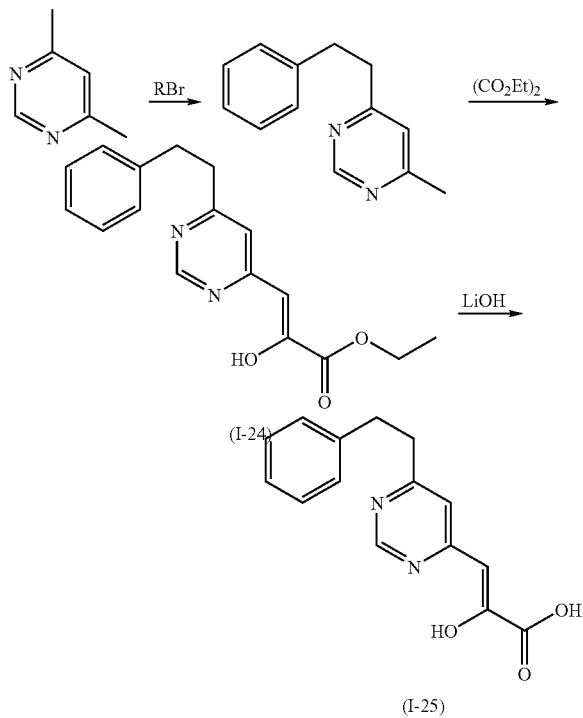

To a solution of 4,6-dimethylpyrimidine (1.08 g, 10 mmol) in THF (40 ml) was added dropwise at −78° C. a solution of n-butyllithium. To the solution was added benzylbromide (1.71 g, 10 mmol). The mixture was warmed up to 0° C. and stirred for 30 minutes. To the reaction mixture was added an aqueous solution of ammonium chloride. The mixture was extracted with ethyl acetate, washed with water, dried and concentrated. The obtained residue was chromatographed on silica gel (n-hexane-ethyl acetate). The obtained fraction was concentrated to give 4-methyl-6-phenethylpyrimidine (1.7 g).

Compound (I-24) and (I-25) were prepared from the above-obtained 4-methyl-6-phenethylpyrimidine in accordance with Example 2 and 3.

Compound (I-24)

$^1$H-NMR (CDCl$_3$) δ: 1.40 (3H, t, J=7.1 Hz), 3.06 (4H, s), 4.35 (2H, q, J=7.1 Hz), 6.39 (1H, s), 6.86 (1H, s), 7.12-7.35 (6H, m), 8.95 (1H, s).

Compound (I-25)

$^1$H-NMR (d$_6$-DMSO) δ: 3.00 (4H, s), 6.29 (1H, s), 7.15-7.40 (6H, m), 8.92 (1H, s).

Example 26-35

The reaction was carried out in accordance with the above-shown method. Each structure and physical date of the compound is shown below.

TABLE 4

| Comp. No. | Structure | $^1$H—NMR |
|---|---|---|
| 1-26 | 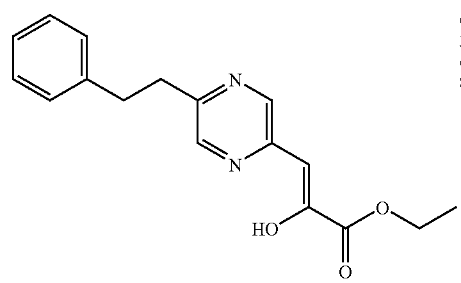 | (CDCl$_3$) δ: 1.40(3H, t, J=7.1Hz), 3.05-3.17(4H, m), 4.37(2H, q, J=7.1Hz), 6.63(1H, s), 7.15-7.28(5H, m), 8.15(1H, s), 8.52(1H, s). |
| 1-27 | 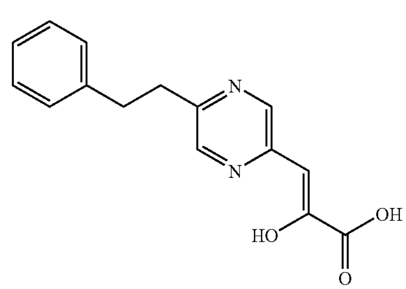 | (d$_6$-DMSO) δ: 3.00-3.17(4H, m), 6.62(1H, s), 7.10-7.30(5H, m), 8.44(1H, s), 8.85(1H, s). |

TABLE 4-continued

| Comp. No. | Structure | ¹H—NMR |
|---|---|---|
| 1-28 | 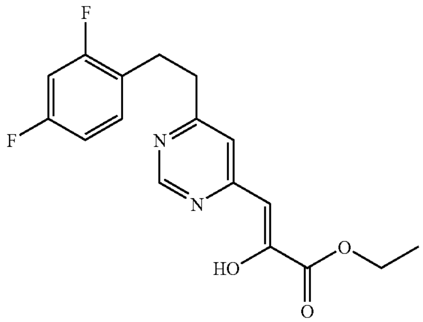 | (CDCl₃) δ: 1.40(3H, t, J=7.1Hz), 3.07(4H, s), 4.37(2H, q, J=7.1Hz), 6.42(1H, s), 6.75-6.86(2H, m), 6.91(1H, s), 7.07-7.15(1H, m), 8.97(1H, s). |
| 1-29 | 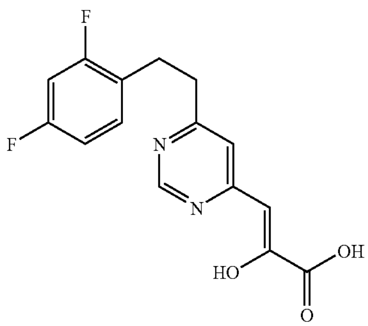 | (d₆-DMSO) δ: 2.90-3.10(4H,m), 6.30(1H, s), 6.96-7.29(1H, m), 7.13-7.20(1H, m), 7.29-7.37(2H, m), 8.91(1H, s). |
| 1-30 | 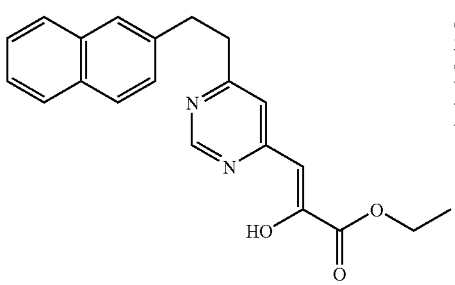 | (CDCl₃) δ: 2.90-3.10(4H, m) 3.20(4H, m), 4.36(2H, q, J=7.1Hz), 6.39(1H, s), 6.92(1H, s), 7.33(1H, dd, J=8.7, 2.1Hz), 7.43-7.47(2H, m), 7.63(1H, s), 7.75-7.82(3H, m), 8.99(1H, s). |
| 1-31 | 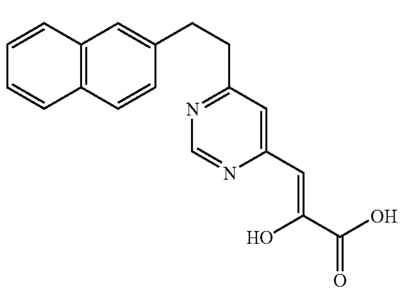 | (d₆-DMSO) δ: 3.05-3.25(4H,m), 6.29(1H, s), 7.40-7.50(4H, m), 7.73(1H, s), 7.80-7.88(3H, m), 8.92(1H, s). |

TABLE 5

| Comp. No. | Structure | ¹H-NMR |
|---|---|---|
| I-32 | 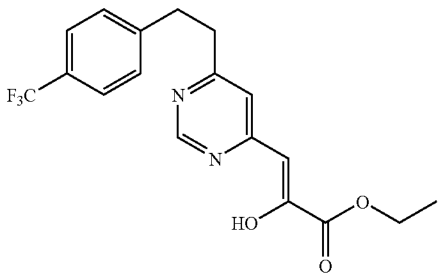 | (CDCl$_3$)δ:1.39(3H,t,J=7.2Hz),3.05-3.20(4H,m),4.37(2H,q,J=7.2Hz),6.42(1H,s),6.91(1H,s),7.31(2H,d,J=7.8Hz),7.54(2H,d,J=7.8Hz),8.98(1H,s). |
| I-33 | 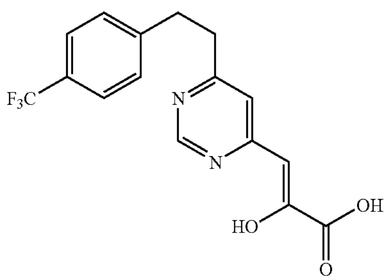 | (d$_6$-DMSO)δ:3.00-3.20(4H,m),6.31(1H,s),7.36(1H,s),7.47(2H,d,J=8.1Hz),7.63(2H,d,J=8.1Hz),8.91(1H,s). |
| I-34 | 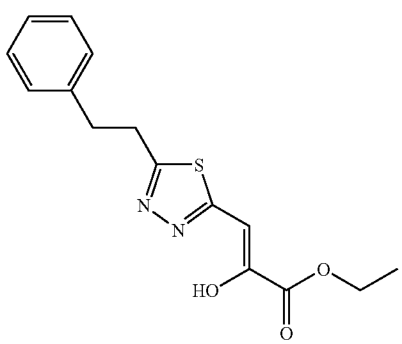 | (CDCl$_3$)δ:1.40(3H,t,J=7.1Hz),3.15(2H,dd,J=7.5,7.5Hz),3.45(2H,dd,J=7.5,7.5Hz),4.38(2H,q,J=7.1Hz),6.80(1H,s),7.20-7.35(5H,m). |
| I-35 | 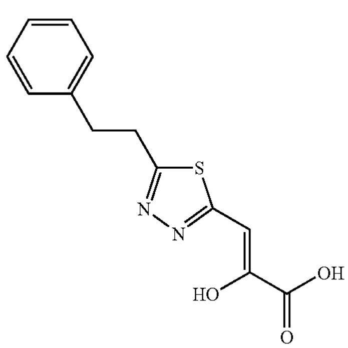 | (d$_6$-DMSO)δ:3.05(2H,dd,J=7.5,7.5Hz),3.38(2H,dd,J=7.5,7.5Hz),6.73(1H,s),7.15-7.32(5H,m). |

Example 36-43

The following compounds were prepared from commercially available compounds in accordance with Example 2 and 3. Each structure and physical date of the compound is shown below.

TABLE 6

| Comp. No. | Structure | $^1$H-NMR |
|---|---|---|
| I-36 | 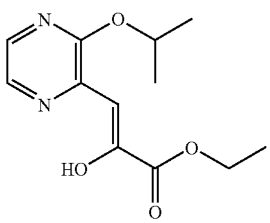 | (CDCl$_3$)δ:1.40(6H,d,J=6.1Hz), 1.41(3H,t,J=6.9Hz),4.39(2H,q, J=6.9Hz),5.37(1H,m),6.87(1H,s), 7.87(1H,d,J=2.0Hz),7.95(1H,d, J=2.0Hz). |
| I-37 | 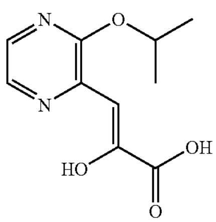 | (d$_6$-DMSO)δ:1.38(6H,d,J=6.1Hz), 5.31(1H,m),6.64(1H,s),8.08(2H,s). |
| I-38 | 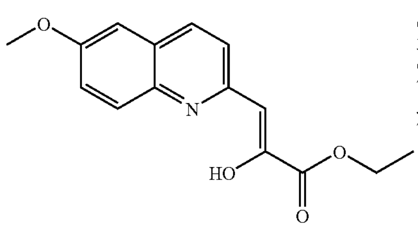 | (CDCl$_3$)δ:1.41(3H,t,J=7.3Hz), 3.92(3H,s),4.38(2H,q,J=7.3Hz), 6.50(1H,s),7.04(1H,d,J=3.1Hz), 7.15(1H,d,J=8.9Hz),7.34(1H,dd, J=8.9,3.1Hz),7.66(1H,d,J=9.3Hz), 7.93(1H,d,J=9.3Hz). |
| I-39 | 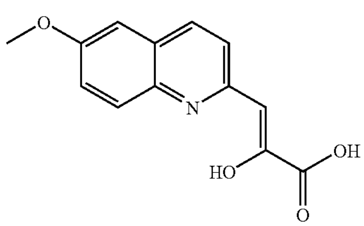 | (d$_6$-DMSO)δ:3.89(3H,s),6.50(1H,s), 7.40-7.44(2H,m),7.49(1H,d,J=8.8Hz), 7.85(1H,d,J=9.9Hz),8.25(1H,d, J=8.8Hz). |
| I-40 | 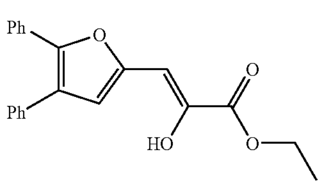 | (CDCl$_3$)δ:1.41(3H,t,J=7.2Hz), 4.39(2H,q,J=7.2Hz),6.63(1H,s),7.35-7.45(6H,m),7.60-7.68(4H,m). |
| I-41 | 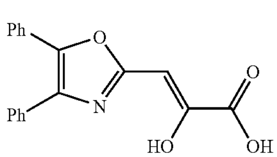 | (d$_6$-DMSO)δ:6.42(1H,s),7.35-7.52(6H,m),7.55-7.65(4H,m). |

TABLE 7

| Comp. No. | Structure | ¹H-NMR |
|---|---|---|
| I-42 | 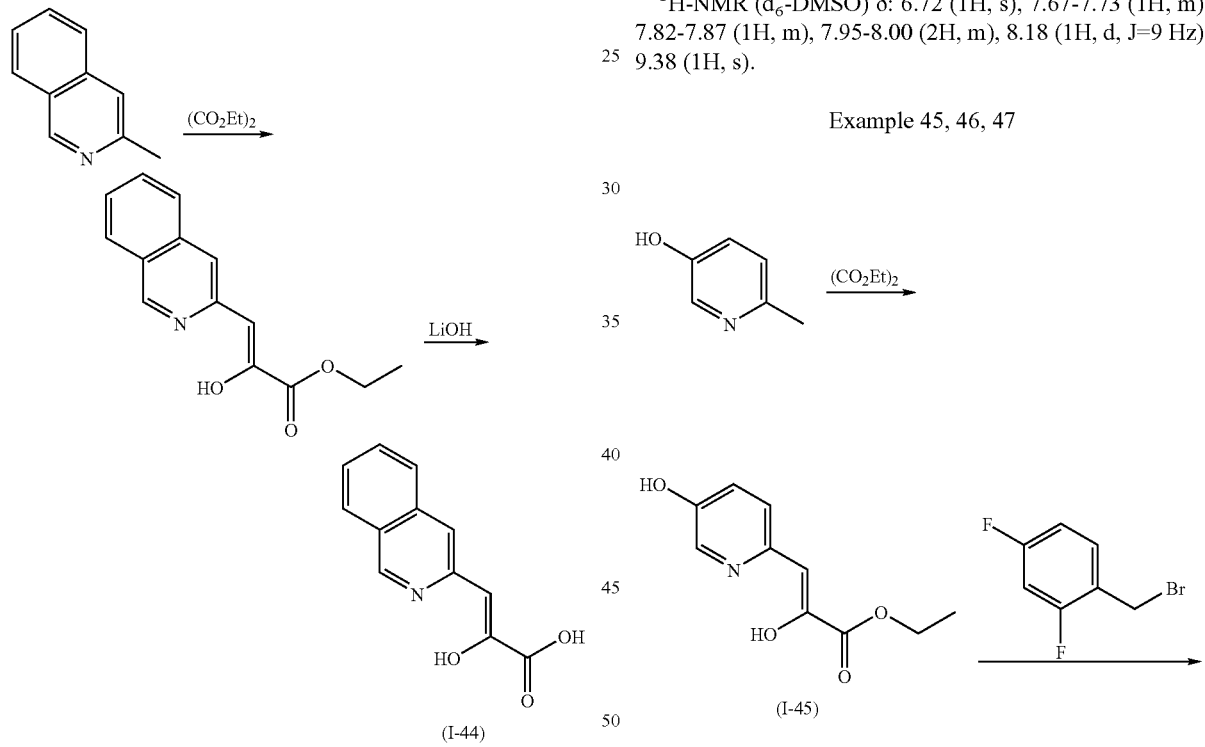 | (CDCl$_3$)δ:1.42(3H,t,J=7.0Hz), 4.41(2H,q,J=7.0Hz), 6.66(1H,s),7.35-7.43(2H,m),7.50-7.60(1H,m), 7.66-7.73(1H,m). |
| I-43 | 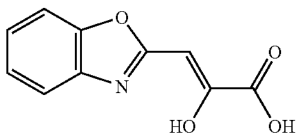 | (d$_6$-DMSO)δ:6.42(1H,s),7.36-7.43(2H,m),7.68-7.78(2H,m). |

Example 44

Example 45, 46, 47

The obtained crystal was washed with diisopropyl ether and dried under reduced pressure to give Compound (I-44) (10 mg).

$^1$H-NMR (d$_6$-DMSO) δ: 6.72 (1H, s), 7.67-7.73 (1H, m), 7.82-7.87 (1H, m), 7.95-8.00 (2H, m), 8.18 (1H, d, J=9 Hz), 9.38 (1H, s).

To a solution of 2-methylisoquinoline (286 mg, 2 mmol) and oxalic acid diethyl ester (292 mg, 2 mmol) in THF (5 ml) was added t-BuOK (224 mg, 2 mmol). The mixture was stirred at 50° C. for 2 hours. To the reaction mixture was added an aqueous solution of ammonium chloride. The mixture was extracted with ethyl acetate, washed with water, dried and concentrated.

To a solution of the obtained residue in methanol (5 ml) was added an aqueous solution of lithium hydroxide (1N, 1 ml). The mixture was stirred at room temperature for 6 hours. Methanol was removed under reduced pressure. To the residue was added water. The solution was acidified with citric acid. The mixture was extracted with ethyl acetate, washed with water, dried and concentrated under reduced pressure.

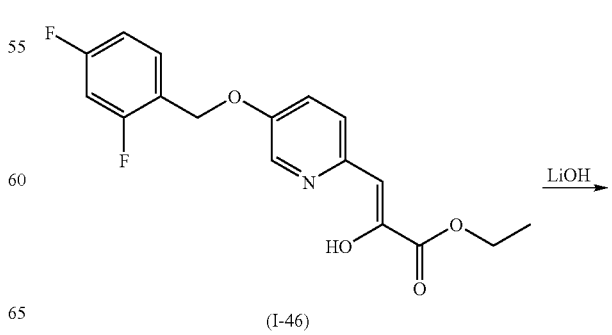

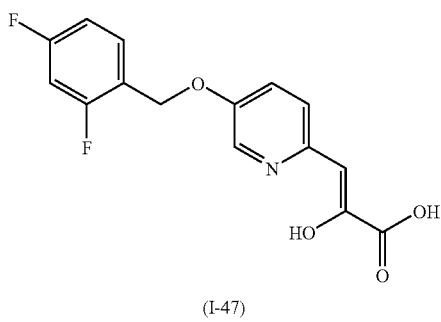

(I-47)

To a solution of 5-hydroxy-2-methylpyridine (1.09 g, 10 mmol) in THF (50 ml) was added dropwise at −78° C. n-butyllithium (20 mmol). The mixture was warmed up to 0° C., stirred for 10 minutes and cooled to −78° C. To the mixture was added oxalic acid diethyl ester (7.0 g, 50 mmol). The mixture was stirred for 10 minutes. To the reaction mixture was added an aqueous solution of ammonium chloride. The mixture was extracted with ethyl acetate, washed with water, dried and concentrated. The obtained residue was chromatographed on silica gel (chloroform-methanol). The obtained fraction was concentrated under reduced pressure. The obtained crystal was washed with diethyl ether and dried under reduced pressure to give Compound (I-45)(450 mg).

$^1$H-NMR (CDCl$_3$) δ: 1.35-1.42 (3H, m), 4.32-4.39 (2H, m), 6.55 (1H, s), 7.17 (1H, d, J=8.7 Hz), 7.30(1H, dd, J=8.4, 2.4 Hz), 8.179 (1H, d, J=2.4 Hz).

To a solution of sodium hydride (80 mg, 2 mmol) in DMF (3 ml) was added under ice-cooling Compound (I-45) (209 mg, 1 mmol). To the mixture was added 2,4-difluorobenzyl-bromide (207 mg, 1 mmol). The mixture was stirred for 3 hours. To the reaction mixture was added an aqueous solution of ammonium chloride. The mixture was extracted with diethyl ether, washed with water, dried and concentrated. The obtained crystal was washed with diisopropyl ether, dried under reduced pressure to give Compound (I-46) (104 mg).

$^1$H-NMR (CDCl$_3$) δ: 1.39 (3H, t, J=7.1 Hz), 4.35 (2H, q, J=7.1 Hz), 5.14 (2H, s), 6.56 (1H, s), 6.84-6.96 (2H, m), 7.19 (1H, d, J=8.7 Hz), 7.34 (1H, dd, J=2.7, 8.7 Hz), 7.42-7.50 (1H, m), 8.24 (1H, d, J=2.7 Hz).

Example 47

Compound (I-47) (50 mg) was prepared from Compound (I-46) in accordance with Example 3.

$^1$H-NMR (d$_6$-DMSO) δ: 5.24 (2H, s), 6.58 (1H, s), 7.10-7.19 (1H, m), 7.29-7.37 (1H, m), 7.54 (1H, d, J=8.7 Hz), 7.62-7.70 (1H, m), 8.40 (1H, d, J=3.0 Hz).

Example 48-50

The following compounds were prepared in accordance with the above-shown process. Each structure and physical date of the compound is shown below.

TABLE 8

| Comp. No. | Structure | $^1$H-NMR |
|---|---|---|
| I-48 | ![structure] | (CDCl$_3$)δ:1.39(3H,t,J=7.2Hz), 4.35(2H,q,J=7.2Hz)5.20(2H,s), 6.56(1H,s),7.20(1H,d,J=8.7Hz) 7.33(1H,dd,J=2.7,8.7Hz),7.55(2H,d, J=7.8Hz),7.68(2H,d,J=7.8Hz), 8.23(1H,d,J=2.7Hz). |
| I-49 | ![structure] | (d$_6$-DMSO)δ:5.36(2H,s),6.57(1H,s), 7.54(1H,d,J=8.7Hz),7.64(1H,dd, J=3.0,9.0Hz),7.69(2H,d,J=8.7Hz). 7.79(2H,d,J=8.7Hz), 8.40(1H,d,J=3.0Hz) |

TABLE 8-continued

| Comp. No. | Structure | ¹H-NMR |
|---|---|---|
| I-50 | ![structure] | (CDCl₃)δ:1.39(3H,t,J=7.1Hz), 4.36(2H,q,J=7.1Hz),5.32(2H,s), 6.61(1H,s),7.25-7.60(5H,m),7.82-7.91(4H,m),8.30(1H,d,J=2.7Hz). |

Example 51, 52, 53

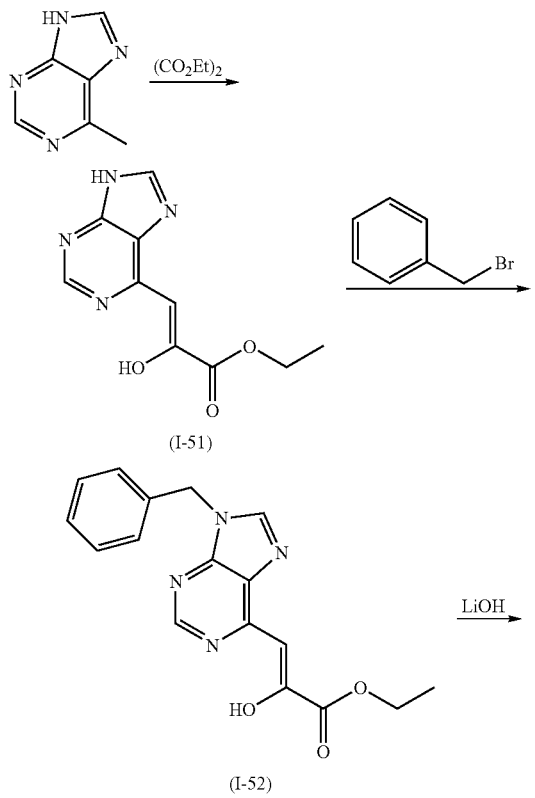

To a solution of 6-methylpurine (250 mg, 1.86 mmol) in THF (10 ml) was added dropwise at −78° C. a solution of n-butyllithium (3.73 mmol). The mixture was warmed up to room temperature. The mixture was stirred for 1 hour and cooled to −78° C. To the solution was added oxalic acid diethyl ether (1.4 g, 9.3 mmol). The mixture was stirred for 10 minutes. To the solution was added an aqueous solution of ammonium chloride. The obtained crystal was washed with water and ethyl acetate and dried under reduced pressure to give Compound (I-51) (103 mg).

¹H-NMR (d₆-DMSO) δ: 1.30 (3H, t, J=7.2 Hz), 4.25 (2H, q, J=7.2 Hz), 6.48 (1H, s), 8.45 (1H, s), 8.56 (1H, s).

To a solution of sodium hydride (28 mg, 0.68 mmol) in DMF (3 ml) was added under ice-cooling Compound (I-51) (80 mg, 0.34 mmol). To the solution was added benzylbromide (59 mg, 0.34 mmol). To the reaction mixture was added an aqueous solution of ammonium chloride. The obtained crystal was washed with water and ethyl acetate and concentrated under reduced pressure to give Compound (I-52) (53 mg).

¹H-NMR (d₆-DMSO) δ: 1.29 (3H, t, J=7.1 Hz), 4.24 (2H, q, J=7.1 Hz), 5.46 (2H, s), 6.49 (1H, s), 7.32-7.36 (5H, m), 8.57 (1H, s), 8.60 (1H, s).

Example 53

Compound (I-53) (9 mg) was prepared from Compound (I-52) in accordance with Example 3.

¹H-NMR (d₆-DMSO) δ: 5.45 (2H, s), 6.54 (1H, s), 7.25-7.40 (5H, m), 8.57 (1H, s), 8.61 (1H, s).

Example 54, 55

The following compounds were prepared in accordance with the above-shown process. Each structure and physical date of the compound is shown below.

TABLE 9
| Comp. No. | Structure | $^1$H-NMR |
|---|---|---|
| I-54 | 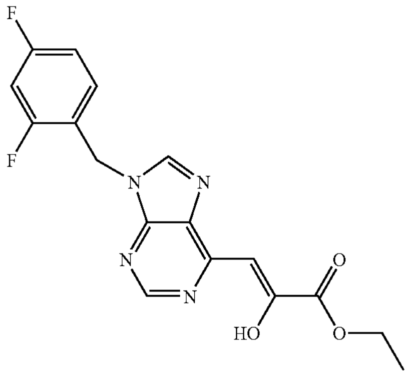 | (d$_6$-DMSO)δ:1.29(3H,t,J=7.1Hz), 4.24(2H,q,J=7.1Hz),5.50(2H,s), 6.49(1H,s),7.03-7.12(1H,m),7.20-7.46(2H,m),8.50(1H,s),8.59(1H,s). |
| I-55 | 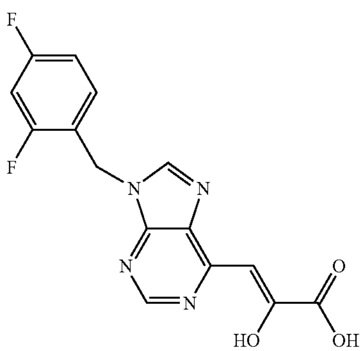 | (d$_6$-DMSO)δ:5.50(2H,s),6.54(1H,s), 7.05-7.16(1H,m),7.27-7.46(2H,m), 8.50(1H,s),8.60(1H,s). |
Example 56, 57, 58, 59
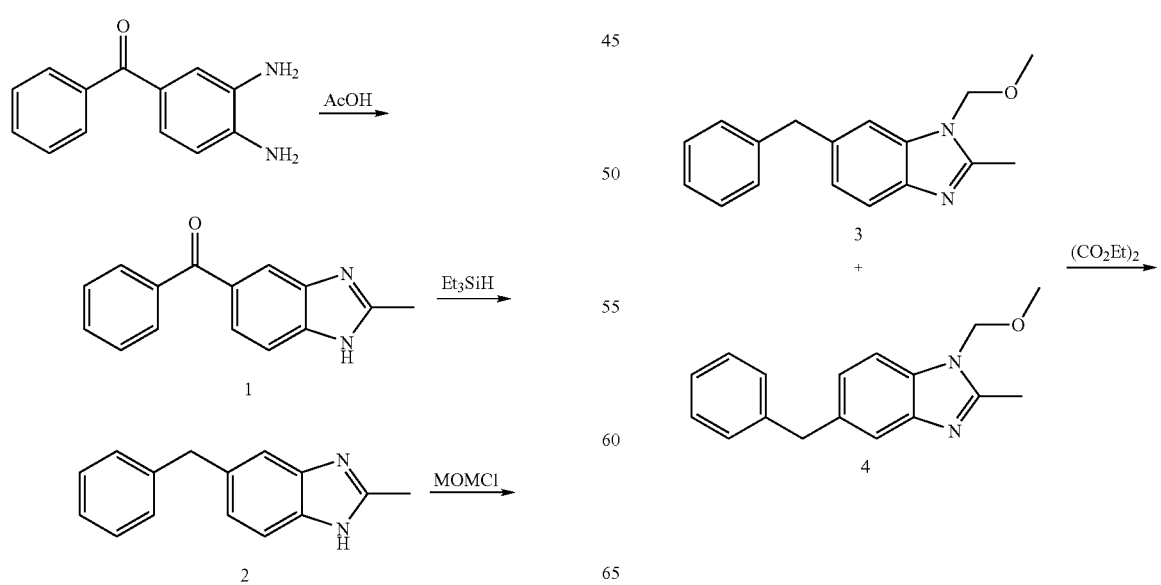
-continued

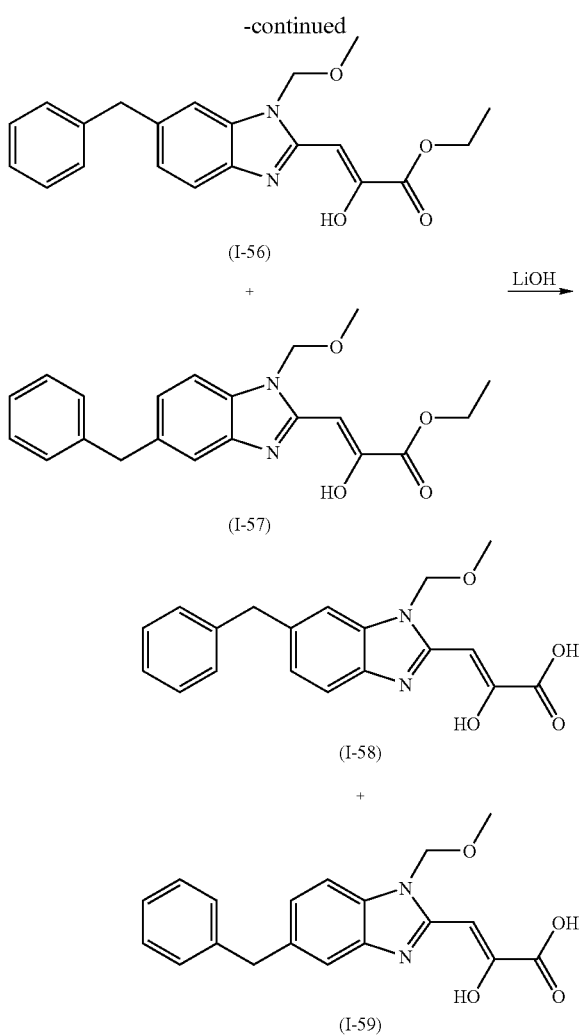

matographed on silica gel (ethyl acetate). The obtained fraction was concentrated to give a mixture of Compound 3 and 4 (1:1) (3.1 g).

A mixture of Compound (I-58) and (1-59) (1:1) was prepared from the mixture of Compound 3 and 4 (1:1) in accordance with Example 2 and 3. The mixture of Compound (I-56) and (1-57)

$^1$H-NMR (CDCl$_3$) δ: 1.40 (3H, t, J=7.2 Hz), 3.33, 3.34 (3H, s), 4.09, 4.11 (2H, s), 4.36 (2H, q, J=7.2 Hz), 5.42, 5.43 (2H, s), 6.37, 6.39 (1H, s), 7.12-7.45 (8H, m). regio isomer mixture The mixture of Compound (I-58) and (I-59)

$^1$H-NMR (d$_6$-DMSO) δ: 3.24, 3.26 (3H, s), 4.04, 4.05 (2H, s), 5.56 (2H, s), 6.24, 6.27 (1H, s), 7.13-7.60 (8H, m). regio isomer mixture Example 60, 61

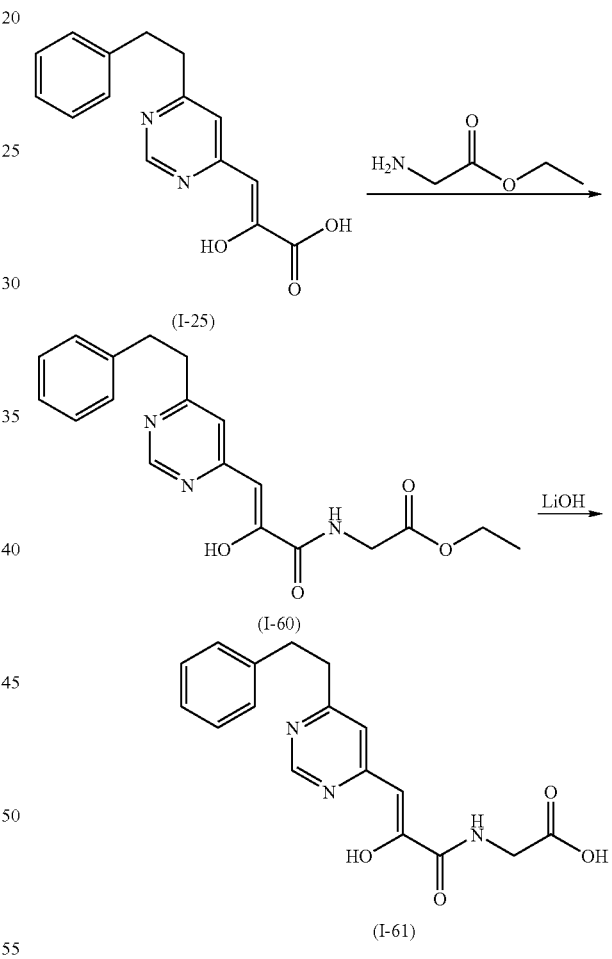

To a solution of 3,4-diaminobenzophenone (6.36 g, 30 mmol) in acetic acid (30 ml) was added acetic anhydride (2 ml). The mixture was stirred at 100° C. for 2 hours. Acetic acid was removed. To the residue was added water and sodium hydrogencarbonate. The mixture was extracted with ethyl acetate, washed with water, dried and concentrated. The obtained crystal was washed with ethyl acetate and dried under reduced pressure to give Compound 1 (6.0 g).

To a solution of Compound 1 (4.7 g, 20 mmol) in trifluoroacetic acid (70 ml) was added triethylsilane (7.0 g, 60 mmol). The mixture was stirred at room temperature for 15 hours. The solvent was removed. To the residue was added water and sodium hydrogencarbonate. The mixture was extracted with ethyl acetate, washed with water, dried and concentrated. The obtained residue was chromatographed on silica gel (n-hexane). The obtained fraction was concentrated under reduced pressure and dried under reduced pressure to give Compound 2 (4.8 g).

To a solution of Compound 2 (4.8 g) in DMF (30 ml) were added triethylamine (3.0 g, 30 mmol) and chloromethoxymethane (2.4 g, 30 mmol). The mixture was stirred at room temperature for 1 hour. To the reaction mixture was added an aqueous solution of sodium hydrogencarbonate. The mixture was extracted with ethyl acetate, washed with water, dried and concentrated. The obtained residue was chro- To a solution of Compound (I-25) (135 mg, 0.5 mmol) in chloroform (6 ml) and acetonitrile (2 ml) were added glycine ethyl ester (140 mg, 1 mmol), HOBt (135 mg, 1 mmol) and WSCD (155 mg, 1 mmol). The mixture was stirred at room temperature for 1 hour. The reaction mixture mixed with water, extracted with chloroform, washed water, dried and concentrated. To the obtained residue was added dioxane (5 ml) and followed to add 3N hydrochloric acid (1 ml). The mixture was stirred at room temperature for 30 minutes. To the solution was added water. The aqueous solution was alkalified with sodium hydrogencarbonate. The mixture was extracted with ethyl acetate, washed with water, dried and concentrated. The obtained crystal was washed with diethyl ether and concentrated to give Compound (I-60) (110 mg).

¹H-NMR (CDCl₃) δ: 1.31 (3H, t, J=7.2 Hz), 3.05 (4H, s), 4.15 (2H, d, J=5.7 Hz), 4.25 (2H, q, J=7.2 Hz), 6.40 (1H, s), 6.80 (1H, s), 7.15-7.32 (5H, m), 7.53 (1H, s), 8.82 (1H, s).

To a solution of Compound (I-60) (110 mg, 0.31 mmol) in methanol was added an aqueous solution of lithium hydroxide (1N, 0.31 ml). The mixture was stirred at room temperature for 30 minutes. Methanol was removed. To the residue was added water. The solution was acidified with citric acid. The mixture was extracted with ethyl acetate, washed with water, dried and concentrated. The obtained crystal was washed with diethyl ether and concentrated under reduced pressure to give Compound (I-61) (90 mg).

¹H-NMR (d₆-DMSO) δ: 2.88-3.02 (4H, m), 3.84 (2H, d, J=6.0 Hz), 6.17 (1H, s), 7.10 (1H, s), 7.15-7.30 (5H, m), 8.55 (1H, s), 8.76 (1H, s).

Example 62-86

Examples were carried out in accordance with the above-shown process. Each structure and physical date of the compound is shown below.

TABLE 10

| Comp. No. | Structure | ¹H-NMR |
|---|---|---|
| I-62 | 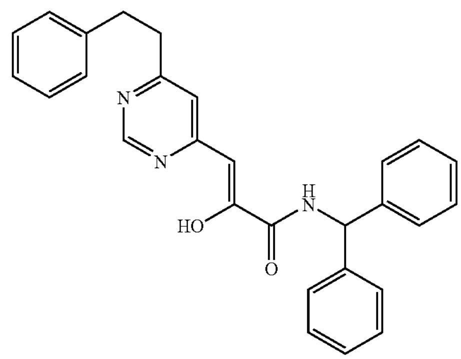 | (CDCl₃)δ:3.03(4H,s),6.32(1H,d, J=7.5Hz),6.42(1H,s),6.79(1H,s), 7.15-7.40(15H,m),7.72(1H,d, J=7.5Hz),8.80(1H,s). |
| I-63 | 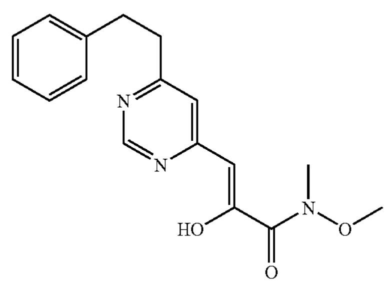 | (CDCl₃)δ:2.95-3.10(4H,m),3.32(3H,s), 3.81(3H,s),5.76(1H,s),6.64(1H,s), 7.15-7.32(5H,m),8.65(1H,s). |
| I-64 | 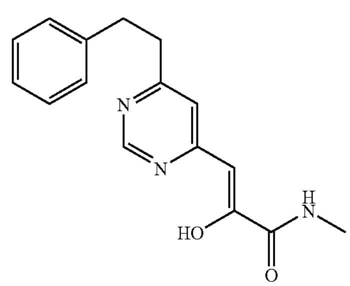 | (CDCl₃)δ:2.95(3H,d,J=5.1Hz), 3.05(4H,s),6.41(1H,s),6.79(1H,s), 7.06(1H,s),7.15-7.32(5H,m), 8.80(1H,s). |
| I-65 | 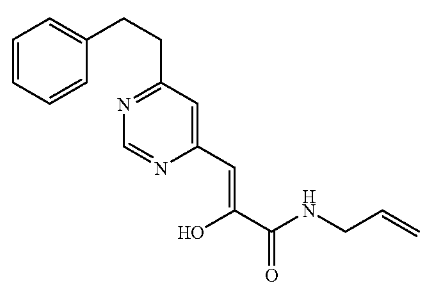 | (CDCl₃)δ:3.00-3.06(4H,m),4.00-4.02(2H,m),5.15-5.30(2H,m),5.80-6.00(1H,m),6.41(1H,s),6.79(1H,d, J=1.5Hz),7.15-7.35(6H,m),8.79(1H, d, J=1.5Hz). |

TABLE 10-continued

| Comp. No. | Structure | ¹H-NMR |
|---|---|---|
| I-66 | 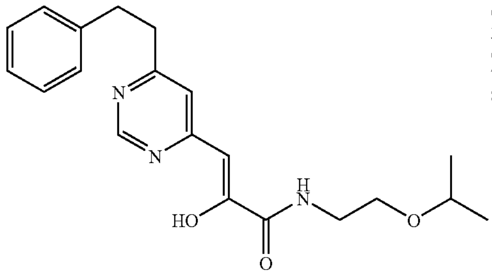 | (CDCl₃)δ:1.18(6H,d,J=6.0Hz),3.00-3.06(4H,m),3.50-3.65(5H,m),6.41(1H,s),6.79(1H,d,J=3.0Hz),7.15-7.30(5H,m),7.43(1H,bs),8.79(1H,d,J=3.0Hz). |
| I-67 | 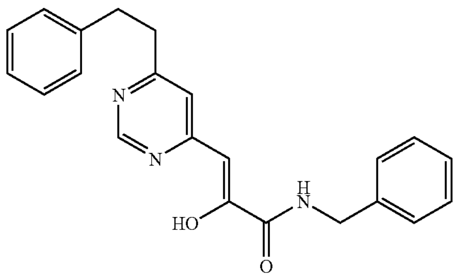 | (CDCl₃)δ:3.00-3.06(4H,m),4.57(2H,d,J=6.0Hz),6.44(1H,s),6.79(1H,d,J=1.5Hz),7.15-7.40(11H,m),8.78(1H,d,J=1.5Hz). |

TABLE 11

| Comp. No. | Structure | ¹H-NMR |
|---|---|---|
| I-68 | 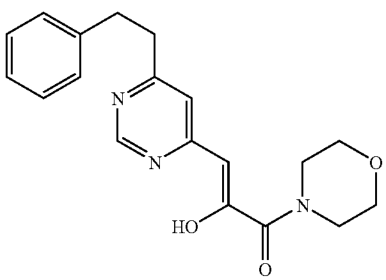 | (CDCl₃) δ: 2.95-3.10(4H, m), 3.65-3.80(8H, m), 5.74(1H, s), 6.62(1H, d, J=1.2Hz), 7.18-7.35(5H, m), 8.62(1H, s). |
| I-69 | 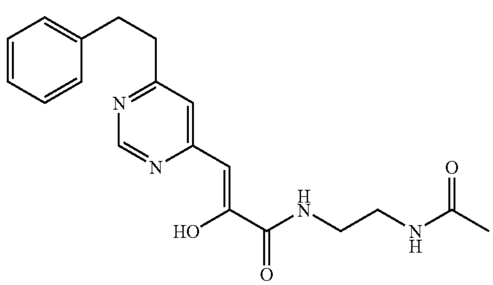 | (CDCl₃) δ: 2.00(3H, s), 3.00-3.10(4H, m), 3.44-3.60(4H, m), 6.19(1H, bs), 6.37(1H, s), 6.77(1H, d, J=1.2Hz), 7.15-7.35(5H, m), 7.60(1H, bs), 8.78(1H, s). |
| I-70 | 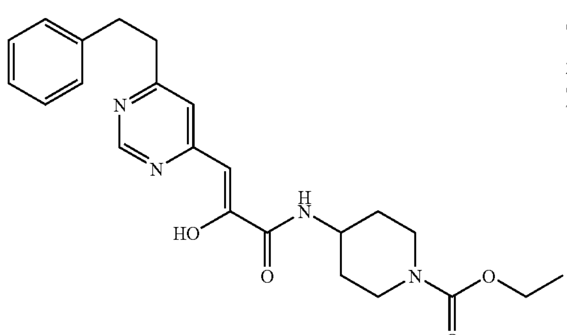 | (CDCl₃) δ: 1.27(3H, t, J=7.2Hz), 1.35-.60(2H, m), 1.95-2.02(2H, m), 2.95-3.10(6H, m), 4.00-4.20(5H, m), 6.39(1H, s), 6.78(1H, d, J=1.2Hz), 7.15-7.35(5H, m), 8.77(1H, s). |

TABLE 11-continued

| Comp. No. | Structure | ¹H-NMR |
|---|---|---|
| I-71 | 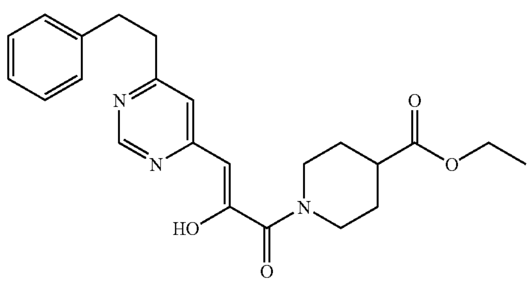 | (CDCl₃) δ: 1.26(3H, t, J=7.2Hz), 1.65-1.82(2H, m), 1.85-2.05(2H, m), 2.55-2.65(1H, m), 2.90-3.10(5H, m), 3.12-3.28(1H, m), 4.00-4.10(1H, m), 4.15(2H, q, J=7.2Hz), 4.30-4.42(1H, m), 5.66(1H, s), 6.60(1H, d, J=0.9Hz), 7.15-7.38(5H, m), 8.61(1H, s). |
| I-72 | 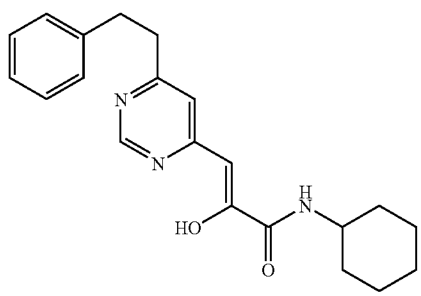 | (CDCl₃) δ: 1.18-1.80(8H, m), 1.90-2.02(2H, m), 3.00-3.10(4H, m), 3.80-3.95(1H, m), 6.40(1H, s), 6.78(1H, d, J=1.2Hz), 6.96(1H, d, J=8.1Hz), 7.15-7.38(5H, m), 8.78(1H, s). |
| I-73 | 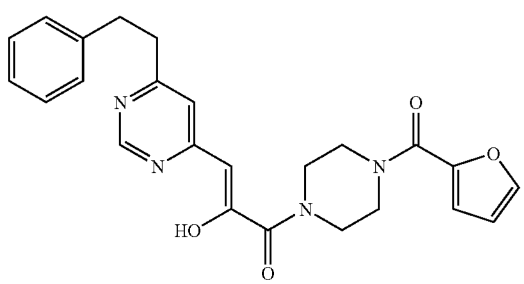 | (CDCl₃) δ: 3.00-3.10(4H, m), 3.70-3.95(8H, m), 5.77(1H, s), 6.51(1H, m), 6.63(1H, s), 7.06(1H, m), 7.15-7.38(5H, m), 7.50(1H, s), 8.63(1H, s). |

TABLE 12

| Comp. No. | Structure | ¹H-NMR |
|---|---|---|
| I-74 | 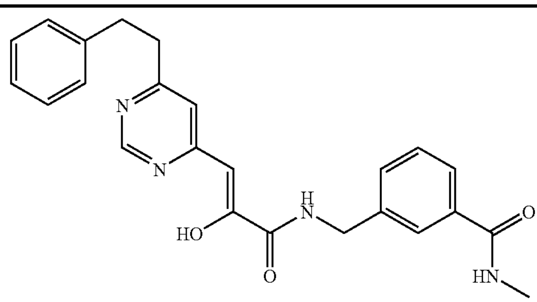 | (CDCl₃) δ: 3.01(3H, d, J=4.8Hz), 3.02-3.08(4H, m), 4.60(2H, d, J=6.3Hz), 6.20(1H, bs), 6.42(1H, s), 6.78(1H, d, J=1.2Hz), 7.15-7.32(4H, m), 7.38-7.50(3H, m), 7.64-7.74(2H, m), 8.78(1H, s). |
| I-75 | 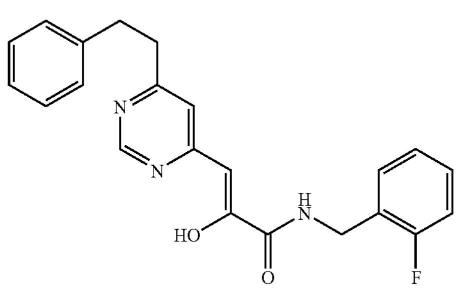 | (CDCl₃) δ: 3.00-3.06(4H, m), 4.62(2H, d, J=6.0Hz), 6.42(1H, s), 6.78(1H, d, J=1.5Hz), 7.10-7.40(9H, m), 7.43(1H, bs), 8.78(1H, d, J=1.5Hz). |

TABLE 12-continued

| Comp. No. | Structure | $^1$H-NMR |
|---|---|---|
| I-76 | 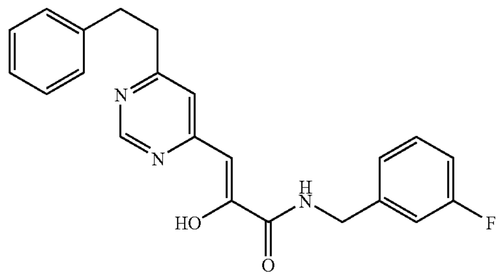 | (CDCl$_3$) δ: 3.00-3.06(4H, m), 4.56(2H, d, J=6.0Hz), 6.44(1H, s), 6.79(1H, d, J=1.5Hz), 6.98-7.38(9H, m), 7.43(1H, bs), 8.78(1H, d, J=1.5Hz). |
| I-77 | 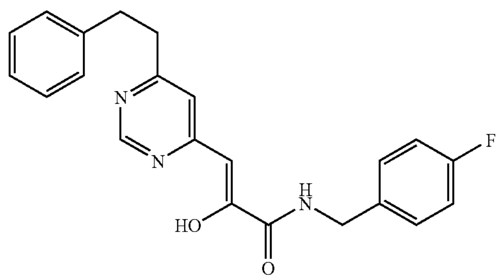 | (CDCl$_3$) δ: 3.00-3.06(4H, m), 4.53(2H, d, J=6.0Hz), 6.43(1H, s), 6.79(1H, d, J=1.5Hz), 7.00-7.10(2H, m), 7.18-7.38(7H, m), 7.40(1H, bs), 8.78(1H, s). |
| I-78 | 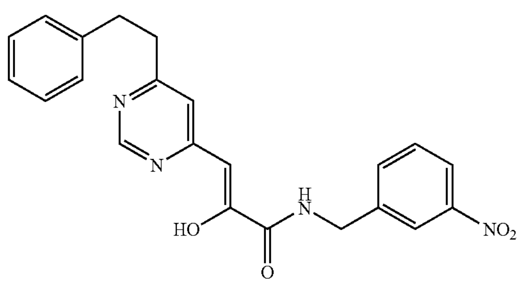 | (CDCl$_3$) δ: 3.00-3.06(4H, m), 4.67(2H, d, J=6.0Hz), 6.43(1H, s), 6.79(1H, d, J=1.5Hz), 7.10-7.35(5H, m), 7.50-7.70(3H, m), 8.12-8.20(2H, m), 8.78(1H, s). |
| I-79 | 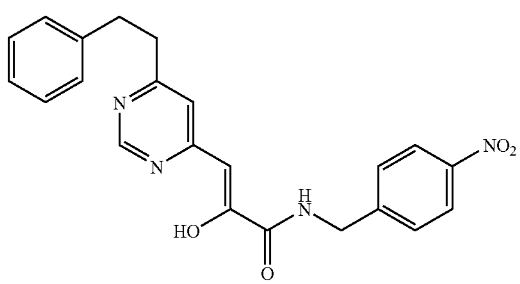 | (CDCl$_3$) δ: 3.00-3.06(4H, m), 4.67(2H, d, J=6.0Hz), 6.43(1H, s), 6.79(1H, d, J=1.5Hz), 7.15-7.35(5H, m), 7.49 and 8.21(2Hx2, ABq, J=8.7Hz), 7.60(1H, bs), 8.78(1H, s). |

TABLE 13

| Comp. No. | Structure | $^1$H-NMR |
|---|---|---|
| I-80 | 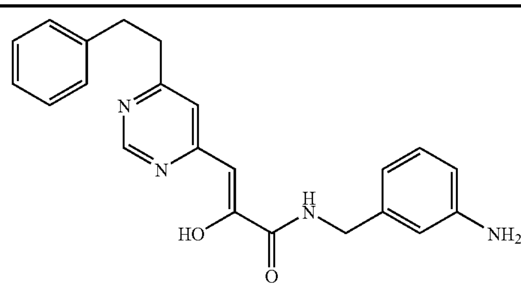 | (CDCl$_3$) δ: 3.00-3.06(4H, m), 4.47(2H, d, J=6.0Hz), 6.44(1H, s), 6.60-6.75(3H, m), 6.79(1H, d, J=1.5Hz), 7.10-7.35(6H, m), 7.38(1H, m), 8.78(1H, s). |

TABLE 13-continued
| Comp. No. | Structure | $^1$H-NMR |
|---|---|---|
| I-81 | 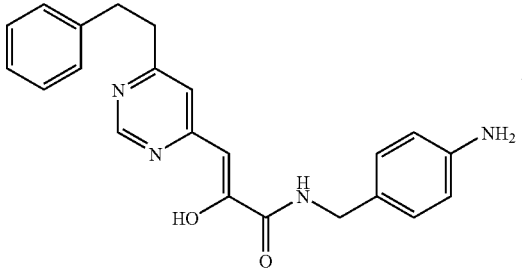 | (CDCl$_3$) δ: 3.00-3.06(4H, m), 4.44(2H, d, J=6.0Hz), 6.43(1H, s), 6.66(2H, d, J=8.1Hz), 6.79(1H, s), 7.10-7.38(8H, m), 8.78(1H, s). |
| I-82 | 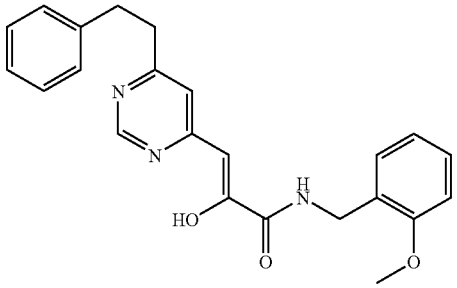 | (CDCl$_3$) δ: 3.00-3.06(4H, m), 3.89(3H, s), 4.56(2H, d, J=6.0Hz), 6.41(1H, s), 6.78(1H, d, J=1.5Hz), 6.88-6.96(2H, m) 7.15-7.32(7H, m), 7.56(1H, bs), 8.78(1H, d, J=1.5Hz). |
| I-83 | 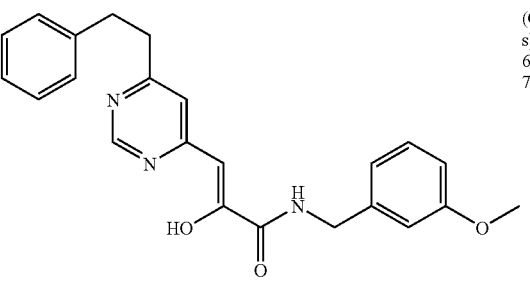 | (CDCl$_3$) δ: 3.00-3.06(4H, m), 3.81(3H, s), 4.54(2H, d, J=6.0Hz), 6.44(1H, s), 6.80-6.96(3H, m), 7.15-7.29(7H, m), 7.40(1H, bs), 8.78(1H, s). |

TABLE 13-continued

| Comp. No. | Structure | ¹H-NMR |
|---|---|---|
| I-84 | 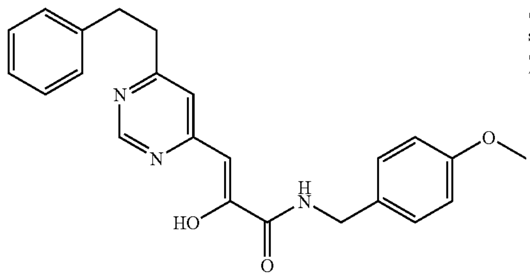 | (CDCl₃) δ: 3.00-3.06(4H, m), 3.80(3H, s), 4.50(2H, d, J=6.0Hz), 6.44(1H, s), 6.79(1H, s), 6.88(2H, d, J=8.0Hz), 7.15-7.40(8H, m), 8.78(1H, s). |
| I-85 | 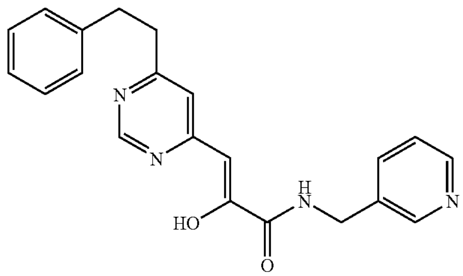 | (CDCl₃) δ: 3.00-3.06(4H, m), 4.60(2H, d, J=6.0Hz), 6.42(1H, s), 6.79(1H, d, J=1.5Hz), 7.15-7.40(6H,m), 7.49(1H, bs), 7.71(1H, d, J=8.1Hz), 8.56(1H, bs), 8.61(1H, bs), 8.78(1H, s). |

TABLE 14

| Comp. No. | Structure | ¹H-NMR |
|---|---|---|
| I-86 | 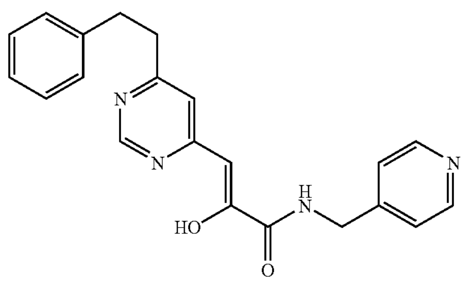 | (CDCl₃) δ: 3.00-3.06(4H, m), 4.61(2H, d, J=6.0Hz), 6.43(1H, s), 6.79(1H, d, J=1.5Hz), 7.15-7.38(7H, m), 7.53(1H, bs), 8.57(2H, bs), 8.78(1H, s). |

Example 87

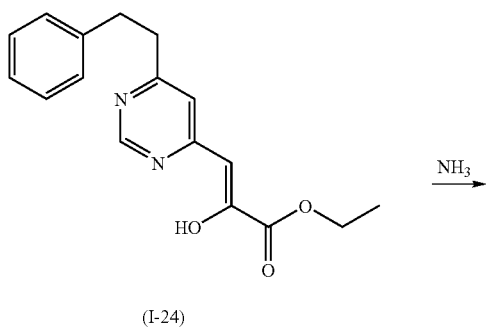

(I-24)

NH₃ →

-continued

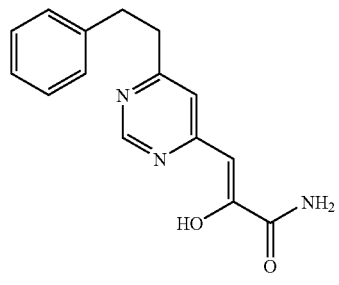

(I-87)

To Compound (I-24) (135 mg, 0.5 mmol) was added a solution of ammonia in ethanol (2.3N, 10 ml). The mixture was stirred for three days. To the mixture was added water. The mixture was extracted with chyloroform, washed with water, dried and concentrated. The obtained residue was chromatographed on silica gel (ethyl acetate-methanol). The obtained fraction was concentrated. The obtained crystal was washed with hexane and dried under reduced pressure to give Compound (I-87) (70 mg).

$^1$H-NMR (CDCl$_3$) δ: 3.00-3.05 (4H, m), 5.70 (1H, bs), 6.41 (1H, s), 6.80 (1H, d, J=1.2 Hz), 6.94 (1H, bs), 7.15-7.35 (5H, m), 8.83 (1H, d, J=1.2 Hz).

Example 88, 89 and 90

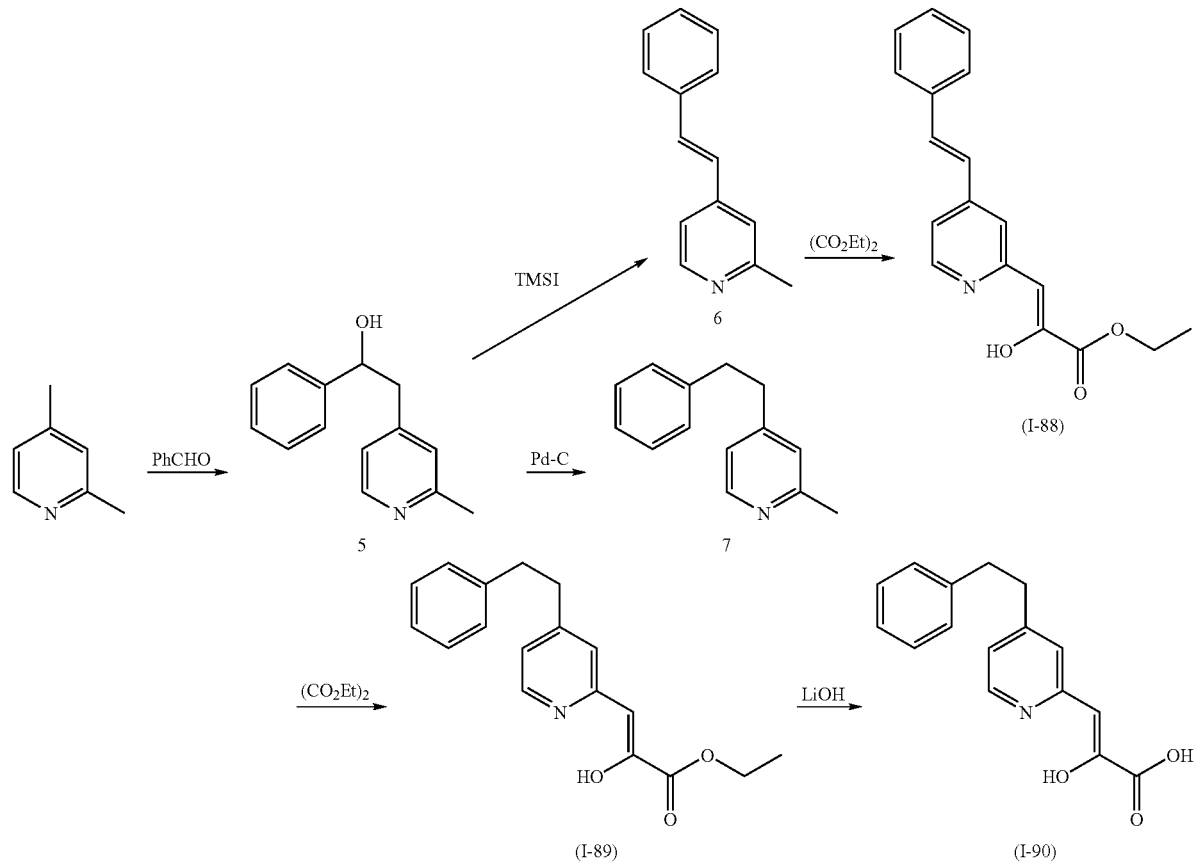

To a solution of 2,4-lutidine (1.07 g, 10 mmol) in methylene chloride (16 ml) was added at −78° C. 9-BBNOTf (0.5M in n-hexane, 10 mmol). To the solution were added diisopropylethylamine (1.55 g, 12 mmol) and benzaldehyde (1.06 g, 10 mmol). The mixture was stirred at room temperature for 4 hours. To the reaction mixture was added an aqueous solution of sodium hydrogencarbonate. The mixture was extracted with chloroform, washed with water, dried and concentrated. The obtained residue was chromatographed on silica gel (n-hexane-ethyl acetate). The obtained fraction was concentrated to give Compound 5 (1.48 g).

To a solution of sodium iodide (2.7 g, 18 mmol) and trimethylsilylchloride (2.0 g, 18 mmol) in acetonitrile (10 ml) was added Compound 5 (640 mg, 3 mmol). The mixture was stirred at room temperature for 3 hours. To the reaction mixture was added an aqueous solution of sodium hydrogencarbonate. The mixture was extracted with ethyl acetate, washed with water, dried and concentrated. The obtained crystal was washed with diethyl ether and dried under reduced pressure to give Compound 6 (400 mg).

To a solution of Compound 5 (853 mg, 4 mmol) in acetic acid was added a catalytic amount of palladium carbon. The mixture was stirred under hydrogen atmosphere for 38 hours. The reaction mixture was filtered off. The solvent was removed to give Compound 7 (560 mg).

Compound (I-88), (I-89) and (I-90) were added from Compound 6 and 7 in accordance with Example 2 and 3.

Compound (I-88)

$^1$H-NMR (CDCl$_3$) δ: 1.41 (3H, t, J=7.1 Hz), 4.39 (2H, q, J=7.1 Hz), 6.69 (1H, s), 7.04 (1H, d, J=16.5 Hz), 7.30-7.50 (6H, m), 7.55 (1H, s), 7.58 (1H, s), 8.34 (1H, d, J=7.2 Hz).

Compound (I-89)

$^1$H-NMR (CDCl$_3$) δ: 1.40 (3H, t, J=7.0 Hz), 2.98 (4H, s), 4.38 (2H, q, J=7.0 Hz), 6.65 (1H, s), 7.01 (1H, d, J=5.7 Hz), 7.13 (1H, d, J=7.2 Hz), 7.20-7.34 (5H, m), 8.29 (1H, d, J=5.4 Hz).

Compound (I-90)

$^1$H-NMR (d$_6$-DMSO) δ: 2.94 (4H, s), 6.40 (1H, s), 7.15-7.33 (7H, m), 8.35 (1H, d, J=5.4 Hz).

Example 91, 92, 93 and 94

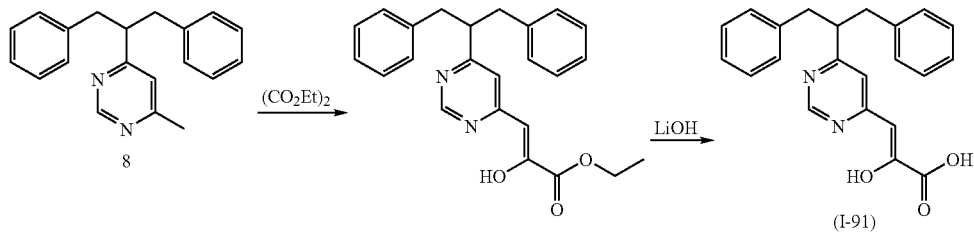

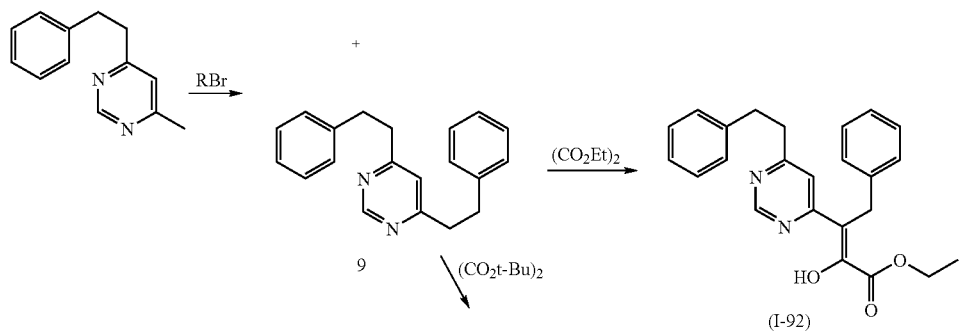

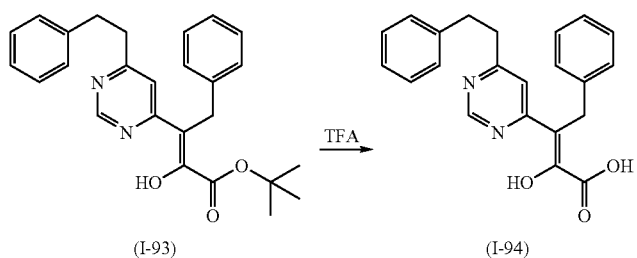

To a solution of 4-methyl-6-phenethylpyrimidine (1.98 g, 10 mmol) in THF (20 ml) was added dropwise at −78° C. n-butyllithium (10 mmol). To the reaction mixture was added benzylbromide (1.71 g, 10 mmol). The mixture was warmed up to room temperature and stirred for 30 minutes. To the reaction mixture was added an aqueous solution of ammonium chloride. The mixture was extracted with ethyl acetate, washed with water, dried and concentrated. The obtained residue was chromatographed on silica gel (n-hexane-ethyl acetate). The obtained fraction was concentrated under reduced pressure to give Compound 8 (478 mg) and 9 (1.61 g).

Compound (I-91) was prepared from the above-obtained Compound 8 in accordance with Example 2 and 3.

$^1$H-NMR (d$_6$-DMSO) δ: 2.90-3.10 (5H, m), 6.12 (1H, s), 6.98 (1H, s), 7.02-7.24 (10H, m), 8.90 (1H, s).

Compound (I-92) was prepared from the above-obtained Compound 9 in accordance with Example 2.

$^1$H-NMR (CDCl$_3$) δ: 1.31 (3H, t, J=7.1 Hz), 2.80-3.00 (4H, m), 3.89 (2H, s), 4.30 (2H, q, J=7.1 Hz), 6.78 (1H, s), 7.00-7.30 (10H, m), 8.84 (1H, s).

To a solution of Compound 9 (865 mg, 3 mmol) in THF (10 ml) was added dropwise at −78° C. n-butyllithium (3 mmol). To the reaction mixture was added oxalic acid di-tert-butyl ester (3.0 g, 15 mmol). The mixture was stirred for 30 minutes. To the reaction mixture was added an aqueous solution of ammonium chloride. The mixture was extracted with ethyl acetate, washed with water, dried and concentrated. The obtained residue was chromatographed on silica gel (n-hexane-ethyl acetate). The obtained fraction was concentrated under reduced pressure to give Compound (I-93) (780 mg).

$^1$H-NMR (CDCl$_3$) δ: 1.47 (9H, s), 2.91 (4H, s), 3.79 (2H, s), 6.69 (1H, s), 7.04-7.30 (10H, m), 8.77 (1H, s).

To a solution of Compound (I-93) (100 mg, 0.24 mmol) in methylene chloride (2 ml) was added TFA (1 ml). The mixture was stirred at room temperature for 5 hours. The solvent was removed under reduced pressure. The obtained crystal was washed with ethyl acetate and dried under reduced pressure to give Compound (I-94) (80 mg).

$^1$H-NMR (d$_6$-DMSO) δ: 2.88 (4H, s), 3.78 (2H, s), 6.95 (1H, s), 7.05-7.30 (10H, m), 8.81 (1H, s).

Example 95

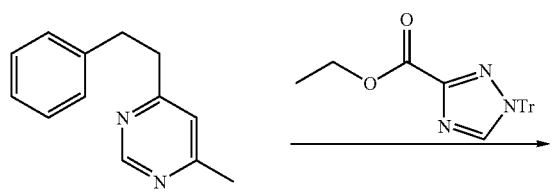

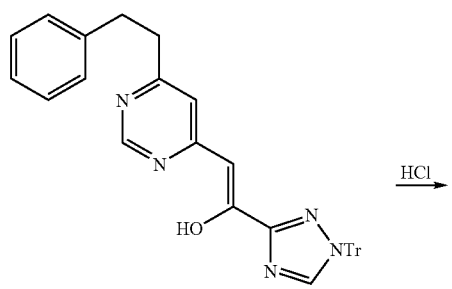

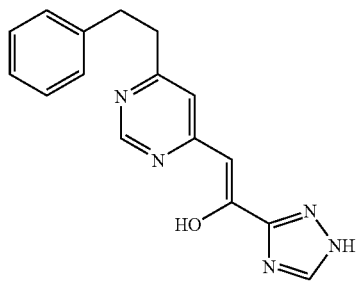

(I-95)

To a solution of 4-methyl-6-phenethylpyrimidine (595 mg, 3 mmol) in THF (15 ml) was added dropwise at −78° C. n-butyllithium (3 mmol). To the mixture was added 1-trityl-1H-[1,2,4]triazole-3-carboxylic acid ethylester (1.15 g, 3 mmol). The solution was warmed up to 0° C. and stirred for 30 minutes. To the reaction mixture was added an aqueous solution of ammonium chloride. The mixture was extracted with ethyl acetate, washed with water, dried and concentrated. The obtained crystal was washed with diethyl ether and dried under reduced pressure to give Compound 10 (906 mg).

To a solution of Compound 10 (200 mg, 0.37 mmol) in dioxane (5 ml) was added an aqueous solution of 1N—HCl (1 ml). The mixture was stirred at 50° C. for 30 minutes. To the solution was added at room temperature an aqueous solution of 1N-NaOH (1 ml). The mixture was extracted with ethyl acetate, washed with water, dried and concentrated. The obtained crystal was washed with diethyl ether and dried under reduced pressure to give Compound (I-95) (64 mg).

$^1$H-NMR (d$_6$-DMSO) δ: 2.90-3.05 (4H, m), 6.29 (1H, s), 7.08 (1H, s), 7.18-7.35 (5H, m), 8.35 (1H, bs), 8.75 (1H, s).

Example 96

The reaction was carried out in accordance with the above-shown process. Each structure and physical date of the compound is shown below.

TABLE 15

| Comp. No. | Structure | $^1$H-NMR |
|---|---|---|
| I-96 | 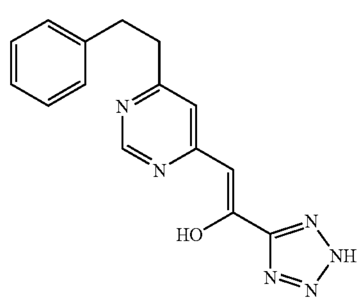 | (DMSO-d6) δ: 2.85-3.05(4H, m), 6.27(1H, s), 7.07(1H, s), 7.16-7.35(5H, m), 8.70(1H, s). |

Example 97

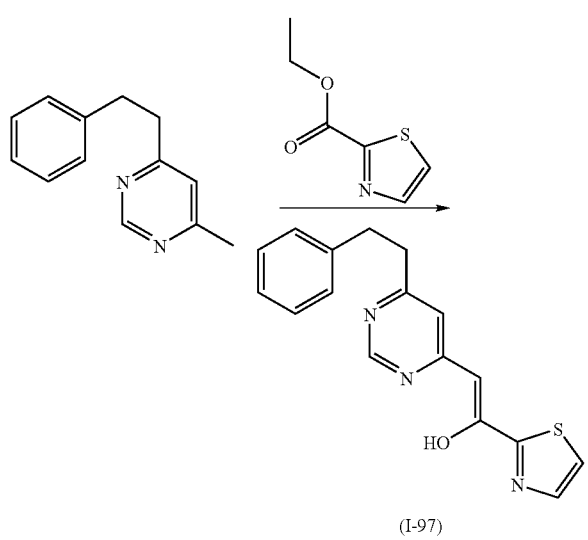

(I-97)

To a solution of 4-methyl-6-phenethylpyrimidine (595 mg, 3 mmol) in THF (10 ml) was added dropwise at −78° C. n-butyllithium (3 mmol). To the mixture was added thiazole-2-carboxylic acid ethylester (472 mg, 3 mmol). The solution was warmed up to 0° C. and stirred for 30 minutes. To the reaction mixture was added an aqueous solution of ammonium chloride. The mixture was extracted with ethyl acetate, washed with water, dried and concentrated. The obtained crystal was washed with diethyl ether and dried under reduced pressure to give Compound (I-97) (502 mg).

$^1$H-NMR (CDCl$_3$) δ: 3.00-3.07 (4H, m), 6.44 (1H, s), 6.70 (1H, s), 7.18-7.29 (5H, m), 7.53 (1H, d, J=3.0 Hz), 7.92 (1H, d, J=3.0 Hz), 8.67 (1H, s).

Example 98-105

Compounds were prepared in accordance with the above-shown Example. Each structure of ester derivative to be used and each structure and physical date of the compound are shown below.

TABLE 16

| Comp. No. | Ester | Structure | $^1$H-NMR |
|---|---|---|---|
| I-98 | EtOOC-isoxazole-O-CH$_2$-OCH$_3$ | [phenethyl-pyrimidine-CH=C(OH)-isoxazole-OEt] | (CDCl$_3$) δ: 3.06(4H, s), 3.57(3H, s), 5.36(2H, s), 6.08(1H, s), 6.42(1H, s), 6.80(1H, s), 7.18-7.29(5H, m), 8.83(1H, s). |
| I-99 | CF$_3$COOEt | [phenethyl-pyrimidine-CH=C(OH)-CF$_3$] | (CDCl$_3$) δ: 3.02-3.05(4H, m), 5.70(1H, s), 6.67(1H, s), 7.16-7.29(5H, m), 8.64(1H, s). |
| I-100 | PhOOC-P(O)(OEt)$_2$ | [phenethyl-pyrimidine-CH=C(OH)-P(O)(OEt)$_2$] | (CDCl$_3$) δ: 1.39(6H, t, J=7.1Hz), 3.07(4H, s), 4.19-4.26(4H, m), 6.24(1H, d, J=9.9Hz), 6.81(1H, s), 7.16-7.29(5H, m), 8.93(1H, s). |

TABLE 16-continued
| Comp. No. | Ester | Structure | ¹H-NMR |
|---|---|---|---|
| I-101 | 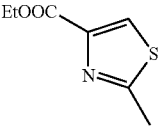 | 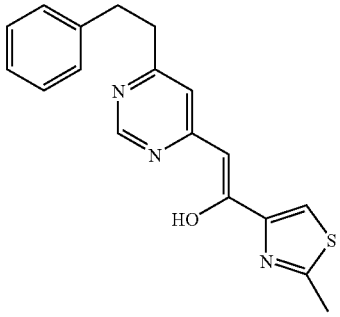 | (CDCl₃) δ: 2.75(3H, s), 2.96-3.10(4H, m), 6.37(1H, s), 6.76(1H, s), 7.15-7.32(5H, m), 7.70(1H, s), 8.82(1H, s). |
| I-102 | 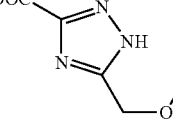 | 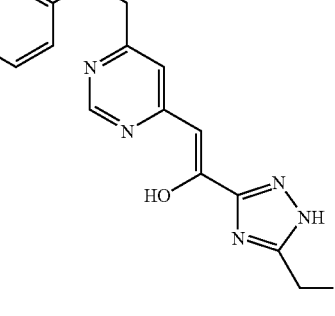 | (CDCl₃) δ: 2.98-3.10(4H, m), 3.50(3H, s), 4.64(2H, s), 6.43(1H, s), 6.70(1H, s), 7.16-7.33(5H, m), 8.77(1H, s). |
| I-103 | 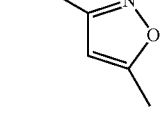 | 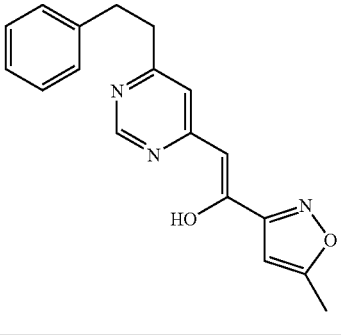 | (CDCl₃) δ: 2.48(3H, s), 2.95-3.08(4H, m), 6.16(1H, s), 6.34(1H, s), 6.71(1H, s), 7.18-7.35(5H, m), 8.77(1H, s). |
TABLE 17
| Comp. No. | Ester | Structure | ¹H-NMR |
|---|---|---|---|
| I-104 | 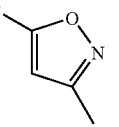 | 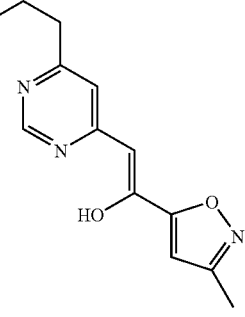 | (CDCl₃) δ: 2.36(3H, s), 3.00-3.08(4H, m), 6.11(1H, s), 6.56(1H, s), 6.79(1H, s), 7.18-7.36(5H, m), 8.82(1H, s). |

TABLE 17-continued

| Comp. No. | Ester | Structure | ¹H-NMR |
|---|---|---|---|
| I-105 | EtOOC-[pyrazine] | [structure] | (CDCl₃) δ: 3.00-3.12(4H, m), 6.67(1H, s), 6.84(1H, s), 7.16-7.32(5H, m), 8.59(1H, s), 8.62(1H, s), 8.90(1H, s), 9.21(1H, s). |

Example 106

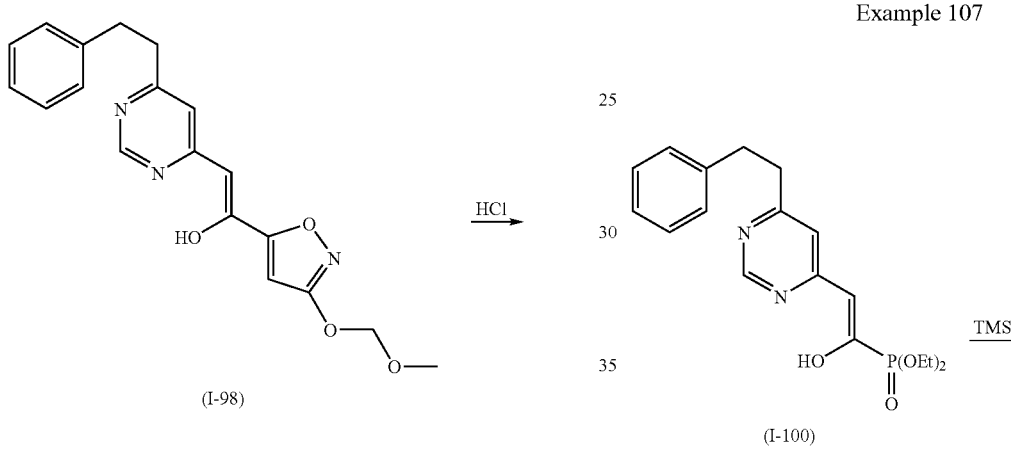

¹H-NMR (d₆-DMSO) δ: 2.91-3.01 (4H, m), 6.01 (1H, s), 6.41 (1H, s), 7.05 (1H, s), 7.18-7.28 (5H, m), 8.72 (1H, s).

Example 107

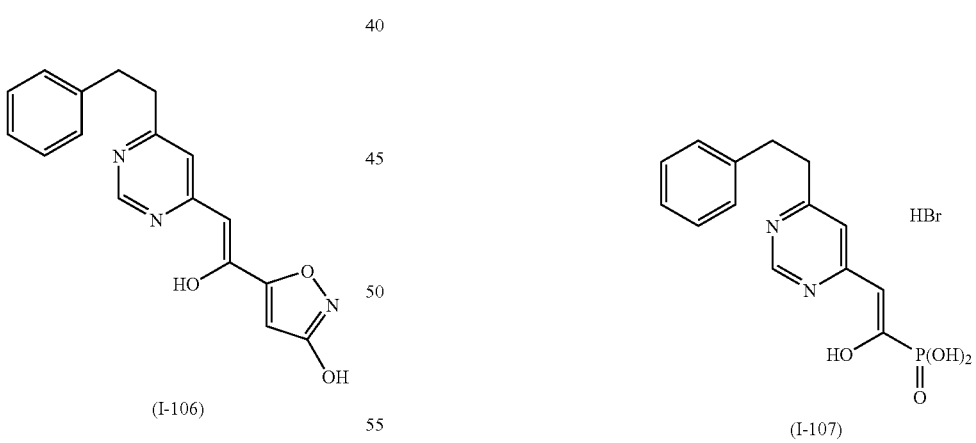

To a solution of Compound (I-98) (100 mg, 0.28 mmol) in methanol (5 ml) was added 3N hydrochloric acid (1 ml). The mixture was stirred at room temperature for 3 hours. To the reaction mixture was added water. The solution was alkalified with sodium hydrogencarbonate, washed with ethyl acetate and acidified with citric acid. The mixture was extracted with ethyl acetate, washed with water, dried and concentrated. The obtained crystal was washed with diethyl ether and dried under reduced pressure to give Compound (I-106) (44 mg).

To a solution of Compound (I-100) (40 mg, 0.11 mmol) in methylene chloride (2 ml) was added trimethylsilylbromide (135 mg, 0.88 mmol). The mixture was stirred at room temperature for 6 hours. The solvent and the remaining reagents were removed under reduced pressure. The obtained salt was washed with diethyl ether and dried under reduced pressure to give Compound (I-107) (41 mg).

$^1$H-NMR (d$_6$-DMSO) δ: 3.01 (3H, s), 6.06 (1H, d, J=9.0 Hz), 7.20-7.30 (6H, m), 8.95 (1H, s).

Example 108

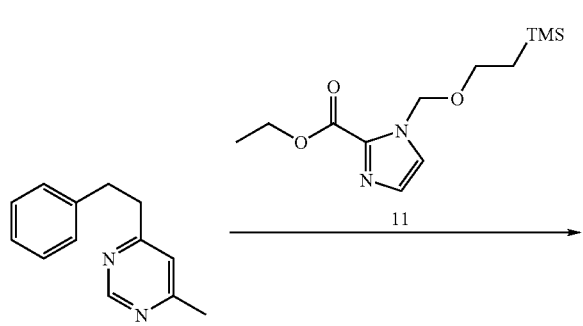

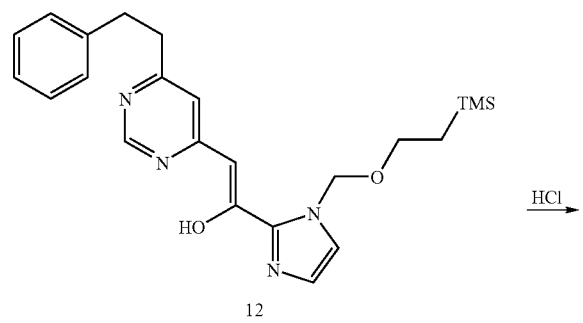

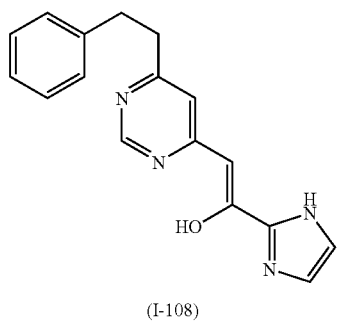

(I-108)

To a solution of 4-methyl-6-phenethylpyrimidine (293 mg, 1.48 mmol) in THF (10 ml) was added dropwise at −78° C. n-butyllithium (1.48 mmol). To the solution was added Compound 11 (400 mg, 1.48 mmol). The mixture was warmed up to 0° C. and stirred for 30 minutes. To the reaction mixture was added an aqueous solution of ammonium chloride. The mixture was extracted with ethyl acetate, washed with water, dried and concentrated to give Compound 12. To solution of Compound 12 in dioxane (3 ml) was added 3N hydrochloric acid (2 ml). The mixture was stirred at 70° C. for 1 hour. The solvent was removed under reduced pressure. To the solution was added water. The aqueous solution was alkalified with sodium hydrogencarbonate. The mixture was extracted with ethyl acetate, washed with water, dried and concentrated. The obtained crystal was washed with diethyl ether and dried under reduced pressure to give Compound (I-108) (10 mg).

$^1$H-NMR (CDCl$_3$) δ: 2.90-3.10 (4H, m), 6.56 (1H, s), 6.69 (1H, s), 7.10-7.30 (5H, m), 8.56 (1H, s), 9.09 (1H, s).

Example 109

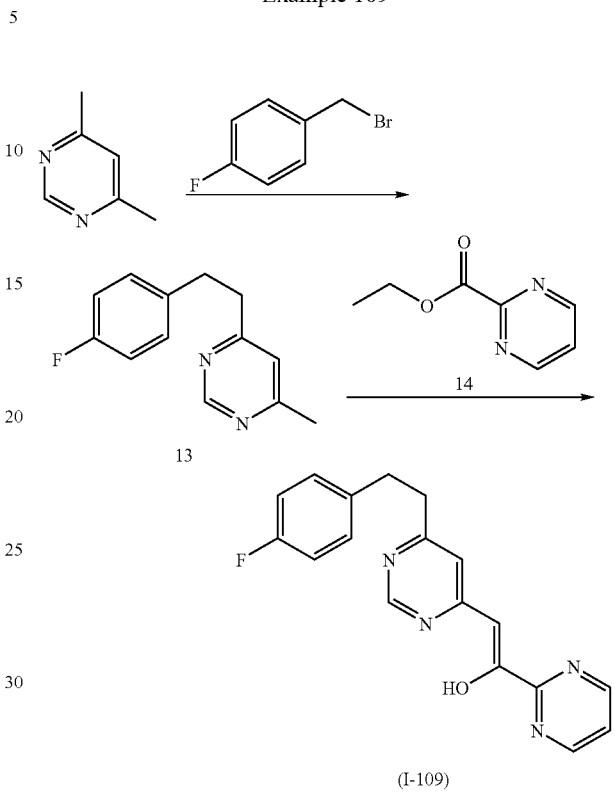

To a solution of 4,6-dimethylpyrimidine (2.95 g, 27.2 mmol) in THF (30 ml) was added dropwise at −78° C. n-butyllithium. To the solution was added p-fluorobenzylbromide (5.15 g, 27.2 mmol). The solution was warmed up to 0° C. and stirred for 30 minutes. To the solution was added water. The solution was acidified with hydrochloric acid. The aqueous solution was washed with n-hexane and alkalified with an aqueous solution of sodium hydroxide. The mixture was extracted with diethyl ether, washed with water, dried and concentrated under reduced pressure to give Compound 13 (4.03 g).

To a solution of Compound 13 (430 mg, 2 mmol) in THF (3 ml) were added under ice-cooling Compound 14 (280 mg, 2 mmol) and potassium t-butoxide (450 mg, 4 mmol). The solution was warmed up to room temperature and stirred for 10 minutes. To the reaction mixture was added an aqueous solution of ammonium chloride. The mixture was extracted with ethyl acetate, washed with water, dried and concentrated. The obtained crystal was washed with diethyl ether and dried under reduced pressure to give Compound (I-109) (250 mg).

$^1$H-NMR (CDCl$_3$) δ: 3.00-3.06 (4H, m), 6.86-7.02 (4H, m), 7.10-7.18 (2H, m), 7.29-7.34 (1H, m), 8.87 (2H, d, J=1.5 Hz), 8.99 (1H, s).

Example 110, 111

Compounds were prepared from 4-methyl-6-phenethylpyrimidine in accordance with Example 109. Each structure and physical date of the compound are shown below.

TABLE 18

| Comp. No. | Structure | ¹H-NMR |
|---|---|---|
| I-110 | 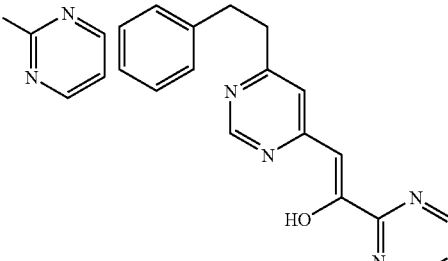 | (CDCl$_3$) δ: 3.00-3.06(4H, m), 6.89(1H, s), 6.90(1H, d, J=1.5Hz), 7.18-7.35(6H, m), 8.86(2H, d, J=5.1Hz), 8.99(1H, s). |
| I-111 | 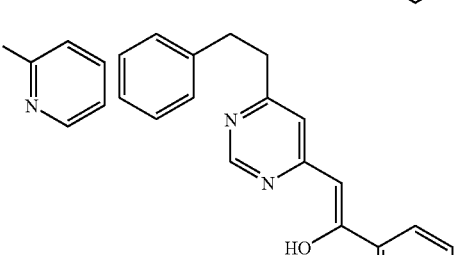 | (CDCl$_3$) δ: 3.00-3.06(4H, m), 6.70(1H, s), 6.83(1H, d, J=1.2Hz), 7.08-7.40(6H, m), 7.81(1H, dt, J=7.8, 1.5Hz), 8.01(1H, d, J=7.8Hz), 8.64(1H, d, J3.6Hz), 8.86(2H, d, J=1.5Hz). |

Example 112, 113, 114

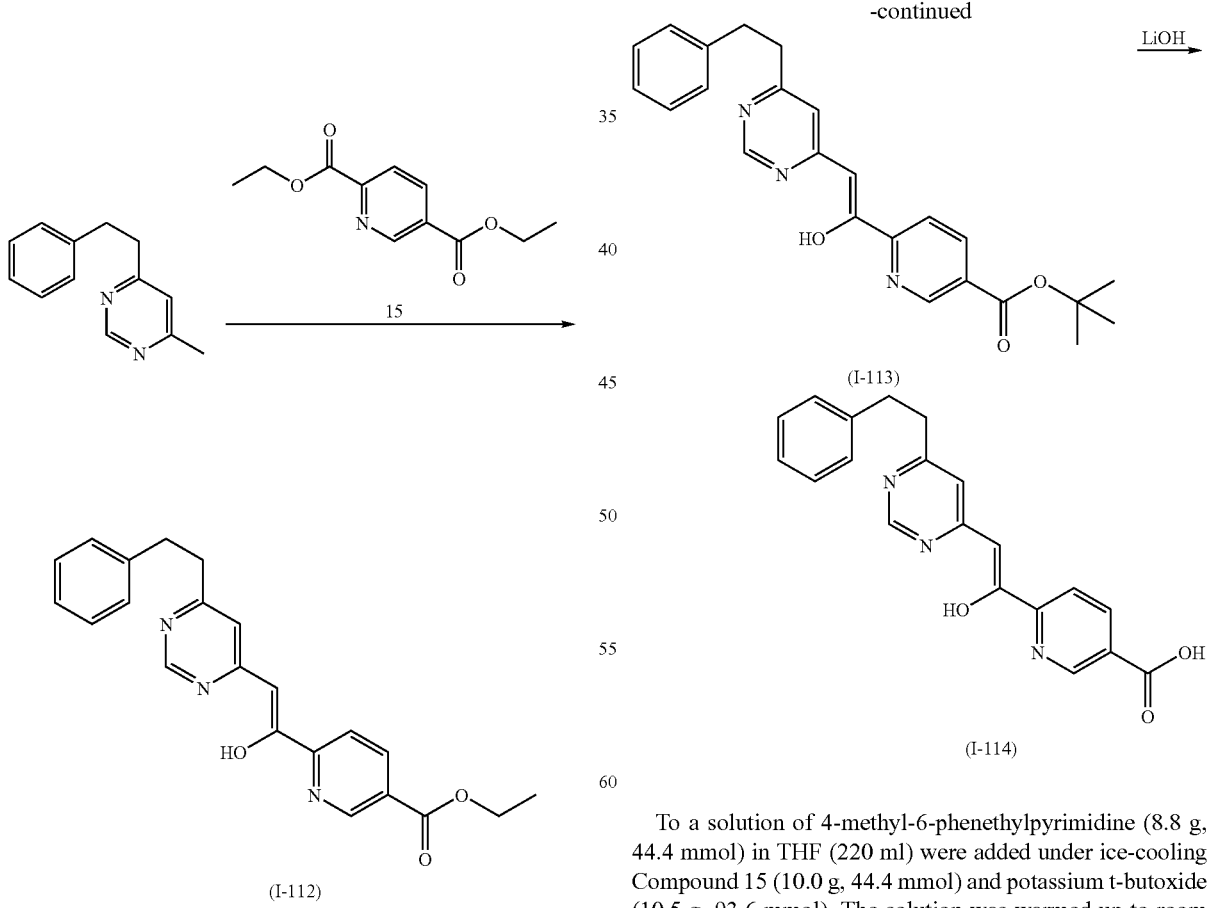

To a solution of 4-methyl-6-phenethylpyrimidine (8.8 g, 44.4 mmol) in THF (220 ml) were added under ice-cooling Compound 15 (10.0 g, 44.4 mmol) and potassium t-butoxide (10.5 g, 93.6 mmol). The solution was warmed up to room temperature and stirred for 10 minutes. To the reaction mixture was added an aqueous solution of ammonium chloride.

The mixture was extracted with ethyl acetate, washed with water, dried and concentrated. The obtained residue was chromatographed on silica gel (n-hexane-ethyl acetate). The obtained fraction was concentrated under reduced pressure to give Compound (I-113) (580 mg).

Compound (I-112)

¹H-NMR (CDCl₃) δ: 1.43 (3H, t, J=7.2 Hz), 3.00-3.06 (4H, m), 4.44 (2H, q, J=7.2 Hz), 6.81 (1H, s), 6.88 (1H, d, J=1.2 Hz), 7.16-7.30 (6H, m), 8.05 (1H, dd, J=8.4, 0.9 Hz), 8.40 (1H, dd, J=8.4, 2.4 Hz), 8.90 (1H, d, J=0.9 Hz), 9.21 (1H, dd, J=2.1, 0.9 Hz).

Compound (I-113)

¹H-NMR (CDCl₃) δ: 1.62 (9H, s), 6.79 (1H, s), 6.87 (1H, d, J=1.2 Hz), 7.16-7.30 (6H, m), 8.03 (1H, dd, J=8.4, 0.6 Hz), 8.33 (1H, dd, J=8.4, 2.1 Hz), 8.90 (1H, d, J=0.6 Hz), 9.15 (1H, dd, J=2.1, 0.9 Hz).

To a solution of Compound (I-112) (1.38 g, 3.68 mmol) in methanol (50 ml) was added an aqueous solution of lithium hydroxide (1N, 14 ml). The solution was refluxed for 1 hour. Methanol was removed under reduced pressure. To the residue was added methanol. The aqueous solution was acidified with citric acid. The mixture was extracted with ethyl acetate, washed with water, dried and concentrated. The obtained crystal was washed with diethyl ether and dried under reduced pressure to give Compound (I-114) (950 mg).

¹H-NMR (d6-DMSO) δ: 6.81 (1H, s), 6.81 (1H, s), 7.16-7.35 (6H, m), 8.05 (1H, d, J=8.4 Hz), 8.41 (1H, m), 8.88 (1H, s), 9.10 (1H, m).

Example 115

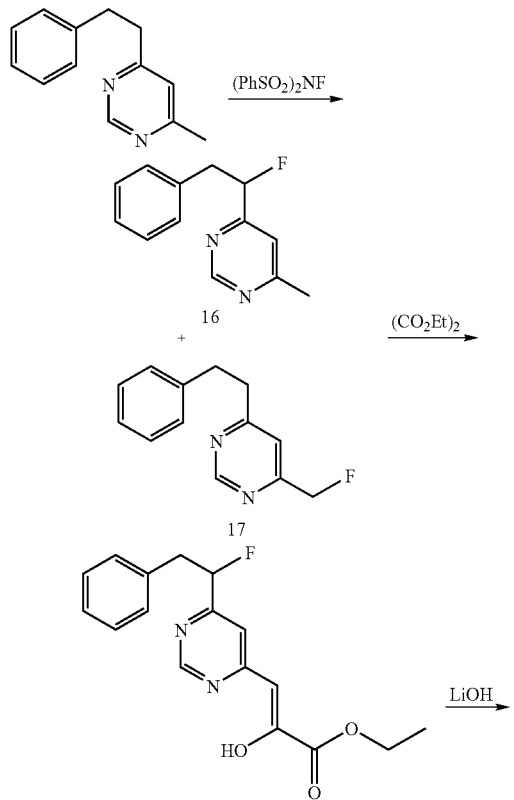

To a solution of 4-methyl-6-phenethylpyrimidine (1.3 g, 6.6 mmol) in THF (15 ml) was added dropwise at −78° C. n-butyllithium (6.6 mmol). To the solution was added N-fluorobenzenesulfone imide (2.3 g, 7.2 mmol). The mixture was warmed up to room temperature and stirred for 30 minutes. To the reaction mixture was added an aqueous solution of ammonium chloride. The mixture was extracted with ethyl acetate, washed with water, dried and concentrated. The obtained residue was chromatographed on silica gel (n-hexane-ethyl acetate). The obtained fraction was concentrated under reduced pressure to give a mixture of Compound 16 and 17 (1.3 g).

Compound (I-115) was prepared from the above-obtained mixture in accordance with Example 2, 3.

¹H-NMR (d6-DMSO) δ: 3.10-3.41 (2H, m), 5.77 (1H, ddd, J=4.2, 8.7, 48.6 Hz), 6.38 (1H, s), 7.21-7.32 (5H, m), 7.50 (1H, s), 8.98 (1H, s).

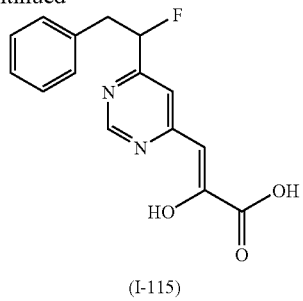

(I-115)

Example 116, 117

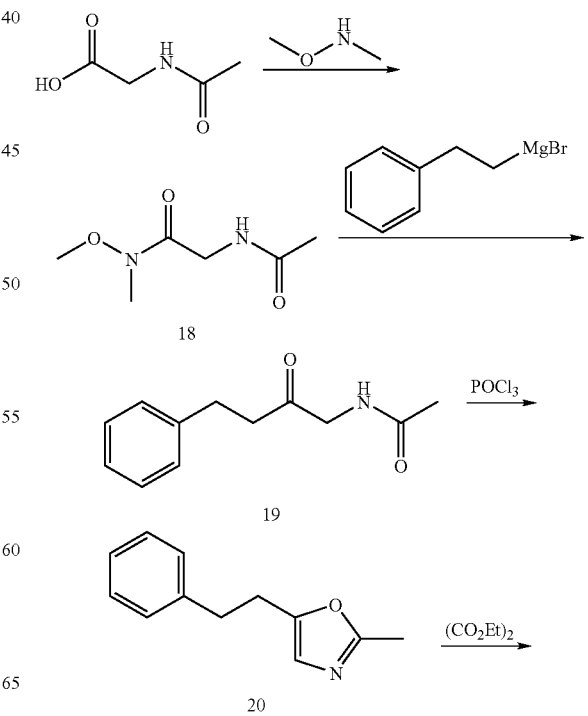

-continued

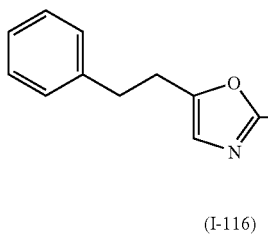

To a solution of N-acetylglycine (3.51 g, 30 mmol) in chloroform (30 ml) and acetonitrile (10 ml) were added N,O-dimethylhydroxyamine hydrochloride (3.22 g, 33 mmol), HOBt (4.46 g, 30 mmol), WSCD (5.59 g, 36 mmol) and triethylamine (3.34 g, 33 mmol). The mixture was stirred at room temperature for 3 hours. The solvent was removed. The obtained residue was chromatographed on silica gel (chloroform-ethanol). The obtained fraction was concentrated under reduced pressure to give Compound 18 (4.10 g).

To a solution of Compound 18 (4.40 g, 27.5 mmol) in THF (30 ml) was added under ice-cooling phenethylmagnesiumbromide (1M in THF, 60 mmol). The mixture was warmed up to room temperature and stirred for 30 minutes. To the reaction mixture was added an aqueous solution of ammonium chloride. The mixture was extracted with ethyl acetate, washed with water, dried and concentrated. The obtained residue was chromatographed on silica gel (chloroform-methanol). The obtained fraction was concentrated under reduced pressure to give Compound 19 (3.56 g).

To a solution of Compound 19 (1.5 g, 7.3 mmol) in toluene was added phosphorus oxychloride (3 g). The mixture was refluxed for 1 hour. The solvent was removed. The obtained residue was chromatographed on silica gel (n-hexane-ethyl acetate). The obtained fraction was concentrated under reduced pressure to give Compound 20 (1.1 g).

Compound (I-116) was prepared from Compound 20 in accordance with Example 2.

$^1$H-NMR (CDCl$_3$) δ: 1.39 (3H, t, J=7.2 Hz), 2.99 (4H, s), 4.36 (2H, q, J=7.2 Hz), 6.53 (1H, s), 6.79 (1H, s), 7.13-7.35 (5H, m).

To a solution of Compound (E-1) (50 mg, 0.17 mmol) in dioxane (3 ml) was added 3N hydrochloric acid (3 ml). The mixture was warmed up to 50° C. and stirred for 3 hours. To the solution was added water. The aqueous solution was alkalified with sodium hydrogencarbonate. The solution was washed with chloroform and acidified with citric acid. The mixture was extracted with ethyl acetate, washed with water, dried and concentrated to give Compound (I-117) (31 mg).

$^1$H-NMR (d$_6$-DMSO) δ: 2.85-3.05 (4H, m), 6.37 (1H, s), 7.05 (1H, s), 7.10-7.32 (5H, m).

Example 118, 119

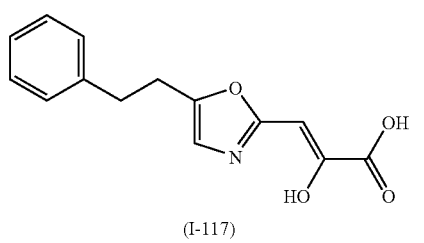

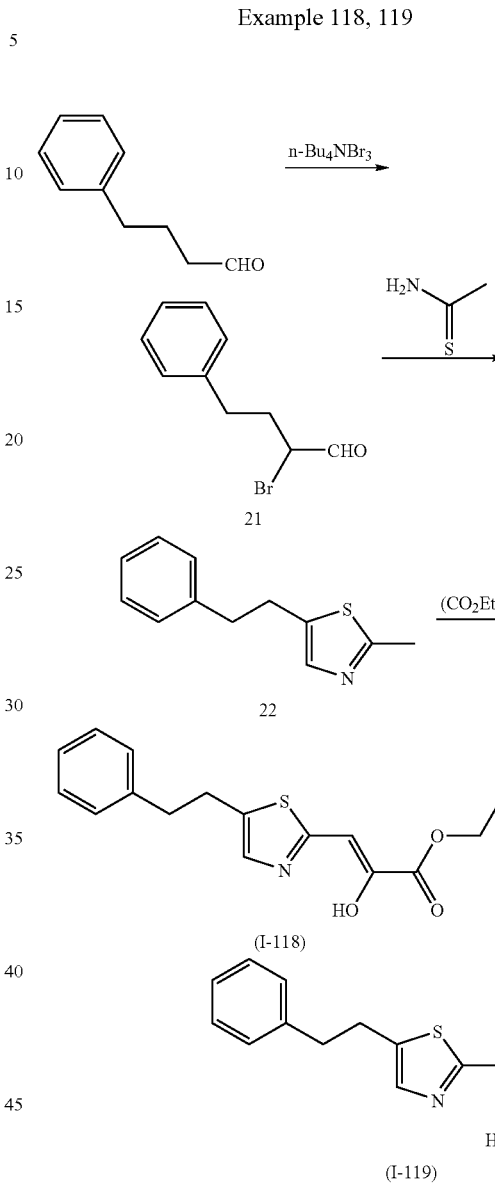

To a solution of 4-phenyl-1-butanal (1.48 g, 10 mmol) in acetonitrile (50 ml) was added tetrabutylammoniumtribromide (4.82 g, 10 mmol). The mixture was stirred at 50° C. for 30 minutes. To the solution was added water. The mixture was extracted with diethyl ether, washed with water, dried and concentrated to give Compound 21 (2.21 g).

To a solution of Compound 21 (1.0 g, 4.4 mmol) in acetonitrile (10 ml) was added thioacetamide (660 mg, 8.8 mmol). The mixture was refluxed for 2 hours. To the reaction mixture was added an aqueous solution of sodium hydrogencarbonate. The mixture was extracted with diethyl ether, washed with water, dried and concentrated. The obtained residue was chromatographed on silica gel (n-hexane-ethyl acetate). The obtained fraction was concentrated under reduced pressure to give Compound 22 (750 mg).

Compound (I-118) and (I-119) were prepared from Compound 22 in accordance with Example 2 and 3.

Compound (I-118)

$^1$H-NMR (CDCl$_3$) δ: 1.38 (3H, t, J=7.2 Hz), 2.97 (2H, t, J=7.7 Hz), 3.16 (2H, t, J=7.7 Hz), 4.35 (2H, q, J=7.2 Hz), 6.69 (1H, s), 7.15-7.38 (5H, m), 7.42 (1H, s).

Compound (I-119)

$^1$H-NMR (d$_6$-DMSO) δ: 2.93 (2H, t, J=8.0 Hz), 3.12 (2H, t, J=8.0 Hz), 6.63 (1H, s), 7.18-7.38 (5H, m), 7.48 (1H, s).

Example 120, 121

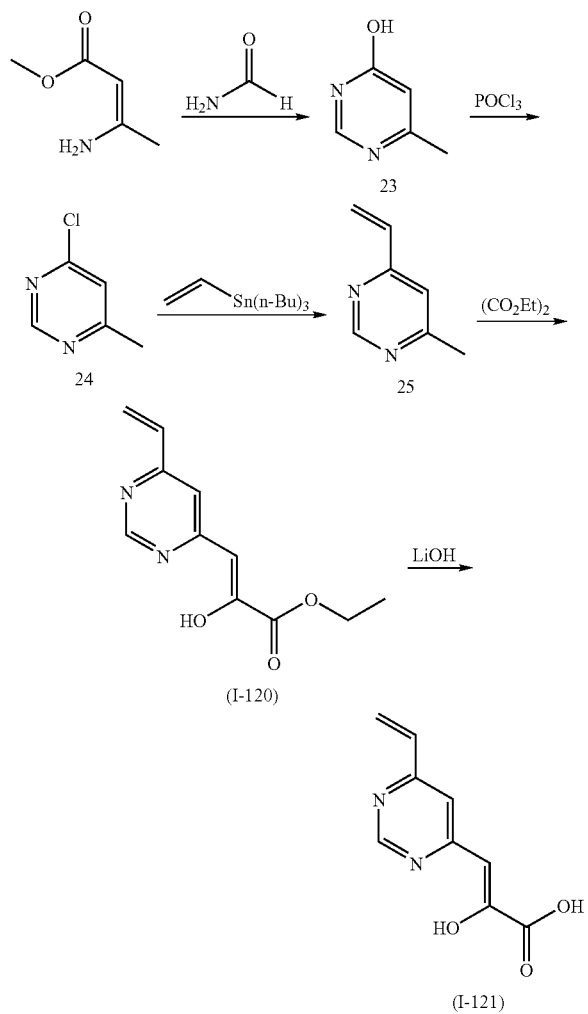

To a solution of 30% sodium methoxide in methanol (275 mmol) were added methyl-3-aminocrotonate (12.5 g, 110 mmol) and formamide (50 g, 1.1 mol). The mixture was refluxed for 3 hours. Methanol was removed. To the residue was added THF (100 ml). The supernatant liquid was removed. This procedure was carried out three times. To the residue were added methanol and ammonium chloride (16 g). The insoluble product was filtered off. The solvent was removed under reduced pressure to give 23 (10.5 g).

To a solution of Compound 23 (10.45 g, 95 mmol) was added phosphorus oxychloride (50 g). The mixture was stirred at 110° C. for 20 minutes. The reaction mixture was poured into ice water. The aqueous solution was alkalified with sodium hydroxide. The mixture was extracted with diethyl ether, washed with water, dried and concentrated to give Compound 24 (8.35 g).

To a solution of Compound 24 (6.95 g, 54 mmol) in N-methylpyrrolidone were added tributyltinvinylate (18 g, 57 mmol) and Pd(Ph$_3$)$_4$ (3.1 g, 2.7 mmol). The mixture was added at 80° C. for 3 hours. To the reaction mixture was added an aqueous solution of sodium hydrogencarbonate. The mixture was extracted with diethyl ether, washed with water, dried and concentrated. The obtained residue was chromatographed on silica gel (diethyl ether). The obtained fraction was concentrated under reduced pressure to give Compound 25 (5.51 g).

Compounds (I-120) and (I-121) were prepared from Compound 25 in accordance with Example 112 and 114.

Compound (I-120)

$^1$H-NMR (CDCl$_3$) δ: 1.40 (3H, t, J=7.4 Hz), 4.37 (2H, q, J=7.4 Hz), 5.74 (1H, dd, J=10.8, 1.5 Hz), 6.45 (1H, s), 6.50 (1H, dd, J=17.1, 1.5 Hz), 6.71 (1H, dd, J=17.1, 10.8 Hz), 8.89 (1H, s).

Compound (I-121)

$^1$H-NMR (d$_6$-DMSO) δ: 5.74 (1H, d, J=11.0 Hz), 6.28 (1H, s), 6.47 (1H, d, J=17.0 Hz), 6.74 (1H, dd, J=11.0, 17.0 Hz), 7.40 (1H, s), 8.82 (1H, s).

Example 122, 123, 124

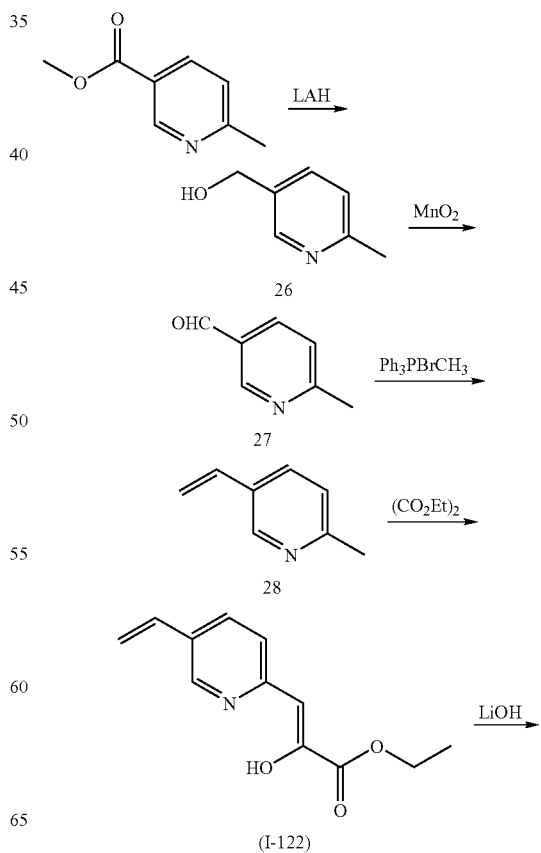

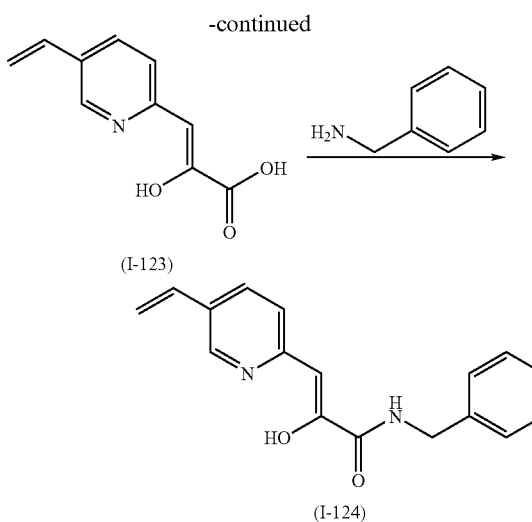

To a solution of lithiumaluminumhydride (2.5 g, 66 mmol) in THF (100 ml) was added under ice-cooling 6-methyl nicotinic acid methyl ester (10 g, 66 mmol). The mixture was warmed up to room temperature and stirred for 10 minutes. To the solution was added under ice-cooling ethyl acetate and water. The solution was stirred until the generation of hydrogen gas was finished. The solvent was removed. The solution was mixed with chloroform, dried and concentrated. The obtained residue was chromatographed on silica gel (ethyl acetate). The obtained fraction was concentrated under reduced pressure to give Compound 26 (7.9 g).

To a solution of Compound 26 (7.9 g, 64 mmol) in chloroform (100 ml) was added manganese dioxide (27.9 g, 321 mmol). The mixture was stirred at 60° C. for 1 hour. The reaction solution was filtered off. The solvent was removed to give Compound 27 (7.1 g).

To a solution of methyltriphenylphosphoniumbromide (22.0 g, 61.5 mmol) in THF (50 ml) was added dropwise under ice-cooling n-butyllithium (61.5 mmol). The mixture was stirred for 30 minutes. To the solution was added dropwise a solution of Compound 27 (7.1 g, 58.6 mmol) in THF (20 ml). The mixture was warmed up to room temperature and stirred for 1 hour. To the solution was added water. The mixture was extracted with diethyl ether, washed with water, dried and concentrated. The obtained residue was chromatographed on silica gel (n-hexane-ethyl acetate). The obtained fraction was concentrated under reduced pressure to give Compound 28 (8.0 g).

To a solution of Compound 28 (7.0 g, 58.6 mmol) in THF (200 ml) were added oxalic acid diethyl ester (85.7 g, 58.6 mmol) and potassium t-butoxide (13.2 g, 58.6 mmol). The mixture was refluxed for 4 hours. To the reaction mixture was added an aqueous solution of ammonium chloride. The mixture was extracted with ethyl acetate, washed with water, dried and concentrated. The obtained crystal was washed with n-hexane and dried under reduced pressure to give Compound (I-122) (5.7 g).

$^1$H-NMR (CDCl$_3$) δ: 1.40 (3H, t, J=7.1 Hz), 4.36 (2H, q, J=7.1 Hz), 5.40 (1H, d, J=11.0 Hz), 5.83 (1H, d, J=17.6 Hz), 6.56 (1H, s), 6.69 (1H, dd, J=11.0, 17.6 Hz), 7.18 (1H, d, J=8.2 Hz), 7.79 (1H, dd, J=2.2, 8.0 Hz), 8.43 (1H, d, J=2.2 Hz).

Compound (I-123) was prepared from Compound (I-122) in accordance with Example 3.

$^1$H-NMR (d$_6$-DMSO) δ: 5.42 (1H, d, J=11.3 Hz), 6.01 (1H, d, J=17.7 Hz), 6.56 (1H, s), 6.77 (1H, dd, J=11.3, 17.7 Hz), 7.50 (1H, d, J=8.5 Hz), 8.07 (1H, d, J=2.1, 8.5 Hz), 8.60 (1H, d, J=1.8 Hz).

Compound (I-124) was prepared from Compound (I-123) in accordance with Example 60.

$^1$H-NMR (CDCl$_3$) δ: 4.60 (2H, d, J=6.0 Hz), 5.38 (1H, d, J=11.1 Hz), 5.80 (1H, d, J=17.7 Hz), 6.60 (1H, s), 6.66 (1H, dd, J=11.1, 17.7 Hz), 7.18 (1H, d, J=8.4 Hz), 7.20-7.42 (5H, m), 7.78 (1H, dd, J=2.4, 8.7 Hz), 8.26 (1H, d, J=2.4 Hz).

Example 125, 126

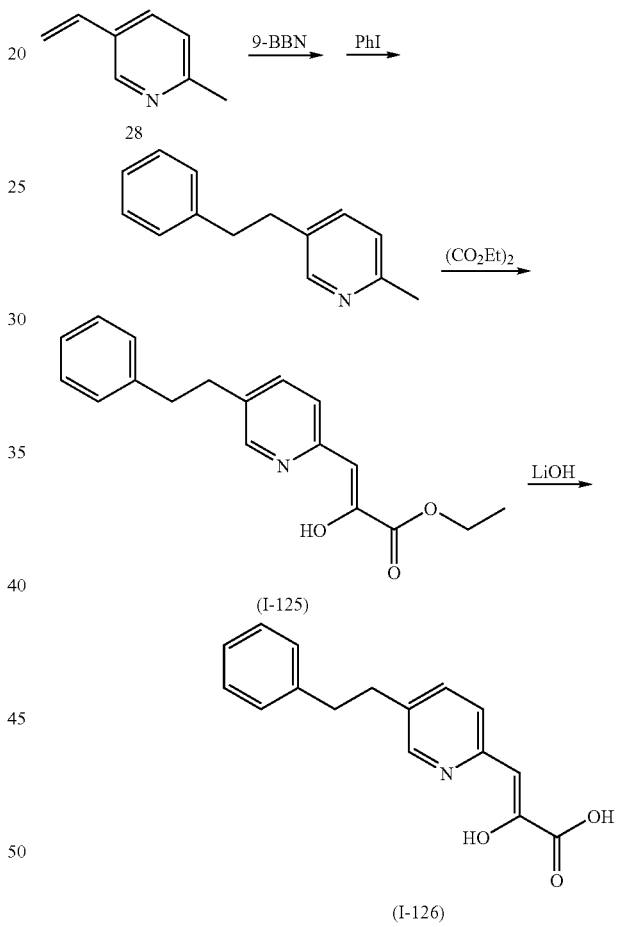

To a solution of Compound 28 (330 mg, 2.8 mmol) in THF (2 ml) was added 9-BBN (0.5M in THF, 5.5 mmol). The mixture was stirred at 60° C. for 3 hours. The mixture was cooled to room temperature. To the solution were added iodobenzene (1.7 g, 8.3 mmol), a solution of sodium hydroxide (3M, 8.3 mmol) and PdCl2(dppf) (226 mg, 0.3 mmol). The mixture was stirred at 50° C. for 3 hours. To the mixture was added water. The mixture was extracted with ethyl acetate, washed with water, dried and concentrated. The obtained residue was chromatographed on silica gel (n-hexane-ethyl acetate). The obtained fraction was concentrated under reduced pressure to give 2-methyl-5-phenethylpyridine (540 mg).

Compounds (I-125) and (I-126) were prepared from the above obtained 2-methyl-5-phenethylpyridine in accordance with Example 2 and 3.

Compound (I-125)
$^1$H-NMR (CDCl$_3$) δ: 1.39 (3H, t, J=7.1 Hz), 4.35 (2H, q, J=7.1 Hz), 6.54 (1H, s), 7.08-7.32 (6H, m), 7.47 (1H, dd, J=2.1, 7.8 Hz), 8.20 (1H, d, J=2.4 Hz).

Compound (I-126)
$^1$H-NMR (d$_6$-DMSO) δ: 2.92 (4H, s), 6.52 (1H, s), 7.15-7.31 (5H, m), 7.42 (1H, d, J=8.4 Hz), 7.77 (1H, dd, J=2.1, 8.1 Hz), 8.36 (1H, d, J=2.1 Hz).

Example 127 and 128

Compounds were prepared by using 2-isopropyliodobenzene in accordance with the above-shown process. Each structure and physical date of the compound is shown below.

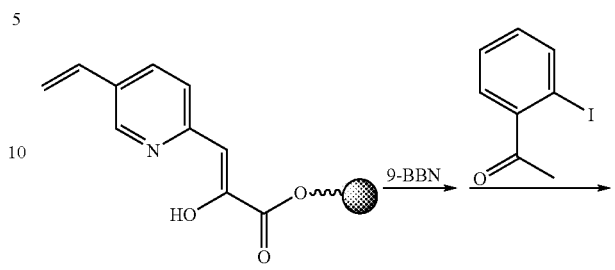

Resin A

TABLE 19

| Comp. No. | Structure | $^1$H-NMR |
|---|---|---|
| I-127 | 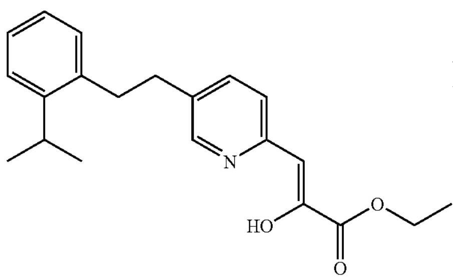 | (CDCl$_3$) δ: 1.21(6H, d, J=6.7Hz), 1.39(3H, t, J-7.0Hz), 2.80-3.00(4H, m), 3.00-3.18(1H, m), 4.35(2H, q, J=7.0), 6.54(1H,s ), 7.00-7.30(5H, m), 7.48(1H, dd, J=2.1, 5.8Hz), 8.21(1H, d, J=2.1Hz). |
| I-128 | 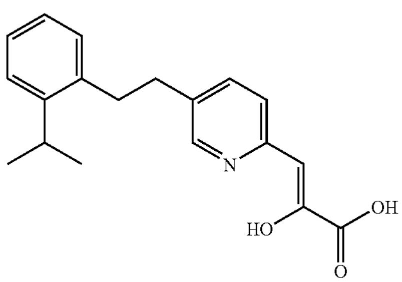 | (DMSO-d6) δ: 1.14(6H, d, J=6.9Hz), 2.80-3.00(4H, m), 3.00-3.20(1H, m), 6.52(1H, s), 7.05-7.30(4H, m), 7.43(1H, d, J=8.0Hz), 7.76(1H, dd, J=2.2, 6.0Hz), 8.35(1H, d, J=2.2Hz). |

Example 129

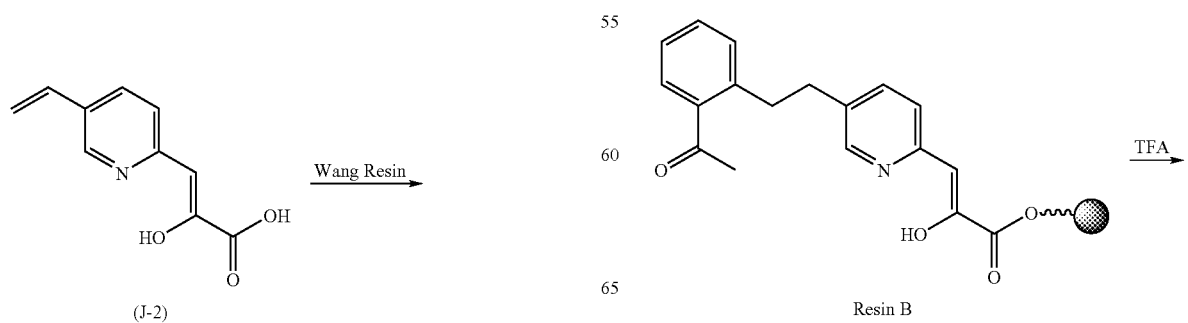

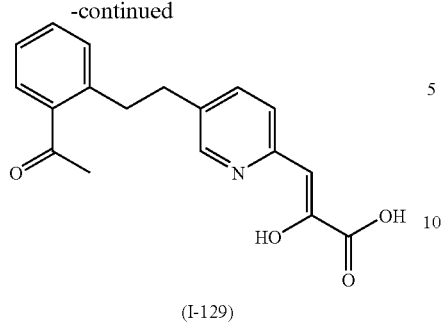

(I-129)

To Wang Resin (5.59 g, 0.65 mmol/g) was added DMF (80 ml). To the mixture was added Compound (J-2) (1.39 g, 7.27 mmol), HOBt (982 mg, 7.27 mmol), N-methylmorpholine (1.47 g, 14.5 mmol) and PyBop (3.78 g, 7.27 mmol). The mixture was stirred at room temperature for 24 hours. The obtained resin was washed with DMF, water, methanol and methylene chloride and dried under reduced pressure to give Resin A (5.84 g).

To Resin A (30 mg) was added THF (0.4 ml). To the mixture was added 9-BBN (0.5M in THF, 0.4 ml). The mixture was stirred at room temperature for 4 hours. To the mixture was added an aqueous solution of potassium carbonate (2M, 0.1 ml), 2-acetyliodobenzene (41 mg, 0.2 mmol) and PdCl$_2$(dppf) (3 mg). The mixture was stirred at 50° C. for 20 hours. The obtained resin was washed with DMF, water, methanol and methylene chloride to give Resin B.

To Resin B was added a 20% solution of TFA in methylene chloride. The mixture was stirred at room temperature for 1 hour. The reaction solvent was removed under reduced pressure to give Compound (I-129). Identification of the product was carried out by measuring [M+H]+ of LC-Ms spectrum analysis.

Example 130-174

Compounds were prepared by using various halogenated compounds in accordance with the above method. Each structure of ester derivative to be used the compounds is shown below. Each product was identified by measuring [M+H]+ of LC-Ms spectrum analysis.

TABLE 20

| Comp. No. | Halogenated compound (starting compound) | Structure |
|---|---|---|
| I-130 | | 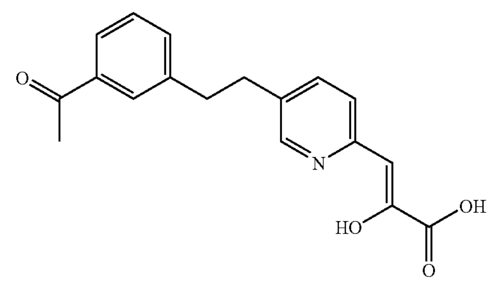 |
| I-131 | | 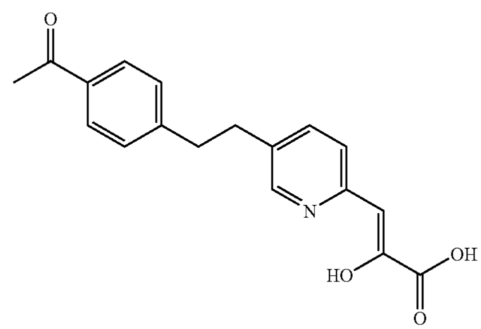 |
| I-132 | | 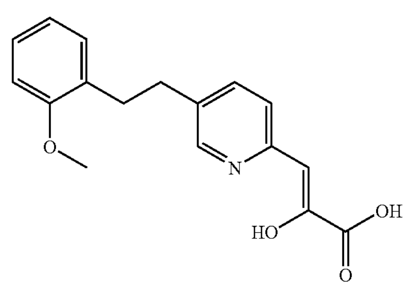 |

TABLE 20-continued
| Comp. No. | Halogenated compound (starting compound) | Structure |
|---|---|---|
| I-133 |  | 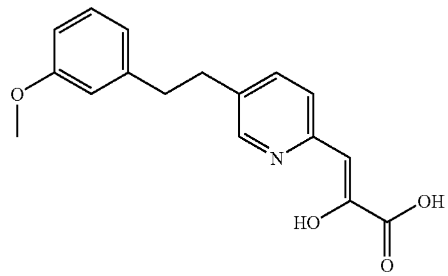 |
| I-134 | | 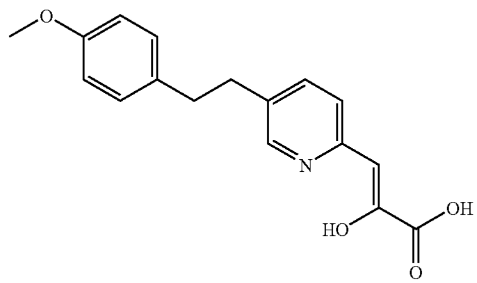 |
| I-135 | | 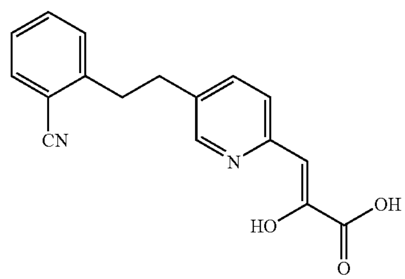 |
TABLE 21
| Comp. No. | Halogenated compound (starting compound) | Structure |
|---|---|---|
| I-136 | | 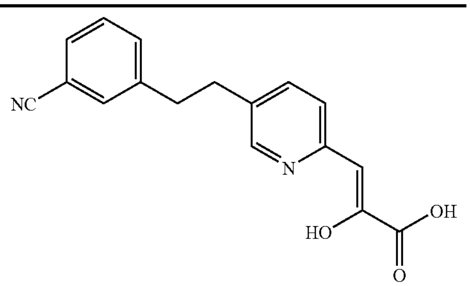 |
| I-137 | | 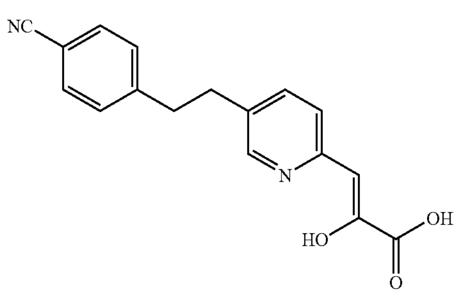 |

TABLE 21-continued
| Comp. No. | Halogenated compound (starting compound) | Structure |
|---|---|---|
| I-138 | 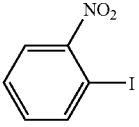 | 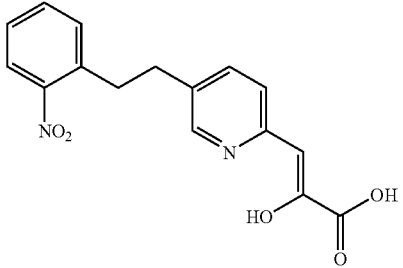 |
| I-139 | 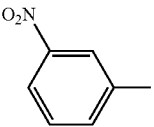 | 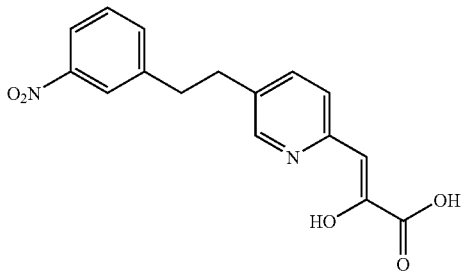 |
| I-140 | 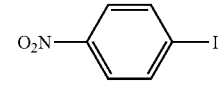 | 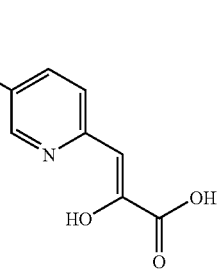 |
| I-141 | 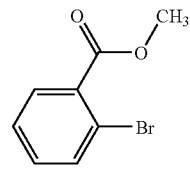 | 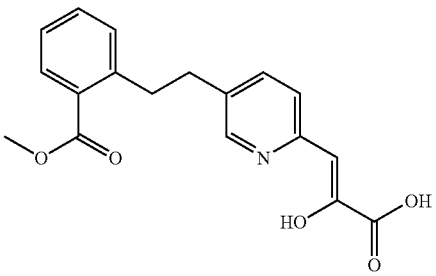 |

TABLE 22
| Comp. No. | Halogenated compound (starting compound) | Structure |
|---|---|---|
| I-142 | 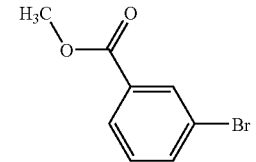 | 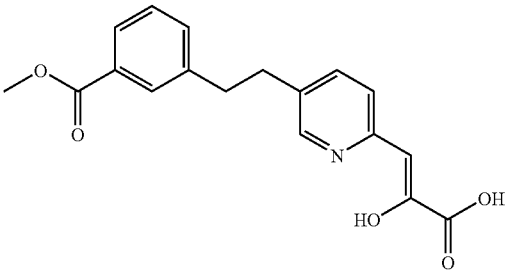 |
| I-143 | 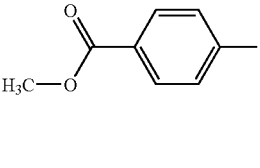 | 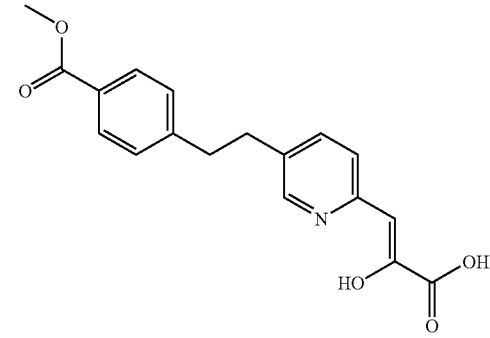 |
| I-144 | 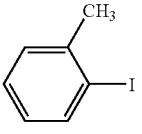 | 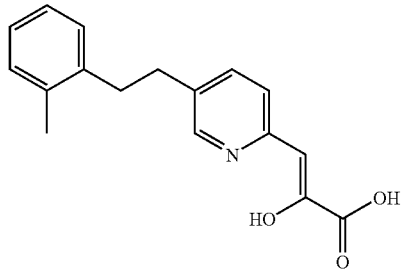 |
| I-145 | 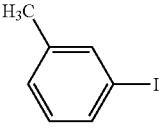 | 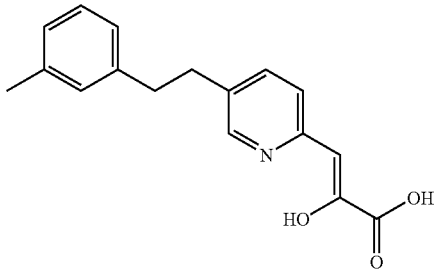 |
| I-146 | 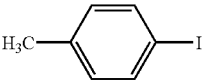 | 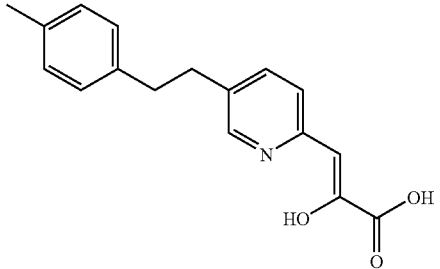 |

TABLE 22-continued
| Comp. No. | Halogenated compound (starting compound) | Structure |
|---|---|---|
| I-147 | 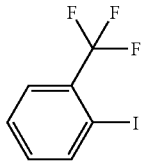 | 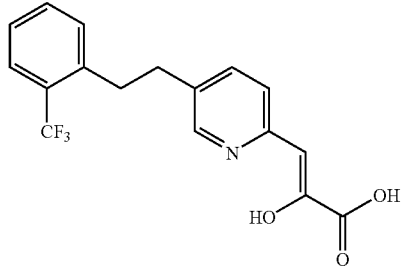 |
TABLE 23
| Comp. No. | Halogenated compound (starting compound) | Structure |
|---|---|---|
| I-148 | 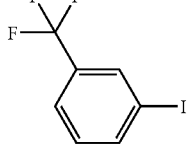 | 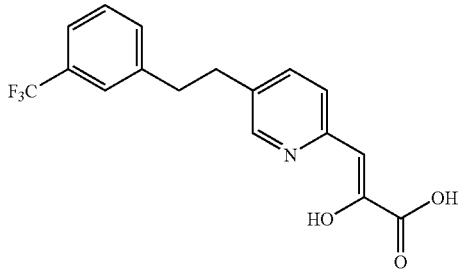 |
| I-149 | 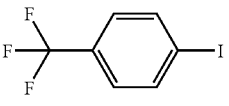 | 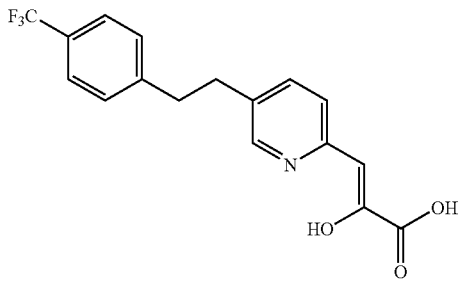 |
| I-150 | 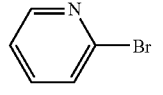 | 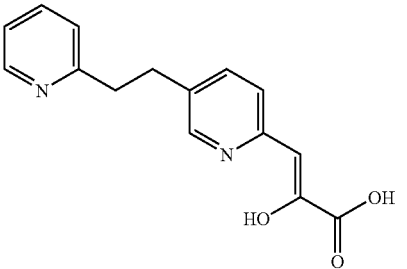 |
| I-151 | 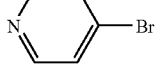 | 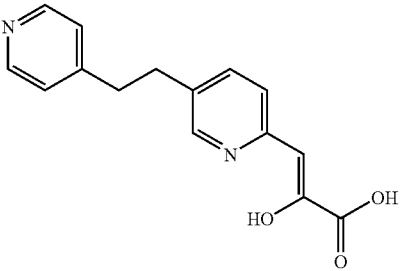 |

TABLE 23-continued

| Comp. No. | Halogenated compound (starting compound) | Structure |
|---|---|---|
| I-152 | 4-bromoisoquinoline | isoquinoline-CH₂CH₂-pyridine-CH=C(OH)-COOH |
| I-153 | 6-bromo-2(3H)-benzothiazolone | 2(3H)-benzothiazolone-CH₂CH₂-pyridine-CH=C(OH)-COOH |

TABLE 24

| Comp. No. | Halogenated compound (starting compound) | Structure |
|---|---|---|
| I-154 | 3-bromoquinoline | quinoline-CH₂CH₂-pyridine-CH=C(OH)-COOH |
| I-155 | 2-bromo-3-hydroxypyridine | (3-hydroxypyridin-2-yl)-CH₂CH₂-pyridine-CH=C(OH)-COOH |

TABLE 24-continued
| Comp. No. | Halogenated compound (starting compound) | Structure |
|---|---|---|
| I-156 | 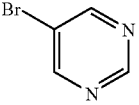 | 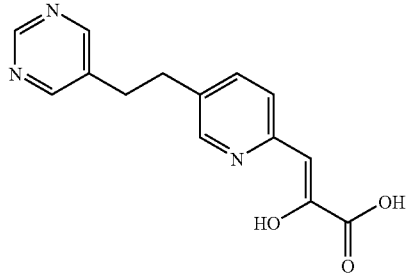 |
| I-157 | 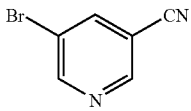 | 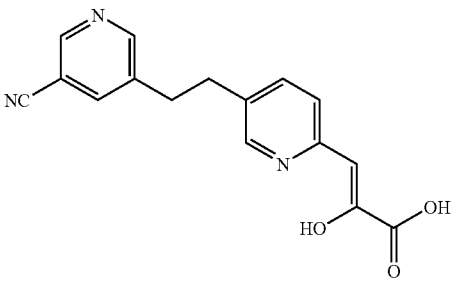 |
| I-158 | 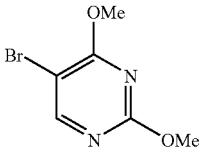 | 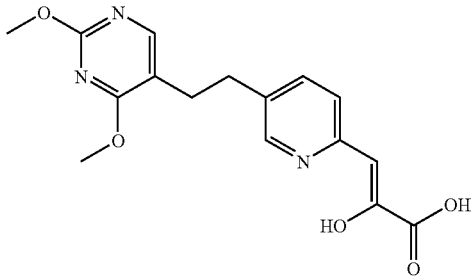 |
| I-159 | 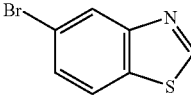 | 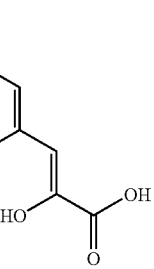 |
TABLE 25
| Comp. No. | Halogenated compound (starting compound) | Structure |
|---|---|---|
| I-160 | 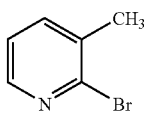 | 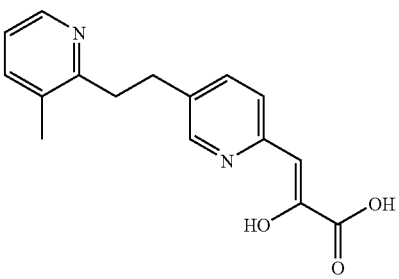 |

TABLE 25-continued
| Comp. No. | Halogenated compound (starting compound) | Structure |
|---|---|---|
| I-161 | 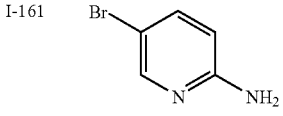 | 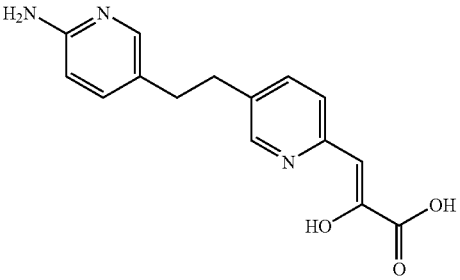 |
| I-162 | 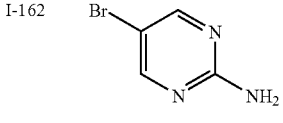 | 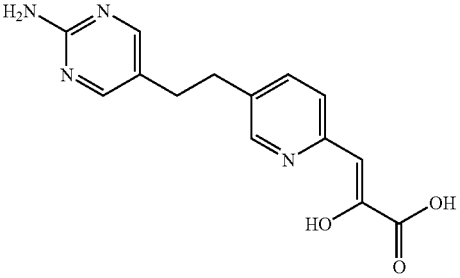 |
| I-163 | 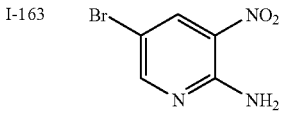 | 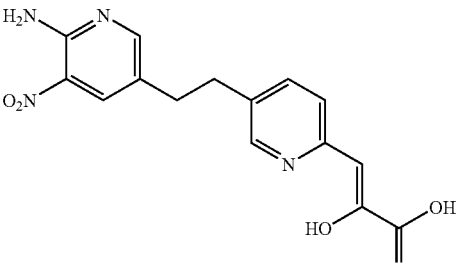 |
| I-164 | 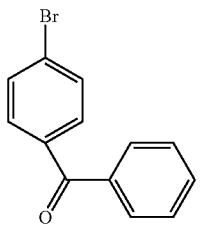 | 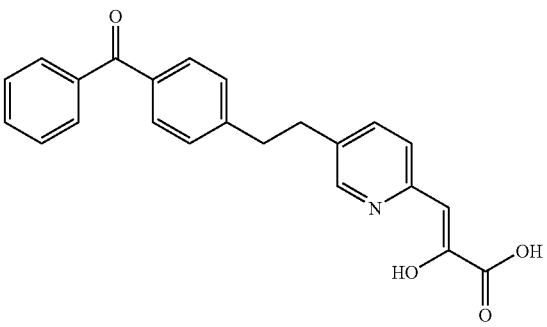 |
| I-165 | 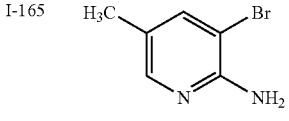 | 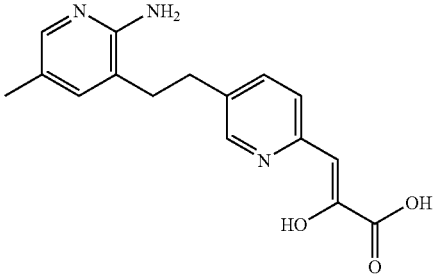 |

TABLE 26

| Comp. No. | Halogenated compound (starting compound) | Structure |
|---|---|---|
| I-166 | 5-bromonicotinamide | pyridine-3-carboxamide linked via ethylene to pyridine bearing (E)-3-hydroxy-2-carboxyvinyl group |
| I-167 | 2-iodoaniline | 2-aminophenyl-ethyl-pyridine with (E)-3-hydroxy-2-carboxyvinyl group |
| I-168 | 2-chloro-1-iodobenzene | 2-chlorophenyl-ethyl-pyridine with (E)-3-hydroxy-2-carboxyvinyl group |
| I-169 | 3-bromo-2-cyanothiophene | 2-cyanothien-3-yl-ethyl-pyridine with (E)-3-hydroxy-2-carboxyvinyl group |
| I-170 | 3-bromothiophene-2-carboxamide | 2-carbamoylthien-3-yl-ethyl-pyridine with (E)-3-hydroxy-2-carboxyvinyl group |

TABLE 26-continued
| Comp. No. | Halogenated compound (starting compound) | Structure |
|---|---|---|
| I-171 | | 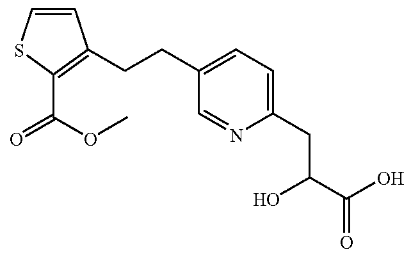 |
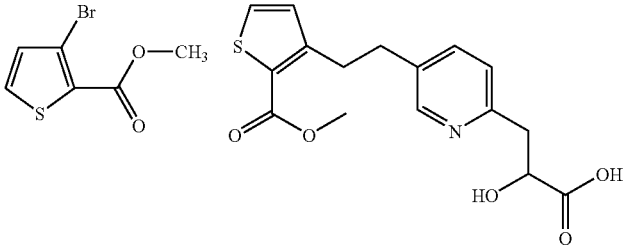
TABLE 27
| Comp. No. | Halogenated compound (starting compound) | Structure |
|---|---|---|
| I-172 | | 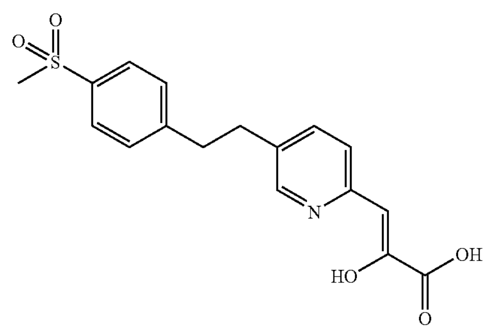 |
| I-173 | | 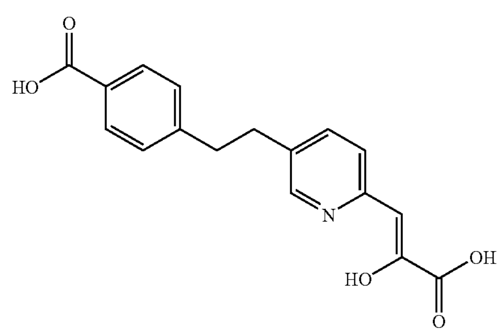 |
| I-174 | | 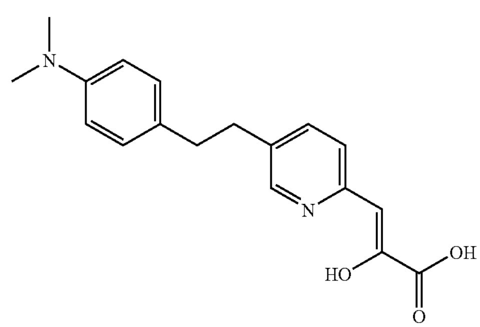 |

TABLE 27-continued

| Comp. No. | Halogenated compound (starting compound) | Structure |
|---|---|---|
| I-175 | 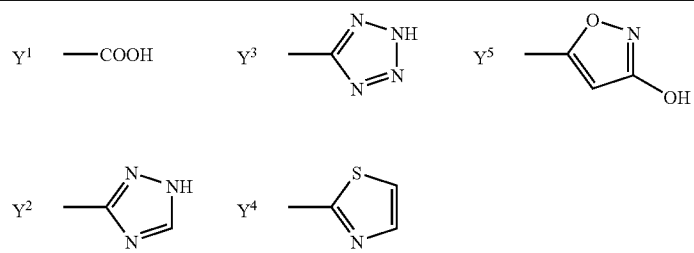 | 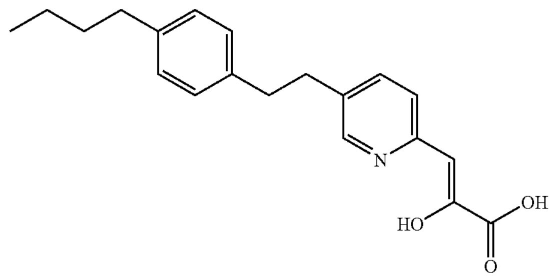 |

Example 175

Pyrimidine derivatives were prepared in accordance with the similar method shown above. In place of the above compound of the formula (J-2), 3-(6-vinylpyrimidin-4-yl)-2-hydroxyacrylic acid was used.

The following compounds can be prepared as well as the above shown compounds. These compounds are within the scope of the present invention.

TABLE 28

$Y^1$ —COOH
$Y^2$ — 1,2,4-triazol-3-yl (N-NH, N=N)
$Y^3$ — tetrazol-5-yl (N-NH, N=N-N)
$Y^4$ — thiazol-2-yl
$Y^5$ — 3-hydroxyisoxazol-5-yl $R^1-Z^3-Z^2-Z^1$—pyrimidine—CH=C(OH)—Y

| Comp. No. | $Z^1$ | $Z^2$ | $Z^3$ | $R^1$ | Y |
|---|---|---|---|---|---|
| B-1 | Bond | O | $CH_2$ | 4-F—Ph | $Y^1$ |
| B-2 | $CH_2$ | O | Bond | 4-F—Ph | $Y^1$ |
| B-3 | Bond | $CH_2CH_2$ | Bond | 4-F—Ph | $Y^1$ |
| B-4 | Bond | S | $CH_2$ | 4-F—Ph | $Y^1$ |
| B-5 | $CH_2$ | S | Bond | 4-F—Ph | $Y^1$ |
| B-6 | Bond | CONH | Bond | 4-F—Ph | $Y^1$ |
| B-7 | Bond | NHCO | Bond | 4-F—Ph | $Y^1$ |
| B-8 | Bond | CH=CH | Bond | 4-F—Ph | $Y^1$ |
| B-9 | Bond | $NHSO_2$ | Bond | 4-F—Ph | $Y^1$ |
| B-10 | Bond | $SO_2NH$ | Bond | 4-F—Ph | $Y^1$ |
| B-11 | Bond | $CH_2$ | Bond | 4-F—Ph | $Y^1$ |
| B-12 | Bond | NH | $CH_2$ | 4-F—Ph | $Y^1$ |
| B-13 | $CH_2$ | NH | Bond | 4-F—Ph | $Y^1$ |
| B-14 | Bond | CO | $CH_2$ | 4-F—Ph | $Y^1$ |
| B-15 | $CH_2$ | CO | Bond | 4-F—Ph | $Y^1$ |
| B-16 | Bond | O | $CH_2$ | Ph | $Y^1$ |
| B-17 | $CH_2$ | O | Bond | Ph | $Y^1$ |
| B-18 | Bond | S | $CH_2$ | Ph | $Y^1$ |
| B-19 | $CH_2$ | S | Bond | Ph | $Y^1$ |
| B-20 | Bond | CONH | Bond | Ph | $Y^1$ |
| B-21 | Bond | NHCO | Bond | Ph | $Y^1$ |
| B-22 | Bond | CH=CH | Bond | Ph | $Y^1$ |
| B-23 | Bond | $NHSO_2$ | Bond | Ph | $Y^1$ |
| B-24 | Bond | $SO_2NH$ | Bond | Ph | $Y^1$ |
| B-25 | Bond | $CH_2$ | Bond | Ph | $Y^1$ |
| B-26 | Bond | NH | $CH_2$ | Ph | $Y^1$ |
| B-27 | $CH_2$ | NH | Bond | Ph | $Y^1$ |
| B-28 | Bond | CO | $CH_2$ | Ph | $Y^1$ |

TABLE 29

Y¹ —COOH   Y³ = tetrazole   Y⁵ = isoxazole-OH

R¹—Z³—Z²—Z¹—[pyrimidine]—CH=C(OH)—Y

Y² = triazole   Y⁴ = thiazole

| Comp. No. | Z¹ | Z² | Z³ | R¹ | Y |
|---|---|---|---|---|---|
| B-29 | $CH_2$ | CO | Bond | Ph | $Y^1$ |
| C-1 | Bond | O | $CH_2$ | 4-F—Ph | $Y^2$ |
| C-2 | $CH_2$ | O | Bond | 4-F—Ph | $Y^2$ |
| C-3 | Bond | $CH_2CH_2$ | Bond | 4-F—Ph | $Y^2$ |
| C-4 | Bond | S | $CH_2$ | 4-F—Ph | $Y^2$ |
| C-5 | $CH_2$ | S | Bond | 4-F—Ph | $Y^2$ |
| C-6 | Bond | CONH | Bond | 4-F—Ph | $Y^2$ |
| C-7 | Bond | NHCO | Bond | 4-F—Ph | $Y^2$ |
| C-8 | Bond | CH=CH | Bond | 4-F—Ph | $Y^2$ |
| C-9 | Bond | $NHSO_2$ | Bond | 4-F—Ph | $Y^2$ |
| C-10 | Bond | $SO_2NH$ | Bond | 4-F—Ph | $Y^2$ |
| C-11 | Bond | $CH_2$ | Bond | 4-F—Ph | $Y^2$ |
| C-12 | Bond | NH | $CH_2$ | 4-F—Ph | $Y^2$ |
| C-13 | $CH_2$ | NH | Bond | 4-F—Ph | $Y^2$ |
| C-14 | Bond | CO | $CH_2$ | 4-F—Ph | $Y^2$ |
| C-15 | $CH_2$ | CO | Bond | 4-F—Ph | $Y^2$ |
| C-16 | Bond | O | $CH_2$ | Ph | $Y^2$ |
| C-17 | $CH_2$ | O | Bond | Ph | $Y^2$ |
| C-19 | Bond | S | $CH_2$ | Ph | $Y^2$ |
| C-20 | $CH_2$ | S | Bond | Ph | $Y^2$ |
| C-21 | Bond | CONH | Bond | Ph | $Y^2$ |
| C-22 | Bond | NHCO | Bond | Ph | $Y^2$ |
| C-23 | Bond | CH=CH | Bond | Ph | $Y^2$ |
| C-24 | Bond | $NHSO_2$ | Bond | Ph | $Y^2$ |
| C-25 | Bond | $SO_2NH$ | Bond | Ph | $Y^2$ |
| C-26 | Bond | $CH_2$ | Bond | Ph | $Y^2$ |
| C-27 | Bond | NH | $CH_2$ | Ph | $Y^2$ |

TABLE 30

Y¹ —COOH   Y³ = tetrazole   Y⁵ = isoxazole-OH

R¹—Z³—Z²—Z¹—[pyrimidine]—CH=C(OH)—Y

Y² = triazole   Y⁴ = thiazole

| Comp. No. | Z¹ | Z² | Z³ | R¹ | Y |
|---|---|---|---|---|---|
| C-28 | $CH_2$ | NH | Bond | Ph | $Y^2$ |
| C-29 | Bond | CO | $CH_2$ | Ph | $Y^2$ |
| C-30 | $CH_2$ | CO | Bond | Ph | $Y^2$ |
| D-1 | Bond | O | $CH_2$ | 4-F—Ph | $Y^3$ |
| D-2 | $CH_2$ | O | Bond | 4-F—Ph | $Y^3$ |
| D-3 | Bond | $CH_2CH_2$ | Bond | 4-F—Ph | $Y^3$ |
| D-4 | Bond | S | $CH_2$ | 4-F—Ph | $Y^3$ |
| D-5 | $CH_2$ | S | Bond | 4-F—Ph | $Y^3$ |
| D-6 | Bond | CONH | Bond | 4-F—Ph | $Y^3$ |
| D-7 | Bond | NHCO | Bond | 4-F—Ph | $Y^3$ |
| D-8 | Bond | CH=CH | Bond | 4-F—Ph | $Y^3$ |
| D-9 | Bond | $NHSO_2$ | Bond | 4-F—Ph | $Y^3$ |
| D-10 | Bond | $SO_2NH$ | Bond | 4-F—Ph | $Y^3$ |
| D-11 | Bond | $CH_2$ | Bond | 4-F—Ph | $Y^3$ |
| D-12 | Bond | NH | $CH_2$ | 4-F—Ph | $Y^3$ |
| D-13 | $CH_2$ | NH | Bond | 4-F—Ph | $Y^3$ |
| D-14 | Bond | CO | $CH_2$ | 4-F—Ph | $Y^3$ |
| D-15 | $CH_2$ | CO | Bond | 4-F—Ph | $Y^3$ |

TABLE 30-continued

| Comp. No. | Z¹ | Z² | Z³ | R¹ | Y |
|---|---|---|---|---|---|
| D-16 | Bond | O | CH$_2$ | Ph | Y$^3$ |
| D-17 | CH$_2$ | O | Bond | Ph | Y$^3$ |
| D-19 | Bond | S | CH$_2$ | Ph | Y$^3$ |
| D-20 | CH$_2$ | S | Bond | Ph | Y$^3$ |
| D-21 | Bond | CONH | Bond | Ph | Y$^3$ |
| D-22 | Bond | NHCO | Bond | Ph | Y$^3$ |
| D-23 | Bond | CH=CH | Bond | Ph | Y$^3$ |
| D-24 | Bond | NHSO$_2$ | Bond | Ph | Y$^3$ |
| D-25 | Bond | SO$_2$NH | Bond | Ph | Y$^3$ |

TABLE 31

Y$^1$ —COOH

Y$^2$ = 1H-1,2,4-triazol-3-yl

Y$^3$ = 2H-tetrazol-5-yl

Y$^4$ = thiazol-2-yl

Y$^5$ = 3-hydroxyisoxazol-5-yl

R$^1$—Z$^3$—Z$^2$—Z$^1$—(pyrimidine)—C(Y)=CH—OH

| Comp. No. | Z¹ | Z² | Z³ | R¹ | Y |
|---|---|---|---|---|---|
| D-26 | Bond | CH$_2$ | Bond | Ph | Y$^3$ |
| D-27 | Bond | NH | CH$_2$ | Ph | Y$^3$ |
| D-28 | CH$_2$ | NH | Bond | Ph | Y$^3$ |
| D-29 | Bond | CO | CH$_2$ | Ph | Y$^3$ |
| D-30 | CH$_2$ | CO | Bond | Ph | Y$^3$ |
| E-1 | Bond | O | CH$_2$ | 4-F—Ph | Y$^4$ |
| E-2 | CH$_2$ | O | Bond | 4-F—Ph | Y$^4$ |
| E-3 | Bond | CH$_2$CH$_2$ | Bond | 4-F—Ph | Y$^4$ |
| E-4 | Bond | S | CH$_2$ | 4-F—Ph | Y$^4$ |
| E-5 | CH$_2$ | S | Bond | 4-F—Ph | Y$^4$ |
| E-6 | Bond | CONH | Bond | 4-F—Ph | Y$^4$ |
| E-7 | Bond | NHCO | Bond | 4-F—Ph | Y$^4$ |
| E-8 | Bond | CH=CH | Bond | 4-F—Ph | Y$^4$ |
| E-9 | Bond | NHSO$_2$ | Bond | 4-F—Ph | Y$^4$ |
| E-10 | Bond | SO$_2$NH | Bond | 4-F—Ph | Y$^4$ |
| E-11 | Bond | CH$_2$ | Bond | 4-F—Ph | Y$^4$ |
| E-12 | Bond | NH | CH$_2$ | 4-F—Ph | Y$^4$ |
| E-13 | CH$_2$ | NH | Bond | 4-F—Ph | Y$^4$ |
| E-14 | Bond | CO | CH$_2$ | 4-F—Ph | Y$^4$ |
| E-15 | CH$_2$ | CO | Bond | 4-F—Ph | Y$^4$ |
| E-16 | Bond | O | CH$_2$ | Ph | Y$^4$ |
| E-17 | CH$_2$ | O | Bond | Ph | Y$^4$ |
| E-19 | Bond | S | CH$_2$ | Ph | Y$^4$ |
| E-20 | CH$_2$ | S | Bond | Ph | Y$^4$ |
| E-21 | Bond | CONH | Bond | Ph | Y$^4$ |
| E-22 | Bond | NHCO | Bond | Ph | Y$^4$ |
| E-23 | Bond | CH=CH | Bond | Ph | Y$^4$ |
| E-24 | Bond | NHSO$_2$ | Bond | Ph | Y$^4$ |

TABLE 32

Y$^1$ —COOH

Y$^2$ = 1H-1,2,4-triazol-3-yl

Y$^3$ = 2H-tetrazol-5-yl

Y$^4$ = thiazol-2-yl

Y$^5$ = 3-hydroxyisoxazol-5-yl

R$^1$—Z$^3$—Z$^2$—Z$^1$—(pyrimidine)—C(Y)=CH—OH

| Comp. No. | Z¹ | Z² | Z³ | R¹ | Y |
|---|---|---|---|---|---|
| E-25 | Bond | SO$_2$NH | Bond | Ph | Y$^4$ |
| E-26 | Bond | CH$_2$ | Bond | Ph | Y$^4$ |
| E-27 | Bond | NH | CH$_2$ | Ph | Y$^4$ |
| E-28 | CH$_2$ | NH | Bond | Ph | Y$^4$ |

TABLE 32-continued

| Comp. No. | Z¹ | Z² | Z³ | R¹ | Y |
|---|---|---|---|---|---|
| E-29 | Bond | CO | CH₂ | Ph | Y⁴ |
| E-30 | CH₂ | CO | Bond | Ph | Y⁴ |
| F-1 | Bond | O | CH₂ | 4-F—Ph | Y⁵ |
| F-2 | CH₂ | O | Bond | 4-F—Ph | Y⁵ |
| F-3 | Bond | CH₂CH₂ | Bond | 4-F—Ph | Y⁵ |
| F-4 | Bond | S | CH₂ | 4-F—Ph | Y⁵ |
| F-5 | CH₂ | S | Bond | 4-F—Ph | Y⁵ |
| F-6 | Bond | CONH | Bond | 4-F—Ph | Y⁵ |
| F-7 | Bond | NHCO | Bond | 4-F—Ph | Y⁵ |
| F-8 | Bond | CH=CH | Bond | 4-F—Ph | Y⁵ |
| F-9 | Bond | NHSO₂ | Bond | 4-F—Ph | Y⁵ |
| F-b | Bond | SO₂NH | Bond | 4-F—Ph | Y⁵ |
| F-11 | Bond | CH₂ | Bond | 4-F—Ph | Y⁵ |
| F-12 | Bond | NH | CH₂ | 4-F—Ph | Y⁵ |
| F-13 | CH₂ | NH | Bond | 4-F—Ph | Y⁵ |
| F-14 | Bond | CO | CH₂ | 4-F—Ph | Y⁵ |
| F-15 | CH₂ | CO | Bond | 4-F—Ph | Y⁵ |
| F-16 | Bond | O | CH₂ | Ph | Y⁵ |
| F-17 | CH₂ | O | Bond | Ph | Y⁵ |
| F-19 | Bond | S | CH₂ | Ph | Y⁵ |
| F-20 | CH₂ | S | Bond | Ph | Y⁵ |
| F-21 | Bond | CONH | Bond | Ph | Y⁵ |
| F-22 | Bond | NHCO | Bond | Ph | Y⁵ |
| F-23 | Bond | CH=CH | Bond | Ph | Y⁵ |

TABLE 33

$R^1-Z^3-Z^2-Z^1-$[pyrimidine]-CH=C(Y)(OH)

Y¹ —COOH
Y² —[1,2,4-triazole]
Y³ —[tetrazole]
Y⁴ —[thiazole]
Y⁵ —[isoxazole-OH]

| Comp. No. | Z¹ | Z² | Z³ | R¹ | Y |
|---|---|---|---|---|---|
| F-24 | Bond | NHSO₂ | Bond | Ph | Y⁵ |
| F-25 | Bond | SO₂NH | Bond | Ph | Y⁵ |
| F-26 | Bond | CH₂ | Bond | Ph | Y⁵ |
| F-27 | Bond | NH | CH₂ | Ph | Y⁵ |
| F-28 | CH₂ | NH | Bond | Ph | Y⁵ |
| F-29 | Bond | CO | CH₂ | Ph | Y⁵ |
| F-30 | CH₂ | CO | Bond | Ph | Y⁵ |

TABLE 34

$R^1-Z^3-Z^2-Z^1-$[pyridine]-CH=C(Y)(OH)

Y¹ —COOH
Y² —[1,2,4-triazole]
Y³ —[tetrazole]
Y⁴ —[thiazole]
Y⁵ —[isoxazole-OH]

| Comp. No. | Z¹ | Z² | Z³ | R¹ | Y |
|---|---|---|---|---|---|
| G-1 | Bond | O | CH₂ | 4-F—Ph | Y¹ |
| G-2 | CH₂ | O | Bond | 4-F—Ph | Y¹ |
| G-3 | Bond | CH₂CH₂ | Bond | 4-F—Ph | Y¹ |
| G-4 | Bond | S | CH₂ | 4-P—Ph | Y¹ |
| G-5 | CH₂ | S | Bond | 4-F—Ph | Y¹ |
| G-6 | Bond | CONH | Bond | 4-F—Ph | Y¹ |
| G-7 | Bond | NHCO | Bond | 4-F—Ph | Y¹ |
| G-8 | Bond | CH=CH | Bond | 4-F—Ph | Y¹ |
| G-9 | Bond | NHSO₂ | Bond | 4-F—Ph | Y¹ |
| G-1O | Bond | SO₂NH | Bond | 4-F—Ph | Y¹ |
| G-11 | Bond | CH₂ | Bond | 4-F—Ph | Y¹ |

TABLE 34-continued

| | | | | | |
|---|---|---|---|---|---|
| G-12 | Bond | NH | $CH_2$ | 4-F—Ph | $Y^1$ |
| G-13 | $CH_2$ | NH | Bond | 4-F—Ph | $Y^1$ |
| G-14 | Bond | CO | $CH_2$ | 4-F—Ph | $Y^1$ |
| G-15 | $CH_2$ | CO | Bond | 4-F—Ph | $Y^1$ |
| G-16 | $CH_2$ | O | Bond | Ph | $Y^1$ |
| G-18 | Bond | S | $CH_2$ | Ph | $Y^1$ |
| G-19 | $CH_2$ | S | Bond | Ph | $Y^1$ |
| G-20 | Bond | CONH | Bond | Ph | $Y^1$ |
| G-21 | Bond | NHCO | Bond | Ph | $Y^1$ |
| G-22 | Bond | CH=CH | Bond | Ph | $Y^1$ |
| G-23 | Bond | $NHSO_2$ | Bond | Ph | $Y^1$ |
| G-24 | Bond | $SO_2NH$ | Bond | Ph | $Y^1$ |
| G-25 | Bond | $CH_2$ | Bond | Ph | $Y^1$ |
| G-26 | Bond | NH | $CH_2$ | Ph | $Y^1$ |
| G-27 | $CH_2$ | NH | Bond | Ph | $Y^1$ |
| G-28 | Bond | CO | $CH_2$ | Ph | $Y^1$ |

TABLE 35

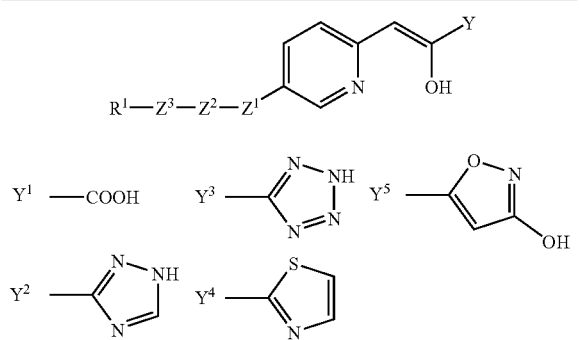

| Comp. No. | $Z^1$ | $Z^2$ | $Z^3$ | $R^1$ | Y |
|---|---|---|---|---|---|
| G-29 | $CH_2$ | CO | Bond | Ph | $Y^1$ |
| H-1 | Bond | O | $CH_2$ | 4-F-Ph | $Y^2$ |
| H-2 | $CH_2$ | O | Bond | 4-F-Ph | $Y^2$ |
| H-3 | Bond | $CH_2CH_2$ | Bond | 4-F-Ph | $Y^2$ |
| H-4 | Bond | S | $CH_2$ | 4-F-Ph | $Y^2$ |
| H-5 | $CH_2$ | S | Bond | 4-F-Ph | $Y^2$ |
| H-6 | Bond | CONH | Bond | 4-F-Ph | $Y^2$ |
| H-7 | Bond | NHCO | Bond | 4-F-Ph | $Y^2$ |
| H-8 | Bond | CH=CH | Bond | 4-F-Ph | $Y^2$ |
| H-9 | Bond | $NHSO_2$ | Bond | 4-F-Ph | $Y^2$ |
| H-10 | Bond | $SO_2NH$ | Bond | 4-F-Ph | $Y^2$ |
| H-11 | Bond | $CH_2$ | Bond | 4-F-Ph | $Y^2$ |
| H-12 | Bond | NH | $CH_2$ | 4-F-Ph | $Y^2$ |
| H-13 | $CH_2$ | NH | Bond | 4-F-Ph | $Y^2$ |
| H-14 | Bond | CO | $CH_2$ | 4-F-Ph | $Y^2$ |
| H-15 | $CH_2$ | CO | Bond | 4-F-Ph | $Y^2$ |
| H-16 | $CH_2$ | O | Bond | Ph | $Y^2$ |
| H-17 | Bond | $CH_2CH_2$ | Bond | Ph | $Y^2$ |
| H-18 | Bond | S | $CH_2$ | Ph | $Y^2$ |
| H-19 | $CH_2$ | S | Bond | Ph | $Y^2$ |
| H-20 | Bond | CONH | Bond | Ph | $Y^2$ |
| H-21 | Bond | NHCO | Bond | Ph | $Y^2$ |
| H-22 | Bond | CH=CH | Bond | Ph | $Y^2$ |
| H-23 | Bond | $NHSO_2$ | Bond | Ph | $Y^2$ |
| H-24 | Bond | $SO_2NH$ | Bond | Ph | $Y^2$ |
| H-25 | Bond | $CH_2$ | Bond | Ph | $Y^2$ |
| H-26 | Bond | NH | $CH_2$ | Ph | $Y^2$ |

TABLE 36

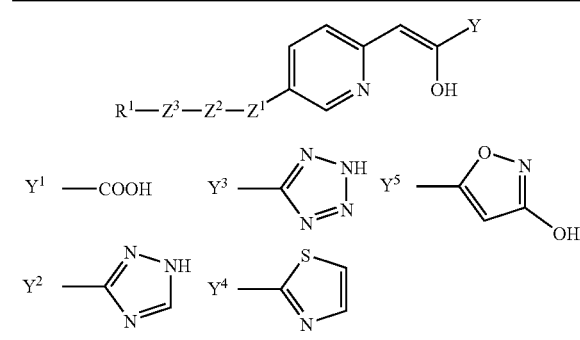

| Comp. No. | $Z^1$ | $Z^2$ | $Z^3$ | $R^1$ | Y |
|---|---|---|---|---|---|
| H-27 | $CH_2$ | NH | Bond | Ph | $Y^2$ |
| H-28 | Bond | CO | $CH_2$ | Ph | $Y^2$ |
| H-29 | $CH_2$ | CO | Bond | Ph | $Y^2$ |
| J-1 | Bond | O | $CH_2$ | 4-F-Ph | $Y^3$ |
| J-2 | $CH_2$ | O | Bond | 4-F-Ph | $Y^3$ |
| J-3 | Bond | $CH_2CH_2$ | Bond | 4-F-Ph | $Y^3$ |
| J-4 | Bond | S | $CH_2$ | 4-F-Ph | $Y^3$ |
| J-5 | $CH_2$ | S | Bond | 4-F-Ph | $Y^3$ |
| J-6 | Bond | CONH | Bond | 4-F-Ph | $Y^3$ |
| J-7 | Bond | NHCO | Bond | 4-F-Ph | $Y^3$ |
| J-8 | Bond | CH=CH | Bond | 4-F-Ph | $Y^3$ |
| J-9 | Bond | $NHSO_2$ | Bond | 4-F-Ph | $Y^3$ |
| J-10 | Bond | $SO_2NH$ | Bond | 4-F-Ph | $Y^3$ |
| J-11 | Bond | $CH_2$ | Bond | 4-F-Ph | $Y^3$ |
| J-12 | Bond | NH | $CH_2$ | 4-F-Ph | $Y^3$ |
| J-13 | $CH_2$ | NH | Bond | 4-F-Ph | $Y^3$ |
| J-14 | Bond | CO | $CH_2$ | 4-F-Ph | $Y^3$ |
| J-15 | $CH_2$ | CO | Bond | 4-F-Ph | $Y^3$ |
| J-16 | Bond | O | $CH_2$ | Ph | $Y^3$ |
| J-17 | $CH_2$ | O | Bond | Ph | $Y^3$ |
| J-18 | Bond | $CH_2CH_2$ | Bond | Ph | $Y^3$ |
| J-19 | Bond | S | $CH_2$ | Ph | $Y^3$ |
| J-20 | $CH_2$ | S | Bond | Ph | $Y^3$ |
| J-21 | Bond | CONH | Bond | Ph | $Y^3$ |
| J-22 | Bond | NHCO | Bond | Ph | $Y^3$ |
| J-23 | Bond | CH=CH | Bond | Ph | $Y^3$ |
| J-24 | Bond | $NHSO_2$ | Bond | Ph | $Y^3$ |

TABLE 37

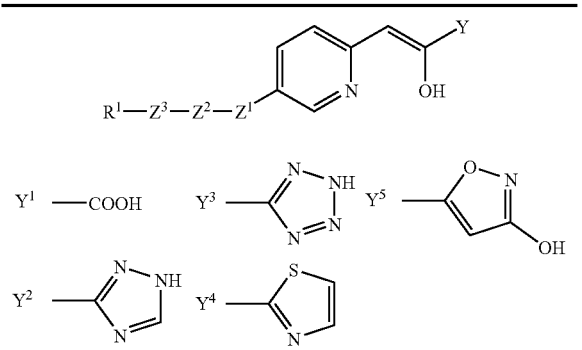

| Comp. No. | Z¹ | Z² | Z³ | R¹ | Y |
|---|---|---|---|---|---|
| J-25 | Bond | SO₂NH | Bond | Ph | Y³ |
| J-26 | Bond | CH₂ | Bond | Ph | Y³ |
| J-27 | Bond | NH | CH₂ | Ph | Y³ |
| J-28 | CH₂ | NH | Bond | Ph | Y³ |
| J-29 | Bond | CO | CH₂ | Ph | Y³ |
| J-30 | CH₂ | CO | Bond | Ph | Y³ |
| K-1 | Bond | O | CH₂ | 4-F-Ph | Y⁴ |
| K-2 | CH₂ | O | Bond | 4-F-Ph | Y⁴ |
| K-3 | Bond | CH₂CH₂ | Bond | 4-F-Ph | Y⁴ |
| K-4 | Bond | S | CH₂ | 4-F-Ph | Y⁴ |
| K-5 | CH₂ | S | Bond | 4-F-Ph | Y⁴ |
| K-6 | Bond | CONH | Bond | 4-F-Ph | Y⁴ |
| K-7 | Bond | NHCO | Bond | 4-F-Ph | Y⁴ |
| K-8 | Bond | CH=CH | Bond | 4-F-Ph | Y⁴ |
| K-9 | Bond | NHSO₂ | Bond | 4-F-Ph | Y⁴ |
| K-10 | Bond | SO₂NH | Bond | 4-F-Ph | Y⁴ |
| K-11 | Bond | CH₂ | Bond | 4-F-Ph | Y⁴ |
| K-12 | Bond | NH | CH₂ | 4-F-Ph | Y⁴ |
| K-13 | CH₂ | NH | Bond | 4-F-Ph | Y⁴ |
| K-14 | Bond | CO | CH₂ | 4-F-Ph | Y⁴ |
| K-15 | CH₂ | CO | Bond | 4-F-Ph | Y⁴ |
| K-16 | CH₂ | O | Bond | Ph | Y⁴ |
| H-17 | Bond | CH₂CH₂ | Bond | Ph | Y⁴ |
| K-18 | Bond | S | CH₂ | Ph | Y⁴ |
| K-19 | CH₂ | S | Bond | Ph | Y⁴ |
| K-20 | Bond | CONH | Bond | Ph | Y⁴ |
| K-21 | Bond | NHCO | Bond | Ph | Y⁴ |

TABLE 38

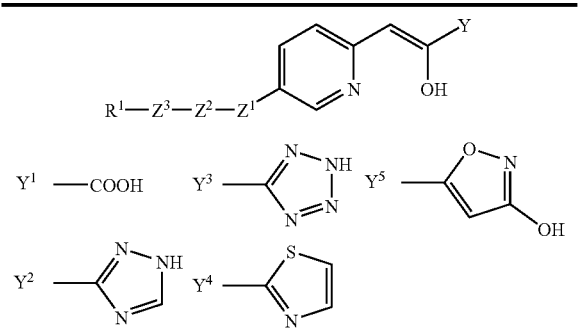

| Comp. No. | Z¹ | Z² | Z³ | R¹ | Y |
|---|---|---|---|---|---|
| K-22 | Bond | CH=CH | Bond | Ph | Y⁴ |
| K-23 | Bond | NHSO₂ | Bond | Ph | Y⁴ |
| K-24 | Bond | SO₂NH | Bond | Ph | Y⁴ |
| K-25 | Bond | CH₂ | Bond | Ph | Y⁴ |
| K-26 | Bond | NH | CH₂ | Ph | Y⁴ |
| K-27 | CH₂ | NH | Bond | Ph | Y⁴ |
| K-28 | Bond | CO | CH₂ | Ph | Y⁴ |
| K-29 | CH₂ | CO | Bond | Ph | Y⁴ |

TABLE 38-continued

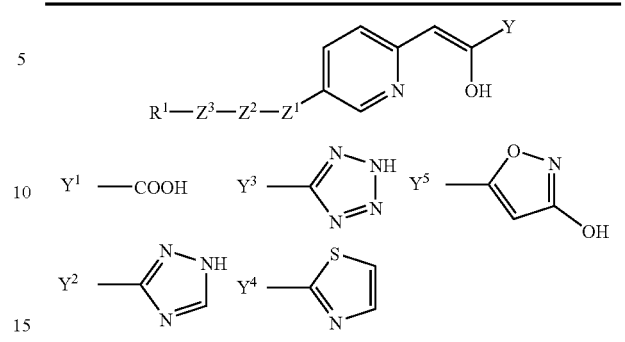

| Comp. No. | Z¹ | Z² | Z³ | R¹ | Y |
|---|---|---|---|---|---|
| L-1 | Bond | O | CH₂ | 4-F-Ph | Y⁵ |
| L-2 | CH₂ | O | Bond | 4-F-Ph | Y⁵ |
| L-3 | Bond | CH₂CH₂ | Bond | 4-F-Ph | Y⁵ |
| L-4 | Bond | S | CH₂ | 4-F-Ph | Y⁵ |
| L-5 | CH₂ | S | Bond | 4-F-Ph | Y⁵ |
| L-6 | Bond | CONH | Bond | 4-F-Ph | Y⁵ |
| L-7 | Bond | NHCO | Bond | 4-F-Ph | Y⁵ |
| L-8 | Bond | CH=CH | Bond | 4-F-Ph | Y⁵ |
| L-9 | Bond | NHSO₂ | Bond | 4-F-Ph | Y⁵ |
| L-10 | Bond | SO₂NH | Bond | 4-F-Ph | Y⁵ |
| L-11 | Bond | CH₂ | Bond | 4-F-Ph | Y⁵ |
| L-12 | Bond | NH | CH₂ | 4-F-Ph | Y⁵ |
| L-13 | CH₂ | NH | Bond | 4-F-Ph | Y⁵ |
| L-14 | Bond | CO | CH₂ | 4-F-Ph | Y⁵ |
| L-15 | CH₂ | CO | Bond | 4-F-Ph | Y⁵ |
| L-16 | Bond | O | CH₂ | Ph | Y⁵ |
| L-17 | CH₂ | O | Bond | Ph | Y⁵ |
| L-18 | Bond | CH₂CH₂ | Bond | Ph | Y⁵ |
| L-19 | Bond | S | CH₂ | Ph | Y⁵ |

TABLE 39

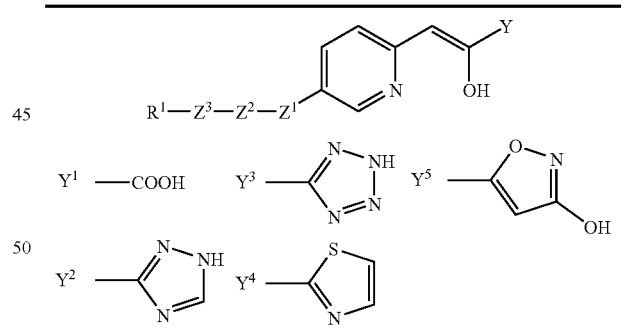

| Comp. No. | Z¹ | Z² | Z³ | R¹ | Y |
|---|---|---|---|---|---|
| L-20 | CH₂ | S | Bond | Ph | Y⁵ |
| L-21 | Bond | CONH | Bond | Ph | Y⁵ |
| L-22 | Bond | NHCO | Bond | Ph | Y⁵ |
| L-23 | Bond | CH=CH | Bond | Ph | Y⁵ |
| L-24 | Bond | NHSO₂ | Bond | Ph | Y⁵ |
| L.25 | Bond | SO₂NH | Bond | Ph | Y⁵ |
| L-26 | Bond | CH₂ | Bond | Ph | Y⁵ |
| L-27 | Bond | NH | CH₂ | Ph | Y⁵ |
| L-28 | CH₂ | NH | Bond | Ph | Y⁵ |
| L-29 | Bond | CO | CH₂ | Ph | Y⁵ |
| L-30 | CH₂ | CO | Bond | Ph | Y⁵ |

TABLE 40

$$R^1-Z^3-Z^2-Z^1-\text{[oxazole]}-CH=C(Y)(OH)$$

Y¹ —COOH    Y³ —[tetrazole]    Y⁵ —[isoxazole-OH]
Y² —[triazole-NH]    Y⁴ —[thiazole]

| Comp. No. | Z¹ | Z² | Z³ | R¹ | Y |
|---|---|---|---|---|---|
| M-1 | Bond | O | $CH_2$ | 4-F-Ph | $Y^1$ |
| M-2 | $CH_2$ | O | Bond | 4-F-Ph | $Y^1$ |
| M-3 | Bond | $CH_2CH_2$ | Bond | 4-F-Ph | $Y^1$ |
| M-4 | Bond | S | $CH_2$ | 4-F-Ph | $Y^1$ |
| M-5 | $CH_2$ | S | Bond | 4-F-Ph | $Y^1$ |
| M-6 | Bond | CONH | Bond | 4-F-Ph | $Y^1$ |
| M-7 | Bond | NHCO | Bond | 4-F-Ph | $Y^1$ |
| M-8 | Bond | CH=CH | Bond | 4-F-Ph | $Y^1$ |
| M-9 | Bond | $NHSO_2$ | Bond | 4-F-Ph | $Y^1$ |
| M-10 | Bond | $SO_2NH$ | Bond | 4-F-Ph | $Y^1$ |
| M-11 | Bond | $CH_2$ | Bond | 4-F-Ph | $Y^1$ |
| M-12 | Bond | NH | $CH_2$ | 4-F-Ph | $Y^1$ |
| M-13 | $CH_2$ | NH | Bond | 4-F-Ph | $Y^1$ |
| M-14 | Bond | CO | $CH_2$ | 4-F-Ph | $Y^1$ |
| M-15 | $CH_2$ | CO | Bond | 4-F-Ph | $Y^1$ |
| M-16 | Bond | O | $CH_2$ | Ph | $Y^1$ |
| M-17 | $CH_2$ | O | Bond | Ph | $Y^1$ |
| M-18 | Bond | $CH_2CH_2$ | Bond | Ph | $Y^1$ |
| M-19 | Bond | S | $CH_2$ | Ph | $Y^1$ |
| M-20 | $CH_2$ | S | Bond | Ph | $Y^1$ |
| M-21 | Bond | CONH | Bond | Ph | $Y^1$ |
| M-22 | Bond | NHCO | Bond | Ph | $Y^1$ |
| M-23 | Bond | CH=CH | Bond | Ph | $Y^1$ |
| M-24 | Bond | $NHSO_2$ | Bond | Ph | $Y^1$ |
| M-25 | Bond | $SO_2NH$ | Bond | Ph | $Y^1$ |
| M-26 | Bond | $CH_2$ | Bond | Ph | $Y^1$ |
| M-27 | Bond | NH | $CH_2$ | Ph | $Y^1$ |
| M-28 | $CH_2$ | NH | Bond | Ph | $Y^1$ |

TABLE 41

$$R^1-Z^3-Z^2-Z^1-\text{[oxazole]}-CH=C(Y)(OH)$$

Y¹ —COOH    Y³ —[tetrazole]    Y⁵ —[isoxazole-OH]
Y² —[triazole-NH]    Y⁴ —[thiazole]

| Comp. No. | Z¹ | Z² | Z³ | R¹ | Y |
|---|---|---|---|---|---|
| M-29 | Bond | CO | $CH_2$ | Ph | $Y^1$ |
| M-30 | $CH_2$ | CO | Bond | Ph | $Y^1$ |
| N-1 | Bond | O | $CH_2$ | 4-F-Ph | $Y^2$ |
| N-2 | $CH_2$ | O | Bond | 4-F-Ph | $Y^2$ |
| N-3 | Bond | $CH_2CH_2$ | Bond | 4-F-Ph | $Y^2$ |
| N-4 | Bond | S | $CH_2$ | 4-F-Ph | $Y^2$ |
| N-5 | $CH_2$ | S | Bond | 4-F-Ph | $Y^2$ |
| N-6 | Bond | CONH | Bond | 4-F-Ph | $Y^2$ |
| N-7 | Bond | NHCO | Bond | 4-F-Ph | $Y^2$ |

TABLE 41-continued

| Comp. No. | Z¹ | Z² | Z³ | R¹ | Y |
|---|---|---|---|---|---|
| N-8 | Bond | CH=CH | Bond | 4-F-Ph | $Y^2$ |
| N-9 | Bond | $NHSO_2$ | Bond | 4-F-Ph | $Y^2$ |
| N-10 | Bond | $SO_2NH$ | Bond | 4-F-Ph | $Y^2$ |
| N-11 | Bond | $CH_2$ | Bond | 4-F-Ph | $Y^2$ |
| N-12 | Bond | NH | $CH_2$ | 4-F-Ph | $Y^2$ |
| N-13 | $CH_2$ | NH | Bond | 4-F-Ph | $Y^2$ |
| N-14 | Bond | CO | $CH_2$ | 4-F-Ph | $Y^2$ |
| N-15 | $CH_2$ | CO | Bond | 4-F-Ph | $Y^2$ |
| N-16 | Bond | O | $CH_2$ | Ph | $Y^2$ |
| N-17 | $CH_2$ | O | Bond | Ph | $Y^2$ |
| N-18 | Bond | $CH_2CH_2$ | Bond | Ph | $Y^2$ |
| N-19 | Bond | S | $CH_2$ | Ph | $Y^2$ |
| N-20 | $CH_2$ | S | Bond | Ph | $Y^2$ |
| N-21 | Bond | CONH | Bond | Ph | $Y^2$ |
| N-22 | Bond | NHCO | Bond | Ph | $Y^2$ |
| N-23 | Bond | CH=CH | Bond | Ph | $Y^2$ |
| N-24 | Bond | $NHSO_2$ | Bond | Ph | $Y^2$ |
| N-25 | Bond | $SO_2NH$ | Bond | Ph | $Y^2$ |

TABLE 42

$$R^1-Z^3-Z^2-Z^1-\text{[oxazole]}-CH=C(Y)(OH)$$

Y¹ —COOH    Y³ —[tetrazole]    Y⁵ —[isoxazole-OH]
Y² —[triazole-NH]    Y⁴ —[thiazole]

| Comp. No. | Z¹ | Z² | Z³ | R¹ | Y |
|---|---|---|---|---|---|
| N-26 | Bond | $CH_2$ | Bond | Ph | $Y^2$ |
| N-27 | Bond | NH | $CH_2$ | Ph | $Y^2$ |
| N-28 | $CH_2$ | NH | Bond | Ph | $Y^2$ |
| N-29 | Bond | CO | $CH_2$ | Ph | $Y^2$ |
| N-30 | $CH_2$ | CO | Bond | Ph | $Y^2$ |
| O-1 | Bond | O | $CH_2$ | 4-F-Ph | $Y^3$ |
| O-2 | $CH_2$ | O | Bond | 4-F-Ph | $Y^3$ |
| O-3 | Bond | $CH_2CH_2$ | Bond | 4-F-Ph | $Y^3$ |
| O-4 | Bond | S | $CH_2$ | 4-F-Ph | $Y^3$ |
| O-5 | $CH_2$ | S | Bond | 4-F-Ph | $Y^3$ |
| O-6 | Bond | CONH | Bond | 4-F-Ph | $Y^3$ |
| O-7 | Bond | NHCO | Bond | 4-F-Ph | $Y^3$ |
| O-8 | Bond | CH=CH | Bond | 4-F-Ph | $Y^3$ |
| O-9 | Bond | $NHSO_2$ | Bond | 4-F-Ph | $Y^3$ |
| O-10 | Bond | $SO_2NH$ | Bond | 4-F-Ph | $Y^3$ |
| O-11 | Bond | $CH_2$ | Bond | 4-F-Ph | $Y^3$ |
| O-12 | Bond | NH | $CH_2$ | 4-F-Ph | $Y^3$ |
| O-13 | $CH_2$ | NH | Bond | 4-F-Ph | $Y^3$ |

TABLE 42-continued

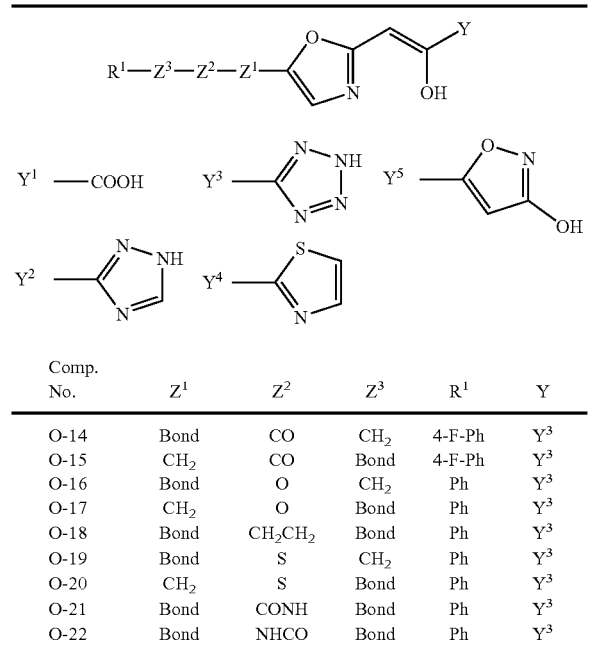

| Comp. No. | $Z^1$ | $Z^2$ | $Z^3$ | $R^1$ | Y |
|---|---|---|---|---|---|
| O-14 | Bond | CO | $CH_2$ | 4-F-Ph | $Y^3$ |
| O-15 | $CH_2$ | CO | Bond | 4-F-Ph | $Y^3$ |
| O-16 | Bond | O | $CH_2$ | Ph | $Y^3$ |
| O-17 | $CH_2$ | O | Bond | Ph | $Y^3$ |
| O-18 | Bond | $CH_2CH_2$ | Bond | Ph | $Y^3$ |
| O-19 | Bond | S | $CH_2$ | Ph | $Y^3$ |
| O-20 | $CH_2$ | S | Bond | Ph | $Y^3$ |
| O-21 | Bond | CONH | Bond | Ph | $Y^3$ |
| O-22 | Bond | NHCO | Bond | Ph | $Y^3$ |

TABLE 43

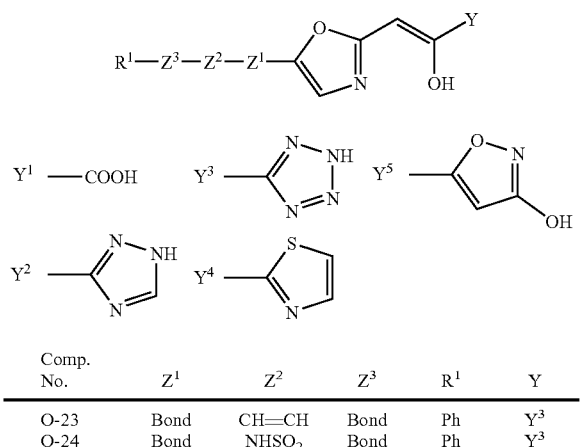

| Comp. No. | $Z^1$ | $Z^2$ | $Z^3$ | $R^1$ | Y |
|---|---|---|---|---|---|
| O-23 | Bond | CH=CH | Bond | Ph | $Y^3$ |
| O-24 | Bond | $NHSO_2$ | Bond | Ph | $Y^3$ |
| O-25 | Bond | $SO_2NH$ | Bond | Ph | $Y^3$ |
| O-26 | Bond | $CH_2$ | Bond | Ph | $Y^3$ |
| O-27 | Bond | NH | $CH_2$ | Ph | $Y^3$ |
| O-28 | $CH_2$ | NH | Bond | Ph | $Y^3$ |
| O-29 | Bond | CO | $CH_2$ | Ph | $Y^3$ |
| O-30 | $CH_2$ | CO | Bond | Ph | $Y^3$ |
| P-1 | Bond | O | $CH_2$ | 4-F-Ph | $Y^4$ |
| P-2 | $CH_2$ | O | Bond | 4-F-Ph | $Y^4$ |
| P-3 | Bond | $CH_2CH_2$ | Bond | 4-F-Ph | $Y^4$ |
| P-4 | Bond | S | $CH_2$ | 4-F-Ph | $Y^4$ |
| P-5 | $CH_2$ | S | Bond | 4-F-Ph | $Y^4$ |
| P-6 | Bond | CONH | Bond | 4-F-Ph | $Y^4$ |
| P-7 | Bond | NHCO | Bond | 4-F-Ph | $Y^4$ |
| P-8 | Bond | CH=CH | Bond | 4-F-Ph | $Y^4$ |
| P-9 | Bond | $NHSO_2$ | Bond | 4-F-Ph | $Y^4$ |
| P-10 | Bond | $SO_2NH$ | Bond | 4-F-Ph | $Y^4$ |
| P-11 | Bond | $CH_2$ | Bond | 4-F-Ph | $Y^4$ |
| P-12 | Bond | NH | $CH_2$ | 4-F-Ph | $Y^4$ |
| P-13 | $CH_2$ | NH | Bond | 4-F-Ph | $Y^4$ |
| P-14 | Bond | CO | $CH_2$ | 4-F-Ph | $Y^4$ |
| P-15 | $CH_2$ | CO | Bond | 4-F-Ph | $Y^4$ |
| P-16 | Bond | O | $CH_2$ | Ph | $Y^4$ |
| P-17 | $CH_2$ | O | Bond | Ph | $Y^4$ |

TABLE 43-continued

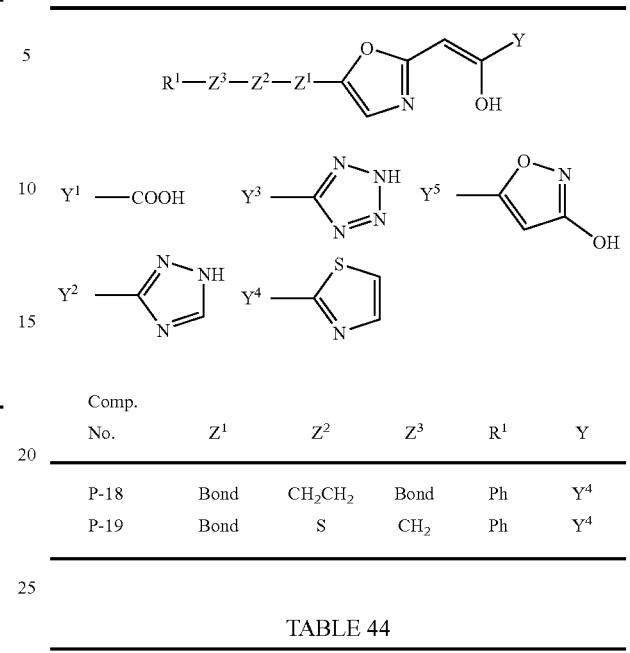

| Comp. No. | $Z^1$ | $Z^2$ | $Z^3$ | $R^1$ | Y |
|---|---|---|---|---|---|
| P-18 | Bond | $CH_2CH_2$ | Bond | Ph | $Y^4$ |
| P-19 | Bond | S | $CH_2$ | Ph | $Y^4$ |

TABLE 44

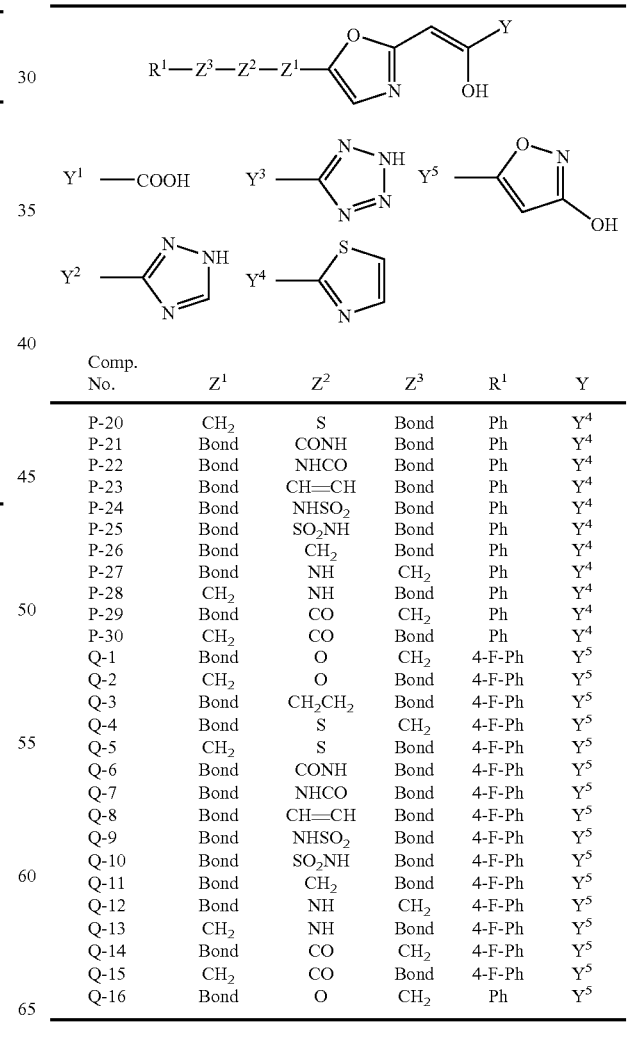

| Comp. No. | $Z^1$ | $Z^2$ | $Z^3$ | $R^1$ | Y |
|---|---|---|---|---|---|
| P-20 | $CH_2$ | S | Bond | Ph | $Y^4$ |
| P-21 | Bond | CONH | Bond | Ph | $Y^4$ |
| P-22 | Bond | NHCO | Bond | Ph | $Y^4$ |
| P-23 | Bond | CH=CH | Bond | Ph | $Y^4$ |
| P-24 | Bond | $NHSO_2$ | Bond | Ph | $Y^4$ |
| P-25 | Bond | $SO_2NH$ | Bond | Ph | $Y^4$ |
| P-26 | Bond | $CH_2$ | Bond | Ph | $Y^4$ |
| P-27 | Bond | NH | $CH_2$ | Ph | $Y^4$ |
| P-28 | $CH_2$ | NH | Bond | Ph | $Y^4$ |
| P-29 | Bond | CO | $CH_2$ | Ph | $Y^4$ |
| P-30 | $CH_2$ | CO | Bond | Ph | $Y^4$ |
| Q-1 | Bond | O | $CH_2$ | 4-F-Ph | $Y^5$ |
| Q-2 | $CH_2$ | O | Bond | 4-F-Ph | $Y^5$ |
| Q-3 | Bond | $CH_2CH_2$ | Bond | 4-F-Ph | $Y^5$ |
| Q-4 | Bond | S | $CH_2$ | 4-F-Ph | $Y^5$ |
| Q-5 | $CH_2$ | S | Bond | 4-F-Ph | $Y^5$ |
| Q-6 | Bond | CONH | Bond | 4-F-Ph | $Y^5$ |
| Q-7 | Bond | NHCO | Bond | 4-F-Ph | $Y^5$ |
| Q-8 | Bond | CH=CH | Bond | 4-F-Ph | $Y^5$ |
| Q-9 | Bond | $NHSO_2$ | Bond | 4-F-Ph | $Y^5$ |
| Q-10 | Bond | $SO_2NH$ | Bond | 4-F-Ph | $Y^5$ |
| Q-11 | Bond | $CH_2$ | Bond | 4-F-Ph | $Y^5$ |
| Q-12 | Bond | NH | $CH_2$ | 4-F-Ph | $Y^5$ |
| Q-13 | $CH_2$ | NH | Bond | 4-F-Ph | $Y^5$ |
| Q-14 | Bond | CO | $CH_2$ | 4-F-Ph | $Y^5$ |
| Q-15 | $CH_2$ | CO | Bond | 4-F-Ph | $Y^5$ |
| Q-16 | Bond | O | $CH_2$ | Ph | $Y^5$ |

TABLE 45

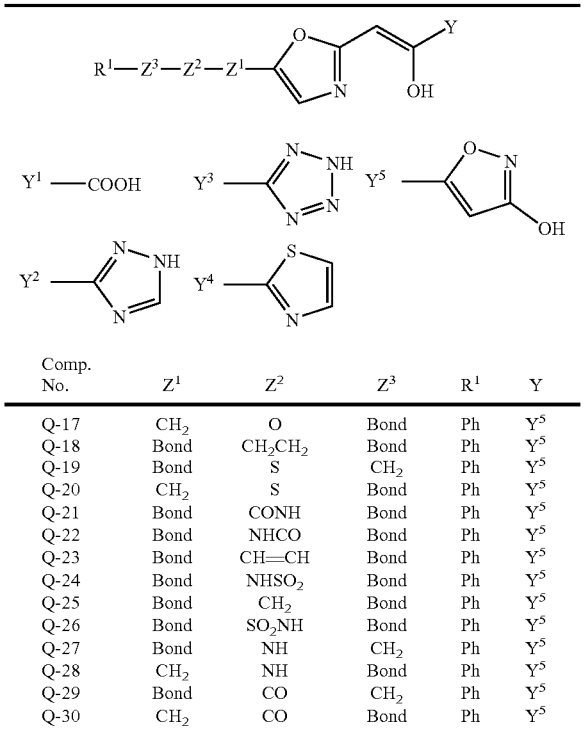

| Comp. No. | $Z^1$ | $Z^2$ | $Z^3$ | $R^1$ | Y |
|---|---|---|---|---|---|
| Q-17 | $CH_2$ | O | Bond | Ph | $Y^5$ |
| Q-18 | Bond | $CH_2CH_2$ | Bond | Ph | $Y^5$ |
| Q-19 | Bond | S | $CH_2$ | Ph | $Y^5$ |
| Q-20 | $CH_2$ | S | Bond | Ph | $Y^5$ |
| Q-21 | Bond | CONH | Bond | Ph | $Y^5$ |
| Q-22 | Bond | NHCO | Bond | Ph | $Y^5$ |
| Q-23 | Bond | CH=CH | Bond | Ph | $Y^5$ |
| Q-24 | Bond | $NHSO_2$ | Bond | Ph | $Y^5$ |
| Q-25 | Bond | $CH_2$ | Bond | Ph | $Y^5$ |
| Q-26 | Bond | $SO_2NH$ | Bond | Ph | $Y^5$ |
| Q-27 | Bond | NH | $CH_2$ | Ph | $Y^5$ |
| Q-28 | $CH_2$ | NH | Bond | Ph | $Y^5$ |
| Q-29 | Bond | CO | $CH_2$ | Ph | $Y^5$ |
| Q-30 | $CH_2$ | CO | Bond | Ph | $Y^5$ |

TABLE 46

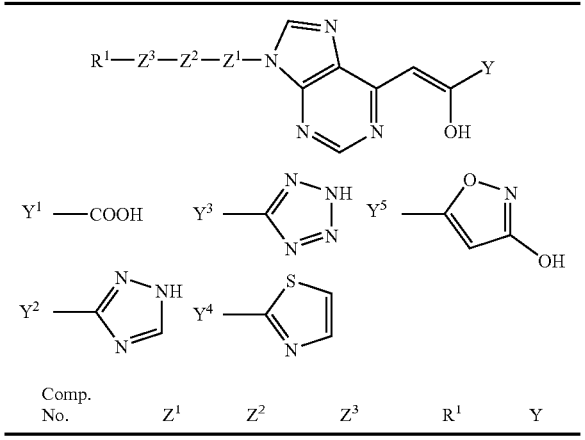

| Comp. No. | $Z^1$ | $Z^2$ | $Z^3$ | $R^1$ | Y |
|---|---|---|---|---|---|
| R-1 | Bond | $SO_2$ | Bond | 4-F-Ph | $Y^1$ |
| R-2 | Bond | O | Bond | 4-F-Ph | $Y^1$ |
| R-3 | Bond | $CH_2$ | Bond | 4-F-Ph | $Y^1$ |
| R-4 | Bond | S | Bond | 4-F-Ph | $Y^1$ |
| R-5 | Bond | CO | Bond | 4-F-Ph | $Y^1$ |
| R-6 | Bond | NH | Bond | 4-F-Ph | $Y^1$ |
| R-7 | Bond | $SO_2$ | Bond | Ph | $Y^1$ |
| R-8 | Bond | O | Bond | Ph | $Y^1$ |
| R-9 | Bond | S | Bond | Ph | $Y^1$ |
| R-10 | Bond | CO | Bond | Ph | $Y^1$ |
| R-11 | Bond | NH | Bond | Ph | $Y^1$ |
| S-1 | Bond | $SO_2$ | Bond | 4-F-Ph | $Y^2$ |
| S-2 | Bond | O | Bond | 4-F-Ph | $Y^2$ |
| S-3 | Bond | $CH_2$ | Bond | 4-F-Ph | $Y^2$ |
| S-4 | Bond | S | Bond | 4-F-Ph | $Y^2$ |
| S-5 | Bond | CO | Bond | 4-F-Ph | $Y^2$ |
| S-6 | Bond | NH | Bond | 4-F-Ph | $Y^2$ |
| S-7 | Bond | $SO_2$ | Bond | Ph | $Y^2$ |
| S-8 | Bond | O | Bond | Ph | $Y^2$ |
| S-9 | Bond | $CH_2$ | Bond | Ph | $Y^2$ |

TABLE 46-continued

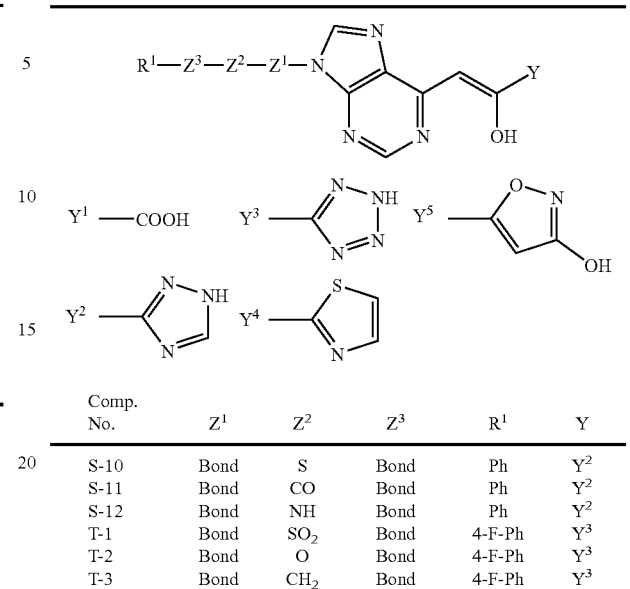

| Comp. No. | $Z^1$ | $Z^2$ | $Z^3$ | $R^1$ | Y |
|---|---|---|---|---|---|
| S-10 | Bond | S | Bond | Ph | $Y^2$ |
| S-11 | Bond | CO | Bond | Ph | $Y^2$ |
| S-12 | Bond | NH | Bond | Ph | $Y^2$ |
| T-1 | Bond | $SO_2$ | Bond | 4-F-Ph | $Y^3$ |
| T-2 | Bond | O | Bond | 4-F-Ph | $Y^3$ |
| T-3 | Bond | $CH_2$ | Bond | 4-F-Ph | $Y^3$ |
| T-4 | Bond | S | Bond | 4-F-Ph | $Y^3$ |

TABLE 47

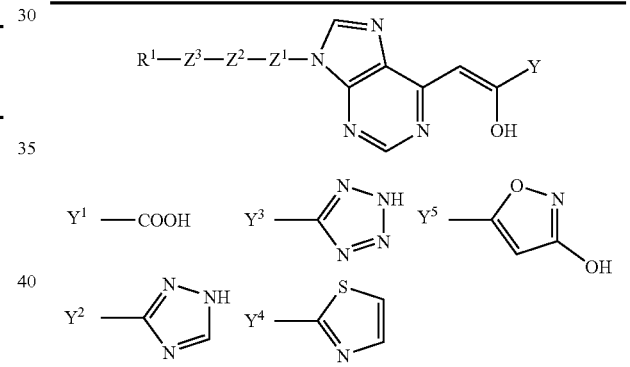

| Comp. No. | $Z^1$ | $Z^2$ | $Z^3$ | $R^1$ | Y |
|---|---|---|---|---|---|
| T-5 | Bond | CO | Bond | 4-F-Ph | $Y^3$ |
| T-6 | Bond | NH | Bond | 4-F-Ph | $Y^3$ |
| T-7 | Bond | $SO_2$ | Bond | Ph | $Y^3$ |
| T-8 | Bond | O | Bond | Ph | $Y^3$ |
| T-9 | Bond | $CH_2$ | Bond | Ph | $Y^3$ |
| T-10 | Bond | S | Bond | Ph | $Y^3$ |
| T-11 | Bond | CO | Bond | Ph | $Y^3$ |
| T-12 | Bond | NH | Bond | Ph | $Y^3$ |
| U-1 | Bond | $SO_2$ | Bond | 4-F-Ph | $Y^4$ |
| U-2 | Bond | O | Bond | 4-F-Ph | $Y^4$ |
| U-3 | Bond | $CH_2$ | Bond | 4-F-Ph | $Y^4$ |
| U-4 | Bond | S | Bond | 4-F-Ph | $Y^4$ |
| U-5 | Bond | CO | Bond | 4-F-Ph | $Y^4$ |
| U-6 | Bond | NH | Bond | 4-F-Ph | $Y^4$ |
| U-7 | Bond | $SO_2$ | Bond | Ph | $Y^4$ |
| U-8 | Bond | O | Bond | Ph | $Y^4$ |
| U-9 | Bond | $CH_2$ | Bond | Ph | $Y^4$ |
| U-10 | Bond | S | Bond | Ph | $Y^4$ |
| U-11 | Bond | CO | Bond | Ph | $Y^4$ |
| U-12 | Bond | NH | Bond | Ph | $Y^4$ |
| V-1 | Bond | $SO_2$ | Bond | 4-F-Ph | $Y^5$ |
| V-2 | Bond | O | Bond | 4-F-Ph | $Y^5$ |
| V-3 | Bond | $CH_2$ | Bond | 4-F-Ph | $Y^5$ |
| V-4 | Bond | S | Bond | 4-F-Ph | $Y^5$ |
| V-5 | Bond | CO | Bond | 4-F-Ph | $Y^5$ |

TABLE 47-continued

R¹—Z³—Z²—Z¹—[imidazo-pyrimidine]—CH=C(Y)(OH)

Y¹ —COOH

Y² —[triazole-NH]

Y³ —[tetrazole-NH]

Y⁴ —[thiazole]

Y⁵ —[isoxazole-OH]

| Comp. No. | Z¹ | Z² | Z³ | R¹ | Y |
|---|---|---|---|---|---|
| V-6 | Bond | NH | Bond | 4-F-Ph | Y⁵ |
| V-7 | Bond | SO₂ | Bond | Ph | Y⁵ |

TABLE 48

R¹—Z³—Z²—Z¹—[imidazo-pyrimidine]—CH=C(Y)(OH)

Y¹ —COOH

Y² —[triazole-NH]

Y³ —[tetrazole-NH]

Y⁴ —[thiazole]

Y⁵ —[isoxazole-OH]

| Comp. No. | Z¹ | Z² | Z³ | R¹ | Y |
|---|---|---|---|---|---|
| V-8 | Bond | O | Bond | Ph | Y⁵ |
| V-9 | Bond | CH₂ | Bond | Ph | Y⁵ |
| V-10 | Bond | S | Bond | Ph | Y⁵ |
| V-11 | Bond | CO | Bond | Ph | Y⁵ |
| V-12 | Bond | NH | Bond | Ph | Y⁵ |

Experimental Example

The inhibitory effects of the compounds of the present invention for HIV-1 integrase have been determined by the assay described below.

(1) Preparation of DNA solutions.

Substrate DNA and target DNA, which sequences were indicated below, were synthesized by Amersham Pharmacia Biotech and dissolved in KTE buffer (composition: 100 mM KCl, 1 mM EDTA, 10 mM Tris-HCl (pH 7.6)) at concentration of 2 pmol/μl and 5 pmol/μl, respectively. The DNA solutions were annealed with each complement by slowly cooling after heating.

(Substrate DNA)
5'-Biotin-ACC CTT TTA GTC AGT GTG GAA AAT CTC TAG CAG T-3'
3-GAA AAT CAG TCA CAC CTT TTA GAG ATC GTC A-5'

(Target DNA)
5'-TGA CCA AGG GCT AAT TCA CT-Dig-3'
3'-Dig-ACT GGT TCC CGA TTA AGT GA-5'

(2) Calculations of the percent inhibitions (the IC$_{50}$ values of test compounds)

Streptavidin, obtained from Vector Laboratories, was dissolved in 0.1 M carbonate buffer (composition: 90 mM Na$_2$CO$_3$, 10 mM NaHCO$_3$) at concentration of 40 μg/ml. After coating each well of microtiter plates (obtained from NUNC) with 50 μl of the above solution at 4° C. over night, each well was washed twice with PBS (composition: 13.7 mM NaCl, 0.27 mM KCl, 0.43 mM Na$_2$HPO$_4$, 0.14 mM KH$_2$PO$_4$) and blocked with 300 μl of 1% skim milk in PBS for 30 min. Additionally, each well was washed twice with PBS and added 50 μl of substrate DNA solution (2 pmol/μl). The microtiter plates were kept at room temperature for 30 min. Then, each well was washed twice with PBS and once with H$_2$O.

Subsequently, in the each well prepared above were added 45 μl of the reaction buffer prepared from 12 μl of the buffer (composition: 150 mM MOPS (pH 7.2), 75 mM MnCl$_2$, 50 mM 2-mercaptoethanol, 25% glycerol, 500 μg/ml bovine serum albumin-fraction V), 1 μl of target DNA (5 pmol/μl), and 32 μl of the distilled water. Additionally, 6 μl of either a test compound in DMSO or DMSO for positive control (PC) was mixed with the above reaction buffer, then 9 μl of an integrase solution (30 pmol) was added and mixed well. In the well of negative control (NC) was added 9 μl of the integrase dilution buffer (composition: 20 mM MOPS (pH7.2), 400 mM potassium glutamate, 1 mM EDTA, 0.1% NP-40, 20% glycerol, 1 mM DTT, 4M urea).

The microtiter plates were incubated at 30° C. for 1 hour. The reaction solution was removed and each well was washed twice with PBS. Subsequently, each well of the microtiter plates was filled with 100 μl of anti-digoxigenin antibody labeled with alkaline phosphatase (Sheep Fab fragment: obtained from Boehringer) and incubated at 30° C. for 1 hour. Then, each well was washed twice with 0.05% Tween20 in PBS and once with PBS. Next, 150 μl of the Alkaline phosphatase reaction buffer (composition: 10 mM p-Nitrophenylphosphate (obtained from Vector Laboratories), 5 mM MgCl$_2$, 100 mM NaCl, 100 mM Tris-HCl (pH 9.5)) was added in each well. The microtiter plates were incubated at 30° C. for 2 hours and the reaction was terminated by the addition of 50 μl of 1 N NaOH solution. The optical density (OD) at 405 nm of each well was measured and the percent inhibition was determined by the following expression.

The percent inhibition (%)=100[1−{(C abs.−NC abs.)/(PC abs.−NC abs.)}]

C abs.; the OD of the well of the compounds

NC abs. the OD of the negative control (NC)

PC abs.: the OD of the positive control (PC)

The IC 50 values, the concentration of the compounds at percent inhibition 50%, are shown in the following Table 1. The following Compounds (X-1 to 3) were used in order to compare an activity of the present compound with that of the compounds (X-1 to 3). Compound No. in the Table 1 is the same as compound No. of the above example.

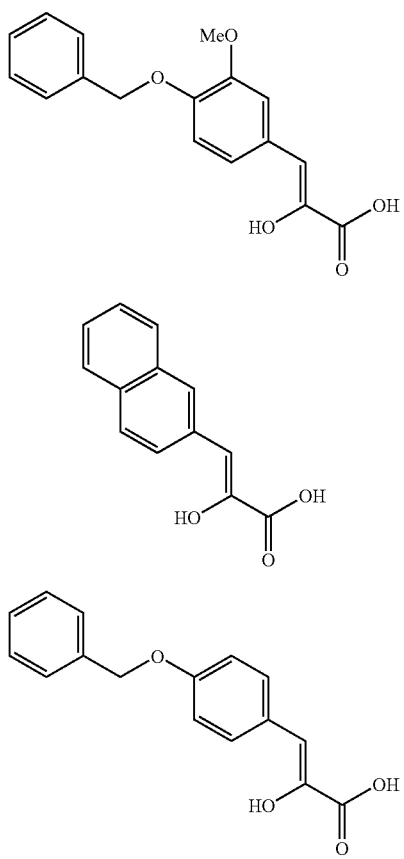

TABLE 49

| Compound No. | IC$_{50}$ (μg/ml) |
|---|---|
| I-2 | 0.53 |
| I-3 | 0.31 |
| I-7 | 1.3 |
| I-9 | 2.9 |
| I-14 | 0.95 |
| I-15 | 3.17 |
| I-17 | 3.4 |
| I-24 | 0.3 |
| I-25 | 0.13 |
| I-27 | 0.68 |
| I-35 | 0.44 |
| I-46 | 0.55 |
| I-47 | 0.5 |
| I-49 | 5.6 |
| X-1 | >100 |
| X-2 | >100 |
| X-3 | >100 |

Besides the compound shown above, examples of the compound having high activity are the compound I-91, 95, 97, 103, 109, 110, 111, 114, 115, 117, 119, or the like. These compounds are especially preferred among the compounds of the present invention.

Formulation Example

It is to be noted that the following Formulation Examples 1 to 8 are mere illustration, but not intended to limit the scope of the invention. The term "active ingredient" means the compounds of the formula (I), the prodrugs thereof, their pharmaceutical acceptable salts, or their solvates.

Formulation Example 1

Hard gelatin capsules are prepared using of the following ingredients:

|  | Dose (mg/capsule) |
|---|---|
| Active ingredient | 250 |
| Starch, dried | 200 |
| Magnesium stearate | 10 |
| Total | 460 mg |

Formulation Example 2

A tablet is prepared using of the following ingredients:

|  | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

|  | Weight |
|---|---|
| Active ingredient | 0.25 |
| Ethanol | 25.75 |
| Propellant 22 (chlorodifluoromethane) | 74.00 |
| Total | 100.00 |

The active ingredient is mixed with ethanol and the admixture added to a portion of the propellant 22, cooled to −30° C. and transferred to a filling device. The required amount is then fed to a stainless steel container and diluted with the reminder of the propellant. The valve units are then fitted to the container.

Formulation Example 4

Tablets, each containing 60 mg of active ingredient, are made as follows.

| Active ingredient | 60 mg |
|---|---|
| Starch | 45 mg |
| Microcrystals cellulose | 35 mg |

-continued

|  |  |
|---|---|
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

|  |  |
|---|---|
| Active ingredient | 80 mg |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppositories, each containing 225 mg of active ingredient, are made as follows:

|  |  |
|---|---|
| Active ingredient | 225 mg |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 ml dose, are made as follows:

|  |  |
|---|---|
| Active ingredient | 50 mg |
| Sodium carboxymethyl cellulose | 50 mg |

-continued

|  |  |
|---|---|
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

|  |  |
|---|---|
| Active ingredient | 100 mg |
| Isotonic saline | 1000 ml |

The solution of the above ingredients is generally administered intravenously to a subject at a rate of 1 ml per minute.

INDUSTRIAL APPLICABILITY

The present compound, the tautomer, the prodrug, the pharmaceutically acceptable salt, or the hydrate thereof has an inhibitory activity against integrase and efficient for treatment of AIDS and the like as an antiviral agent, an anti-HIV agent, and the like.

The invention claimed is:

1. A compound of the formula (I):

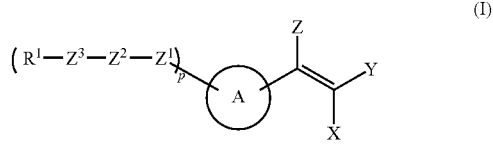

wherein

X is hydroxy;

Y is (1) —C(=$R^2$)—$R^3$—$R^4$ wherein $R^2$ is oxygen atom or sulfur atom, $R^3$ is oxygen atom, sulfur atom or N—$R^5$, $R^4$ is hydrogen, optionally substituted alkyl, optionally substituted alkenyl, optionally substituted alkynyl or optionally substituted aralkyl and $R^5$ is hydrogen, optionally substituted alkyl, optionally substituted alkenyl, optionally substituted alkynyl, optionally substituted alkoxy, optionally substituted cycloalkyl or optionally substituted aralkyl, or $R^4$ and N—$R^5$ may be taken together to form optionally substituted non-aromatic heterocyclic group;

(2) —S(=O)$_q$—$R^6$—$R^7$ wherein $R^6$ is oxygen atom or N—$R^7$, $R^7$ each is independently hydrogen, optionally substituted alkyl, optionally substituted alkenyl, optionally substituted alkynyl or optionally substituted aralkyl and q is 1 or 2;

(3) —S(=O)$_q$—R$^8$ wherein R$^8$ is optionally substituted alkyl, optionally substituted alkenyl, optionally substituted alkynyl or optionally substituted aralkyl and q is as defined above;

(4) —P(=O)(OH)$_2$;

(5) halogenated alkyl; or (6) optionally substituted heteroaryl;

Z is hydrogen or optionally substituted aralkyl;

Z$^1$ and Z$^3$ each is independently a bond, alkylene or alkenylene;

Z$^2$ is alkylene, a C2 to C6 straight or branched alkenylene, —CH(OH)—, —S—, —SO—, —SO$_2$—, —SO$_2$NR$^{10}$—, —NR$^{10}$SO$_2$—, —O—, —NR$^{10}$—, —NR$^{10}$CO—, —CONR$^{10}$—, —C(=O)—O—, —O—C(=O)— or —CO—;

R$^{10}$ is hydrogen, optionally substituted alkyl, optionally substituted alkenyl, optionally substituted alkynyl or optionally substituted aralkyl;

R$^1$ is optionally substituted branched alkyl, optionally substituted alkenyl, optionally substituted alkynyl, optionally substituted cycloalkyl, optionally substituted cycloalkenyl, optionally substituted non-aromatic heterocyclic group, optionally substituted aryl or optionally substituted heteroaryl;

p is 1 to 2, provided that when p is 2, the groups of the formula: —Z$^1$—Z$^2$—Z$^3$—R$^1$ are different from each other;

ring (A) is optionally further substituted aromatic heterocycle; and the group of the formula: —C(Z)=C(X)Y in the formula (I) substitutes at an atom adjacent to a hetero atom in ring (A), or a tautomer of the compound.

2. The compound according to claim 1 wherein Y is optionally substituted heteroaryl; and wherein the group of the formula: —C(Z)=C(X)— in the formula (I) substitutes at an atom adjacent to a hetero atom in Y, or a tautomer of the compound.

3. The compound according to claim 1 wherein X is hydroxy; Y is —C(=R$^2$)—R$^3$—R$^4$ wherein R$^2$ is oxygen atom, R$^3$ is oxygen atom or N—R$^5$, R$^4$ is hydrogen, optionally substituted alkyl, optionally substituted alkenyl, optionally substituted alkynyl or optionally substituted aralkyl and R$^5$ is hydrogen, optionally substituted alkyl, optionally substituted alkenyl, optionally substituted alkynyl, optionally substituted alkoxy, optionally substituted cycloalkyl or optionally substituted aralkyl, or R$^4$ and N—R$^5$ may be taken together to form optionally substituted non-aromatic heterocyclic group;

optionally substituted tetrazolyl; optionally substituted triazolyl; optionally substituted thiazolyl; optionally substituted isoxazolyl; optionally substituted pyrazinyl; optionally substituted imidazolyl; optionally substituted pyrimidinyl or optionally substituted pyridyl, or a tautomer of the compound.

4. The compound according to claim 1 wherein ring (A) is optionally further substituted aromatic heterocycle containing nitrogen atom, or a tautomer of the compound.

5. The compound according to claim 1 wherein ring (A) is optionally further substituted pyridine, optionally further substituted pyrazine, optionally further substituted pyrimidine, optionally further substituted oxazole, optionally further substituted thiadiazole, optionally further substituted quinoline, optionally further substituted isoquinoline, optionally further substituted purine, optionally further substituted benzoxazole or optionally further substituted benzimidazole, or a tautomer of the compound.

6. The compound according to claim 1 wherein Z$^2$ is alkylene or —O—, or a tautomer of the compound.

7. The compound according to claim 1 wherein Z$^1$ and Z$^3$ each is independently a bond or alkylene and R$^1$ is optionally substituted branched alkyl, optionally substituted cycloalkyl, optionally substituted non-aromatic heterocyclic group, optionally substituted aryl or optionally substituted heteroaryl, or a tautomer of the compound.

8. The compound according to claim 1 wherein Z$^1$ is a bond; Z$^2$ is alkylene or —O—; Z$^3$ is a bond or alkylene; and ring (A) is optionally further substituted pyridine, or a tautomer of the compound.

* * * * *